(12) United States Patent
Silver et al.

(10) Patent No.: US 10,406,345 B2
(45) Date of Patent: Sep. 10, 2019

(54) DUAL SENSOR ELECTRODES FOR PROVIDING ENHANCED RESUSCITATION FEEDBACK

(71) Applicant: ZOLL Medical Corporation, Chelmsford, MA (US)

(72) Inventors: Annemarie Silver, Bedford, MA (US); Fred Geheb, Danvers, MA (US); Lisa Campana, Waltham, MA (US); Paolo Giacometti, Nashua, NH (US); Gideon Butler, Portsmouth, NH (US); Gary A. Freeman, Waltham, MA (US); Christopher Joseph Desmarais, Acushnet, MA (US); Ian Durrant, Arlington, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 169 days.

(21) Appl. No.: 15/282,530

(22) Filed: Sep. 30, 2016

(65) Prior Publication Data

US 2017/0106183 A1   Apr. 20, 2017

Related U.S. Application Data

(60) Provisional application No. 62/242,749, filed on Oct. 16, 2015.

(51) Int. Cl.
*A61N 1/39* (2006.01)
*A61N 1/04* (2006.01)
(Continued)

(52) U.S. Cl.
CPC ........... *A61N 1/046* (2013.01); *A61H 31/005* (2013.01); *A61N 1/0492* (2013.01); *A61N 1/39* (2013.01);
(Continued)

(58) Field of Classification Search
CPC ...................................................... A61N 1/39
See application file for complete search history.

(56) References Cited

U.S. PATENT DOCUMENTS 4,059,099 A   11/1977 Davis
4,088,138 A    5/1978 Diack et al.
(Continued)

FOREIGN PATENT DOCUMENTS

EP   1057451 A2   12/2000
EP   1079310 A2    2/2001
(Continued)

OTHER PUBLICATIONS

Kovacs; "Rotation about an arbitrary axis and reflection through an arbitrary plane"; Annales Mathematicae et Informaticae; 2012; pp. 175-186; vol. 40.

*Primary Examiner* — William J Levicky
(74) *Attorney, Agent, or Firm* — The Webb Law Firm

(57) ABSTRACT

A system for facilitating resuscitation includes: a first electrode assembly having a therapy side and a first motion sensor; a second electrode assembly having a therapy side and a second motion sensor; processing circuitry operatively connected to and programmed to receive and process signals from the first and second motion sensors to estimate at least one of a chest compression depth and rate during administration of chest compressions and to compare the chest compression depth or rate to a desired range; and an output device for providing instructions to a user to administer chest compressions based on the comparison of the estimated chest compression depth or rate to the desired range. One or both of the electrode assemblies may be constructed so that the conductive therapeutic portion is able to maintain substantial conformance to the anatomy of the patient when coupled thereto. For example, at least a portion of the flexible electrode pad may be able to flex from a more rigid sensor housing, or the sensor housing itself may be relatively small compared to the flexible electrode pad so as not to cause lift off of the therapeutic side from the patient.

37 Claims, 28 Drawing Sheets

(51) Int. Cl.
*A61H 31/00* (2006.01)
*A61B 5/00* (2006.01)
*A61B 5/11* (2006.01)

(52) U.S. Cl.
CPC ......... *A61N 1/3925* (2013.01); *A61N 1/3987* (2013.01); *A61N 1/3993* (2013.01); *A61B 5/1107* (2013.01); *A61B 5/4848* (2013.01); *A61B 5/6801* (2013.01); *A61B 5/74* (2013.01); *A61B 2505/01* (2013.01); *A61B 2562/00* (2013.01); *A61B 2562/0219* (2013.01); *A61B 2562/04* (2013.01); *A61H 2031/002* (2013.01); *A61H 2201/0157* (2013.01); *A61H 2201/0188* (2013.01); *A61H 2201/1619* (2013.01); *A61H 2201/1623* (2013.01); *A61H 2201/50* (2013.01); *A61H 2201/5043* (2013.01); *A61H 2201/5048* (2013.01); *A61H 2201/5064* (2013.01); *A61H 2201/5097* (2013.01); *A61H 2230/06* (2013.01)

(56) References Cited

U.S. PATENT DOCUMENTS

| | | |
|---|---|---|
| 4,198,963 A | 4/1980 | Barkalow et al. |
| RE30,372 E | 8/1980 | Mirowski et al. |
| 4,273,114 A | 6/1981 | Barkalow et al. |
| 4,296,755 A | 10/1981 | Judell |
| 4,355,634 A | 10/1982 | Kanter |
| 4,588,383 A | 5/1986 | Parker et al. |
| 4,610,254 A | 9/1986 | Morgan et al. |
| 4,619,265 A | 10/1986 | Morgan et al. |
| 4,680,708 A | 7/1987 | Ambos et al. |
| 4,781,200 A | 11/1988 | Baker |
| 4,928,674 A | 5/1990 | Halperin et al. |
| 4,930,517 A | 6/1990 | Cohen et al. |
| 4,947,857 A | 8/1990 | Albert et al. |
| 4,987,783 A | 1/1991 | D'Antonio et al. |
| 5,077,667 A | 12/1991 | Brown et al. |
| 5,092,341 A | 3/1992 | Kelen |
| 5,109,862 A | 5/1992 | Kelen et al. |
| 5,247,945 A | 9/1993 | Heinze et al. |
| 5,262,958 A | 11/1993 | Chui et al. |
| 5,285,792 A | 2/1994 | Sjoquist et al. |
| 5,330,526 A | 7/1994 | Fincke et al. |
| RE34,800 E | 11/1994 | Hutchins |
| 5,365,426 A | 11/1994 | Siegel et al. |
| 5,391,187 A | 2/1995 | Freeman |
| 5,402,520 A | 3/1995 | Schnitta |
| 5,421,342 A | 6/1995 | Mortara |
| 5,439,483 A | 8/1995 | Duong-Van |
| 5,454,779 A | 10/1995 | Lurie et al. |
| 5,466,244 A | 11/1995 | Morgan |
| 5,471,991 A | 12/1995 | Shinnar |
| 5,474,574 A | 12/1995 | Payne et al. |
| 5,496,257 A | 3/1996 | Kelly |
| 5,511,553 A | 4/1996 | Segalowitz |
| 5,513,649 A | 5/1996 | Gevins et al. |
| 5,555,889 A | 9/1996 | Karagueuzian et al. |
| 5,562,710 A | 10/1996 | Olsen et al. |
| 5,589,639 A | 12/1996 | D'Antonio et al. |
| 5,591,213 A | 1/1997 | Morgan |
| 5,611,815 A | 3/1997 | Cole et al. |
| 5,619,265 A | 4/1997 | Suzuki et al. |
| 5,645,571 A | 7/1997 | Olson et al. |
| 5,662,690 A | 9/1997 | Cole et al. |
| 5,674,253 A | 10/1997 | Adams et al. |
| 5,683,424 A | 11/1997 | Brown et al. |
| 5,700,281 A | 12/1997 | Brewer et al. |
| 5,704,365 A | 1/1998 | Albrecht et al. |
| 5,735,879 A | 4/1998 | Gliner et al. |
| 5,738,637 A | 4/1998 | Kelly et al. |
| 5,755,671 A | 5/1998 | Albrecht et al. |
| 5,772,604 A | 6/1998 | Langberg et al. |
| 5,782,888 A | 7/1998 | Sun et al. |
| 5,831,164 A | 11/1998 | Reddi et al. |
| 5,876,350 A | 3/1999 | Lo et al. |
| 5,957,856 A | 9/1999 | Weil et al. |
| 5,967,995 A | 10/1999 | Shusterman et al. |
| 5,978,693 A | 11/1999 | Hamilton et al. |
| 5,999,852 A | 12/1999 | Elabbady et al. |
| 6,016,445 A | 1/2000 | Baura |
| 6,125,298 A | 9/2000 | Olson et al. |
| 6,125,299 A | 9/2000 | Groenke et al. |
| 6,171,257 B1 | 1/2001 | Weil et al. |
| 6,171,267 B1 | 1/2001 | Baldwin, II |
| 6,174,295 B1 | 1/2001 | Cantrell et al. |
| 6,178,357 B1 | 1/2001 | Gliner et al. |
| 6,188,928 B1 | 2/2001 | Noren et al. |
| 6,224,562 B1 | 5/2001 | Lurie et al. |
| 6,246,907 B1 | 6/2001 | Lin et al. |
| 6,263,238 B1 | 7/2001 | Brewer et al. |
| 6,289,243 B1 | 9/2001 | Lin et al. |
| 6,306,107 B1 | 10/2001 | Myklebust et al. |
| 6,308,094 B1 | 10/2001 | Shusterman et al. |
| 6,309,695 B1 | 10/2001 | Singh |
| 6,344,623 B1 | 2/2002 | Yamazaki et al. |
| 6,351,671 B1 | 2/2002 | Myklebust et al. |
| 6,360,125 B1 | 3/2002 | Weil et al. |
| 6,360,602 B1 | 3/2002 | Tazartes et al. |
| 6,390,996 B1 | 5/2002 | Halperin et al. |
| 6,393,316 B1 | 5/2002 | Gillberg et al. |
| 6,411,843 B1 | 6/2002 | Zarychta |
| 6,418,342 B1 | 7/2002 | Owen et al. |
| 6,427,685 B1 | 8/2002 | Ray, II |
| 6,438,419 B1 | 8/2002 | Callaway et al. |
| 6,453,272 B1 | 9/2002 | Slechta |
| 6,480,734 B1 | 11/2002 | Zhang et al. |
| 6,496,731 B1 | 12/2002 | Lovett |
| 6,597,943 B2 | 7/2003 | Taha et al. |
| 6,599,258 B1 | 7/2003 | Bystrom et al. |
| 6,622,036 B1 | 9/2003 | Suffin |
| 6,622,042 B1 | 9/2003 | Thacker |
| 6,658,290 B1 | 12/2003 | Lin et al. |
| 6,671,545 B2 | 12/2003 | Fincke |
| 6,687,540 B2 | 2/2004 | Marcovecchio |
| 6,697,671 B1 | 2/2004 | Nova et al. |
| 6,807,442 B1 | 10/2004 | Myklebust et al. |
| 6,827,695 B2 | 12/2004 | Palazzolo et al. |
| 6,961,612 B2 | 11/2005 | Elghazzawi et al. |
| 6,990,373 B2 | 1/2006 | Jayne et al. |
| 6,993,386 B2 | 1/2006 | Lin et al. |
| 7,006,865 B1 | 2/2006 | Cohen et al. |
| 7,013,176 B2 | 3/2006 | Ding et al. |
| 7,032,596 B2 | 4/2006 | Thompson et al. |
| 7,085,601 B1 | 8/2006 | Bardy et al. |
| 7,089,055 B2 | 8/2006 | Cates et al. |
| 7,220,235 B2 | 5/2007 | Geheb et al. |
| 7,463,922 B1 | 12/2008 | Snyder et al. |
| 7,488,293 B2 | 2/2009 | Marcovecchio et al. |
| 7,565,194 B2 | 7/2009 | Tan et al. |
| 7,708,683 B2 | 5/2010 | Hadley |
| 7,831,299 B2 | 11/2010 | Tan et al. |
| 8,165,671 B2 | 4/2012 | Freeman et al. |
| 8,617,853 B2 | 12/2013 | Liang et al. |
| 8,951,213 B2 | 2/2015 | Butler et al. |
| 9,125,793 B2 | 9/2015 | Palazzolo et al. |
| 9,289,134 B2 | 3/2016 | Tan et al. |
| 9,545,359 B2 | 1/2017 | Freeman et al. |
| 2001/0018562 A1 | 8/2001 | Sherman et al. |
| 2001/0047140 A1 | 11/2001 | Freeman |
| 2002/0026131 A1 | 2/2002 | Halperin |
| 2002/0055694 A1 | 5/2002 | Halperin et al. |
| 2002/0133197 A1 | 9/2002 | Snyder et al. |
| 2002/0165471 A1 | 11/2002 | Halperin et al. |
| 2002/0165585 A1 | 11/2002 | Dupelle et al. |
| 2002/0193711 A1 | 12/2002 | Halperin et al. |
| 2003/0023277 A1 | 1/2003 | Owen et al. |
| 2003/0055460 A1 | 3/2003 | Owen et al. |
| 2003/0055477 A1 | 3/2003 | Dupelle et al. |
| 2003/0083586 A1 | 5/2003 | Ferek-Petric |
| 2003/0083699 A1 | 5/2003 | Hamilton et al. |
| 2003/0088285 A1 | 5/2003 | Marcovecchio et al. |
| 2003/0130697 A1 | 7/2003 | Halperin et al. |

(56) References Cited

U.S. PATENT DOCUMENTS

| | | |
|---|---|---|
| 2003/0144699 A1 | 7/2003 | Freeman |
| 2003/0171661 A1 | 9/2003 | Tong |
| 2003/0195567 A1 | 10/2003 | Jayne et al. |
| 2004/0049234 A1 | 3/2004 | Morgan et al. |
| 2004/0059237 A1 | 3/2004 | Narayan et al. |
| 2004/0162585 A1 | 8/2004 | Elghazzawi et al. |
| 2004/0171954 A1 | 9/2004 | Holman |
| 2004/0210172 A1 | 10/2004 | Palazzolo et al. |
| 2004/0215244 A1 | 10/2004 | Marcovecchio et al. |
| 2004/0267324 A1 | 12/2004 | Geheb et al. |
| 2005/0021094 A1 | 1/2005 | Ostroff et al. |
| 2005/0027317 A1 | 2/2005 | Langer |
| 2005/0070964 A1 | 3/2005 | Hansen et al. |
| 2005/0209525 A1* | 9/2005 | Bojovic ............ A61B 5/04011 600/512 |
| 2006/0036292 A1 | 2/2006 | Smith et al. |
| 2006/0122648 A1 | 6/2006 | Elghazzawi et al. |
| 2006/0129190 A1 | 6/2006 | Sullivan et al. |
| 2006/0129191 A1 | 6/2006 | Sullivan et al. |
| 2006/0136000 A1 | 6/2006 | Bowers |
| 2006/0155336 A1 | 7/2006 | Heath |
| 2006/0173498 A1 | 8/2006 | Banville et al. |
| 2006/0173499 A1 | 8/2006 | Hampton et al. |
| 2006/0173500 A1 | 8/2006 | Walker et al. |
| 2006/0173501 A1 | 8/2006 | Stickney et al. |
| 2006/0206152 A1 | 9/2006 | Covey et al. |
| 2006/0229679 A1 | 10/2006 | Joo |
| 2006/0259080 A1 | 11/2006 | Vaisnys et al. |
| 2007/0032829 A1 | 2/2007 | Ostroff |
| 2007/0179539 A1 | 8/2007 | Degroot et al. |
| 2007/0219588 A1* | 9/2007 | Freeman ............ A61H 31/005 607/5 |
| 2007/0233197 A1 | 10/2007 | Jung et al. |
| 2008/0009908 A1 | 1/2008 | Parascandola et al. |
| 2008/0015645 A1 | 1/2008 | Kelly et al. |
| 2008/0033494 A1 | 2/2008 | Swerdlow |
| 2008/0033495 A1 | 2/2008 | Kumar |
| 2008/0046015 A1 | 2/2008 | Freeman et al. |
| 2009/0029332 A1* | 1/2009 | Solosko ............ A61N 1/39 607/5 |
| 2010/0022904 A1 | 1/2010 | Centen |
| 2012/0010543 A1* | 1/2012 | Johnson ............ A61N 1/3925 607/6 |
| 2012/0083720 A1* | 4/2012 | Centen ............ A61H 31/005 601/41 |
| 2012/0146797 A1* | 6/2012 | Oskin ............ A61N 1/04 340/573.1 |
| 2013/0023781 A1 | 1/2013 | Freeman et al. |
| 2013/0060173 A1 | 3/2013 | Palazzolo et al. |
| 2013/0102936 A1 | 4/2013 | Halsne et al. |
| 2014/0081100 A1* | 3/2014 | Muhsin ............ A61B 5/0002 600/324 |
| 2014/0277226 A1* | 9/2014 | Poore ............ A61N 1/3987 607/7 |
| 2014/0288450 A1 | 9/2014 | Freeman et al. |
| 2014/0323928 A1* | 10/2014 | Johnson ............ A61H 31/005 601/41 |
| 2015/0018695 A1 | 1/2015 | Tan et al. |
| 2015/0018823 A1 | 1/2015 | Centen |
| 2015/0094782 A1* | 4/2015 | Prew ............ A61N 1/3937 607/5 |
| 2016/0279405 A1 | 9/2016 | Riley et al. |

FOREIGN PATENT DOCUMENTS

| | | |
|---|---|---|
| GB | 2314648 A | 1/1998 |
| JP | 2001104259 A | 4/2001 |
| WO | 9724062 A1 | 7/1997 |
| WO | 9830282 A1 | 7/1998 |
| WO | 9924114 A1 | 5/1999 |
| WO | 9925306 A1 | 5/1999 |
| WO | 0027464 A2 | 5/2000 |
| WO | 0215836 A2 | 2/2002 |
| WO | 2004054656 A1 | 7/2004 |
| WO | 2005021089 A1 | 3/2005 |

* cited by examiner

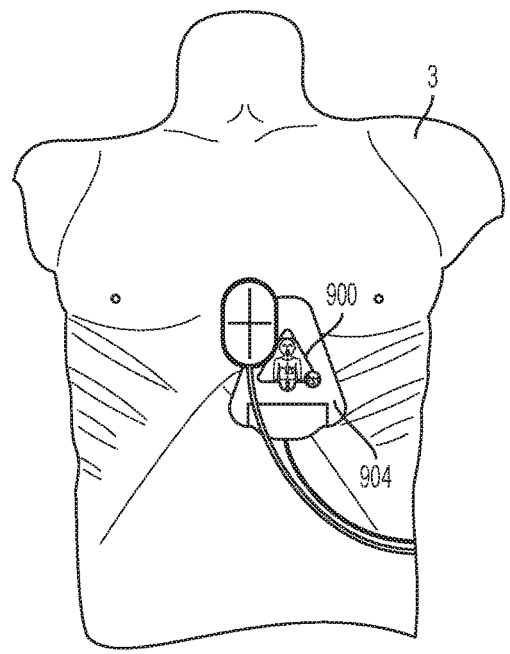
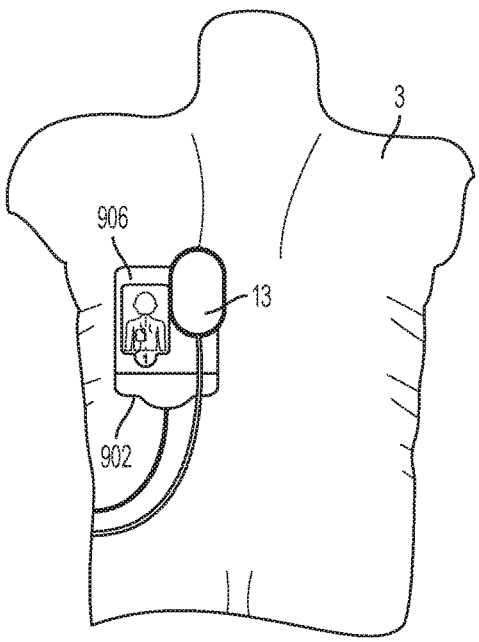
FIG. 25A  FIG. 25B
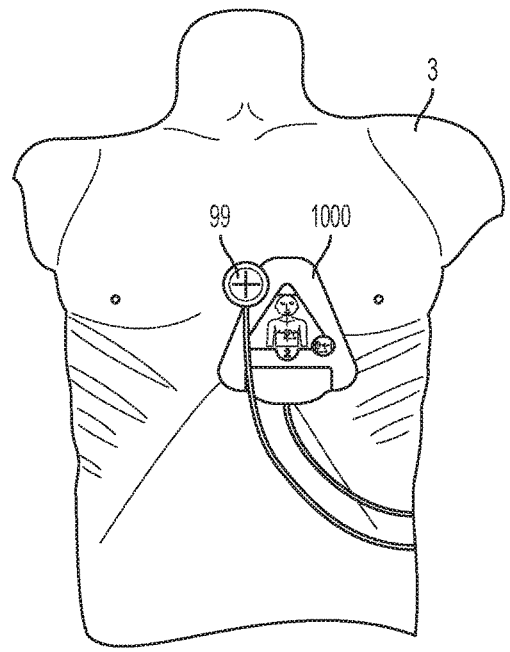
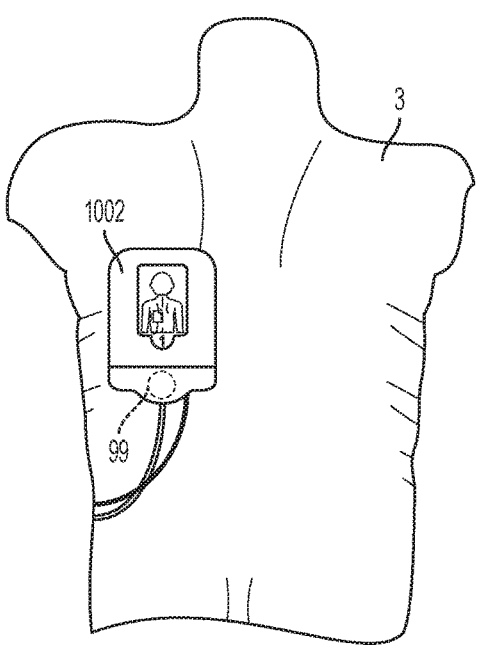
FIG. 26A  FIG. 26B

DUAL SENSOR ELECTRODES FOR PROVIDING ENHANCED RESUSCITATION FEEDBACK

CROSS REFERENCE TO RELATED APPLICATIONS

This application claims priority to U.S. Provisional Patent Application Ser. No. 62/242,749, entitled "Dual Sensor Electrodes for Providing Enhanced Resuscitation Feedback", filed Oct. 16, 2015, the entire contents of which are incorporated herein by reference.

BACKGROUND

Field

The present disclosure is related to cardiac resuscitation and, more specifically, to systems and techniques for assisting rescuers in performing cardio-pulmonary resuscitation.

Description of Related Art

Defibrillators are commonly used to treat Sudden Cardiac Arrest by applying a defibrillating shock to the heart of a cardiac arrest patient via electrodes placed on the chest of the patient. The ECG signal of a cardiac arrest patient, properly measured and analyzed, provides a strong indication of whether the patient's heart is exhibiting a shockable rhythm or a non-shockable rhythm. A shockable rhythm refers to an aberrant ECG signal where a defibrillation shock is advised for restoration of a normal heartbeat, while a non-shockable rhythm refers to an ECG signal where a defibrillation shock is not advised. Ventricular fibrillation, for example, is a shockable rhythm, while pulseless electrical activity is an example of a non-shockable rhythm. Defibrillators are also capable of treating other dysrhythmias (irregular heartbeats), such as atrial fibrillation, bradycardia, and tachycardia. An ECG signal may be obtained through electrodes placed on the chest of the patient, and the defibrillating or cardioverting shock may be applied through the same electrodes.

During resuscitation, treatment protocols recommended by the American Heart Association and European Resuscitation Council advise for the rescuer to regularly check the patient's pulse or to evaluate the patient for signs of circulation. If no pulse or signs of circulation are present, the rescuer may be often instructed to perform CPR on the victim for an appropriate period of time between shock analyses, where CPR involves applying both chest compressions and ventilations to the victim. Chest compressions and/or ventilations may be monitored during the course of CPR, for example, through systems and technologies that incorporate real-time CPR feedback (e.g., REAL CPR HELP® marketed by ZOLL® Medical Corporation) and which may implement resuscitation assemblies (e.g., CPR-D-PADZ®, CPR STAT-PADZ® marketed by ZOLL® Medical Corporation) having a sensor for obtaining CPR related information for manual CPR providers. For example, ZOLL's CPR-D-PADZ® and CPR STAT-PADZ® include a pair of electrode pads and a single chest compression sensor.

SUMMARY

According to one aspect of the present disclosure, provided is a system for facilitating resuscitation that comprises: a resuscitation assembly comprising: a first electrode assembly comprising a therapy side and a first motion sensor; a second electrode assembly comprising a therapy side and a second motion sensor; processing circuitry operatively connected to the resuscitation assembly and configured to identify the resuscitation assembly as one of a pediatric or adult resuscitation assembly based on an identification signal, receive and process signals from at least one of the first and second motion sensors to estimate at least one of a compression depth and rate (or other chest compression parameter such as release velocity) during administration of chest compressions, and receive and process signals from the first and second electrode assemblies to determine whether electrotherapy is required and adjust electrotherapy based on the identification of the resuscitation assembly as pediatric or adult; and an output device for providing one or more chest compression parameters including at least one of the estimated compression depth and the estimated compression rate for a user, wherein the output device is configured to adjust presentation of the one or more chest compression parameters based on whether the resuscitation assembly is identified as pediatric or adult.

In one example, the processing circuitry may be configured to determine a placement orientation of the first electrode assembly and the second electrode assembly on a patient. For example, the first electrode assembly may be positioned on a first portion of the patient's anatomy and the second electrode assembly may be positioned on a second portion of the patient's anatomy in an anterior-posterior orientation. In such a configuration, the first portion of the patient's anatomy may be a sternum of the patient and the second portion of the patient's anatomy may be a back of the patient. Alternatively, the first electrode assembly is positioned on a first portion of the patient's anatomy and the second electrode assembly is positioned on a second portion of the patient's anatomy in an anterior-anterior orientation such that the first electrode assembly is a sternal electrode and the second electrode assembly is an apex electrode. In such a configuration, the first portion of the patient's anatomy may be a right side of a chest of the patient between the armpit and the sternum and the second portion of the patient's anatomy may be a left side of the chest of the patient over lower ribs of the patient. In another example, the processing circuitry may be configured to adjust at least one of a displayed ECG signal and a pacing vector based on the determined placement orientation of the first electrode assembly and the second electrode assembly.

In one example, at least one of the first motion sensor and the second motion sensor is separable from the respective first or second electrode assembly. For instance, the first motion sensor may be separable from the first electrode assembly or the second motion sensor may be separable from the second electrode assembly.

In another example, the estimated chest compression depth may be calculated by subtracting a distance traveled by the second motion sensor from a distance traveled by the first motion sensor. The first motion sensor may be configured to produce a first signal representative of acceleration caused by compressions and the second motion sensor is configured to produce a second signal representative of acceleration due to movement on a compressible surface. The processing circuitry may be configured to utilize signals from the first motion sensor and the second motion sensor to determine depth of compression when an infant or neonatal patient is squeezed from both the front and back during CPR.

In one example, the resuscitation assembly may include at least one of a memory and a resistor from the identification signal is based. The processing circuitry may be configured to adjust a shock algorithm based on the identification of the resuscitation assembly as pediatric or adult. The processing circuitry may be configured to compare at least one of the estimated compression depth and the estimated compression rate to a desired range, and the output device is configured to display at least one of the estimated compression depth and the estimated compression rate and provide chest compression prompting for the user when the resuscitation assembly is identified as adult. The output device may be configured to display at least one of the estimated depth and the estimated rate without providing chest compression prompting for the user when the resuscitation assembly is identified as pediatric.

In one example, the processing circuitry and the output device may be provided in an external defibrillator. At least one of the first electrode assembly and the second electrode assembly may include a flexible electrode layer including the therapy side. In another example, at least one of the first electrode assembly and the second electrode assembly includes a sensor housing attached to the electrode layer at an attachment region. In such an example, the sensor housing may at least partially enclose the first or second motion sensor. At least a portion of the electrode layer may be constructed and arranged to deflect from the sensor housing at a location away from the attachment region such that the electrode layer substantially conforms to the patient's anatomy. The sensor housing may be laminated with the electrode layer. The sensor housing may include a padding material. In one example, the sensor housing may include a plurality of layers comprising the padding material.

The output device may be configured to provide instructions to a user for a surface upon which the patient is positioned to be changed based on information sensed from the first and second motion sensors. In one example, at least one of the first motion sensor and the second motion sensor comprises an accelerometer capable of measuring acceleration in multiple directions. In such an example, the processing circuitry may be configured to estimate a difference in orientation between the first electrode assembly and the second electrode assembly. More specifically, the processing circuitry may be configured to estimate an angle relative to a vertical axis of the patient at which a user is administering chest compressions during CPR based on the signals received from the first and second motion sensors. The output device may be configured to provide instructions to a user for administering chest compressions based on the estimation of orientation between the first and second electrode assemblies.

In another example, the processing circuitry may be configured to estimate rate of ventilations applied to the patient (e.g., from signals arising from one or more of the motion sensors, such as the anterior motion sensor). In such an example, the output device may be configured to provide instructions to a user for administering ventilations to the patient based on the estimated rate of ventilations.

In yet another example, at least one of the first electrode assembly and the second electrode assembly may include a conductive gel having an active area for electrotherapy of approximately 15-80 cm$^2$. Alternatively, at least one of the first electrode assembly and the second electrode assembly may include a conductive gel having an active area for electrotherapy of approximately 50-150 cm$^2$. At least a portion of the first electrode assembly or the second electrode assembly may be radiolucent. The resuscitation assembly may include a cable extending from at least one of the first electrode assembly and the second electrode assembly toward the processing circuitry. The cable may include the processing circuitry for estimating at least one of the compression depth and compression rate. The cable may be a substantially flat cable.

In yet another example, at least one of the first electrode assembly and the second electrode assembly may include a conductive gel having an active area for electrotherapy of approximately 15-80 cm$^2$. Alternatively, at least one of the first electrode assembly and the second electrode assembly may include a conductive gel having an active area for electrotherapy of approximately 50-150 cm$^2$. At least a portion of the first electrode assembly or the second electrode assembly may be radiolucent. The resuscitation assembly may include a cable extending from at least one of the first electrode assembly and the second electrode assembly toward the processing circuitry. The cable may include the processing circuitry for estimating at least one of the compression depth and compression rate. The cable may be a substantially flat cable.

According to another aspect of the present disclosure, provided is a system for facilitating resuscitation. The system comprises: a resuscitation assembly comprising: a first electrode assembly comprising a therapy side and a first motion sensor; a second electrode assembly comprising a therapy side and a second motion sensor; processing circuitry operatively connected to the resuscitation assembly and configured to: receive and process signals from at least one of the first and second motion sensors to estimate at least one of a compression depth and rate during administration of chest compressions, and determine a placement orientation of the first electrode assembly and the second electrode assembly on a patient; and an output device for providing guidance to a user to administer chest compressions based on the estimated chest compression depth or rate and the determined placement orientation of the first and second electrode assemblies.

According to yet another aspect of the present disclosure, provided is a system for facilitating resuscitation, comprising: a resuscitation assembly comprising: a first electrode assembly comprising a therapy side and a first motion sensor, and a second electrode assembly comprising a therapy side and a second motion sensor; processing circuitry operatively connected to the resuscitation assembly and configured to receive and process signals from at least one of the first and second motion sensors to estimate at least one of a compression depth and rate during administration of chest compressions; and an output device for providing guidance to a user to administer chest compressions based on the estimated chest compression depth or rate. At least one of the first motion sensor and the second motion sensor is separable from the respective first or second electrode assembly.

The first motion sensor may be separable from the first electrode assembly and/or the second motion sensor may be separable from the second electrode assembly. For example, the first electrode assembly or the second electrode assembly may include a pouch within which the respective first or second motion sensor is removably held. In another example, at least one of the first motion sensor and the second motion sensor is adhesively coupled to the respective first or second electrode assembly.

According to another aspect of the present disclosure, provided is a resuscitation assembly for use with a defibrillator that comprises: a flexible electrode pad having a therapy side; a sensor housing attached to the electrode pad; and a motion sensor at least partially enclosed within the sensor housing. The sensor housing has greater rigidity than the flexible electrode pad. At least a portion of the flexible electrode pad is configured to flex from the sensor housing such that the electrode pad substantially conforms to an anatomy of the patient when coupled to the patient.

The sensor housing may be coupled to the flexible electrode pad at an attachment region on the non-therapy side. In one example, the attachment region may be located in a central region of the flexible electrode pad. In another example, the attachment region may be located at least one of a central upper region and a central lower region. In still another example, the attachment region may be located along at least a portion of the periphery of the flexible electrode pad. The flexible electrode pad may be configured to flex from the sensor housing at a location away from the attachment region.

The flexible electrode pad may comprise a flexible base layer (e.g., made of a foam, thin polymeric material, electrode backing, and/or other flexible material) having a flexible electrode positioned on the therapy side. The therapy side may include a conductive material configured to provide a therapeutic treatment to the patient. The sensor housing may include a protective covering, such as a casing for the motion sensor. In one example, the sensor housing may be comprised of two or more layers. The two or more layers may be laminated to each other. In another example, the sensor housing may comprise a padded material. The sensor housing may include a plurality of layers comprising the padded material. The one or more electrode assemblies may comprise sections of differing thickness.

In one example, the motion sensor is an accelerometer, such a three-axis accelerometer. The motion sensor may be encapsulated in a polymeric material to provide protection from a surrounding environment. The sensor housing may be configured to distribute compressive forces caused by chest compressions during cardiopulmonary resuscitation (CPR) substantially evenly across the flexible electrode pad. In one example, the sensor housing may be integrated into the flexible electrode pad. In another example, the sensor housing may be adhered to the flexible electrode pad at the attachment region.

According to another aspect of the present disclosure, provided is a resuscitation assembly for use with a defibrillator that comprises: a flexible electrode pad having a therapy side configured to substantially conform to the patient's anatomy; a sensor housing coupled to the electrode pad, wherein a projected contact area between the sensor housing and the electrode pad is less than approximately 50 $cm^2$; and a motion sensor coupled with the sensor housing.

In one example, the projected contact area between the sensor housing or casing and the electrode pad may be between approximately 10-50 $cm^2$. The motion sensor may be located over a periphery of the conductive material. In another example, the motion sensor may be located over a central region of the conductive material.

The motion sensor may be a three-axis accelerometer. In one example, the motion sensor may be encapsulated in a casing or covering that includes a suitable material such as a polymeric material to provide protection from a surrounding environment. In another example, the motion sensor may be at least partially enclosed within the sensor housing. The sensor housing may have a greater rigidity than the flexible electrode pad. At least a portion of the flexible electrode pad may be configured to flex from the sensor housing such that the electrode pad substantially conforms to an anatomy of the patient when coupled to the patient.

According to still another aspect of the present disclosure, provided is a resuscitation assembly for use with a defibrillator that comprises two or more electrode assemblies. Each electrode assembly comprises: a flexible electrode pad that comprises a therapy side and a non-therapy side; and a motion sensor within a sensor housing that is coupled to the flexible electrode pad. At least a portion of the flexible electrode pad is configured to substantially conform to an anatomy of a patient when placed on the patient. The two or more electrode assemblies are coupled to each other.

For at least one of the electrode assemblies, the sensor housing may be more rigid than the flexible electrode pad. In addition, for at least one of the electrode assemblies, the sensor housing may be coupled to the flexible electrode pad at an attachment region on the non-therapy side. In one example, the attachment region may be located at a central region of the flexible electrode pad. The sensor housing may be adhered to the flexible electrode pad at the attachment region.

For at least one of the electrode assemblies, the sensor housing may include a protective covering or casing for the motion sensor. In one example, for at least one of the electrode assemblies, the sensor housing may comprise a padded material. For at least one of the electrode assemblies, the motion sensor may include an accelerometer. In another example, for at least one of the electrode assemblies, the sensor housing may be integrated with the flexible electrode pad.

According to another aspect of the present disclosure, provided is a system for facilitating resuscitation that comprises: a first electrode assembly comprising a therapy side a first motion; a second electrode assembly comprising a therapy side and a second motion sensor; processing circuitry operatively connected to and programmed to receive and process signals from the first and second motion sensors; and an output device for providing instructions to a user for a surface upon which the patient is positioned to be changed based on information sensed from the first and second motion sensors.

In one example, the first motion sensor may be configured to produce a first signal representative of acceleration caused by compressions and the second motion sensor may be configured to produce a second signal representative of acceleration due to movement on a compressible surface. A chest compression depth may be calculated by subtracting the second signal representative of acceleration caused by movement on a compressible surface from the first signal representative of acceleration due to compression.

In one example, the first electrode assembly is positioned on a first portion of the patient's anatomy and the second electrode assembly is positioned on a second portion of the patient's anatomy in an anterior-posterior orientation. In such an example, the first portion of the patient's anatomy may be a sternum of the patient and the second portion of the patient's anatomy may be a back of the patient. Alternatively, the first electrode assembly and the second electrode assembly may be configured to be positioned on the patient in an anterior-anterior orientation. The processing circuitry and the output device may be provided in an external defibrillator.

According to still another aspect of the present disclosure, provided is a system for facilitating resuscitation that comprises: a first electrode assembly comprising a therapy side and a first motion sensor; a second electrode assembly comprising a therapy side and a second motion sensor, wherein at least one of the first motion sensor and the second motion sensor comprises an accelerometer capable of measuring acceleration in multiple directions; processing circuitry operatively connected to and programmed to receive and process signals from the first and second motion sensors to estimate a difference in orientation between the first electrode assembly and the second electrode assembly; and an output device for providing instructions to a user for administering chest compressions based on the estimation of orientation between the first and second electrode assemblies.

In one example, the processing circuitry may be configured to estimate at least one of a chest compression depth and rate (and/or other parameter such as release velocity) during administration of chest compressions and to compare the chest compression depth or rate (or other parameter such as release velocity) to a desired range based on the received signals from the first and second motion sensors. The output device may be configured to provide instructions to a user for a surface upon which the patient is positioned to be changed based on information sensed from the first and second motion sensors. The processing circuitry may be configured to estimate an angle relative to a vertical axis of the patient at which a user is administering chest compressions during CPR based on the signals received from the first and second motion sensors.

In one example, the output device may be configured to provide instructions to a user for administering chest compressions based on the estimation of orientation between the first and second electrode assemblies. In another example, the processing circuitry may be configured to estimate rate of ventilations applied to the patient. In such an example, the output device may be configured to provide instructions to a user for administering ventilations to the patient based on the estimated rate of ventilations.

According to another aspect of the present disclosure provided is a system for facilitating resuscitation that comprises: a resuscitation assembly configured for use with patients weighing less than 55 lbs; processing circuitry; and an output device. The resuscitation assembly comprises: a first electrode assembly comprising a therapy side and a first motion sensor, the therapy side of the first electrode assembly including a first conductive gel having an active area for electrotherapy of approximately 15-80 cm$^2$; and a second electrode assembly comprising a therapy side and a second motion sensor, the therapy side of the second electrode assembly including a second conductive gel having an active area for electrotherapy of approximately 15-80 cm$^2$. The processing circuitry is operatively connected to the resuscitation assembly and is configured to receive and process signals from the first and second motion sensors to estimate at least one of a compression depth and rate during administration of chest compressions. The output device is for providing guidance to a user to administer chest compressions based on the estimated chest compression depth or rate.

In some examples, at least one of the first motion sensor and the second motion sensor may be separable from the respective first or second electrode assembly. The processing circuitry may be configured to identify the resuscitation assembly as one of a pediatric or adult resuscitation assembly based on an identification signal. The processing circuitry may be configured to determine a placement orientation of the first electrode assembly and the second electrode assembly on a patient. The chest compression depth may be calculated by subtracting a distance traveled by the second motion sensor from a distance traveled by the first motion sensor. The first motion sensor may be configured to produce a first signal representative of acceleration caused by compressions and the second motion sensor is configured to produce a second signal representative of acceleration due to movement on a compressible surface. The processing circuitry may be configured to utilize signals from the first motion sensor and the second motion sensor to determine depth of compression when an infant or neonatal patient is squeezed from both the front and back during CPR.

The processing circuitry and the output device may be provided in an external defibrillator. At least one of the first electrode assembly and the second electrode assembly may include a flexible electrode layer including the therapy side. The output device may be configured to provide instructions to a user for a surface upon which the patient is positioned to be changed based on information sensed from the first and second motion sensors. At least one of the first motion sensor and the second motion sensor may comprise an accelerometer capable of measuring acceleration in multiple directions. The processing circuitry may be configured to estimate a difference in orientation between the first electrode assembly and the second electrode assembly. The processing circuitry may also be configured to estimate an angle relative to a vertical axis of the patient at which a user is administering chest compressions during CPR based on the signals received from the first and second motion sensors. The output device may be configured to provide instructions to a user for administering chest compressions based on the estimation of orientation between the first and second electrode assemblies.

According to another aspect of the present disclosure, provided is a system for facilitating resuscitation that comprises a resuscitation assembly configured for use with patients weighing more than 55 lbs, processing circuitry, and an output device. The resuscitation assembly comprises: a first electrode assembly comprising a therapy side and a first motion sensor, the therapy side of the first electrode assembly including a first conductive gel having an active area for electrotherapy of 50-150 cm$^2$; a second electrode assembly comprising a therapy side and a second motion sensor, the therapy side of the second electrode assembly including a second conductive gel having an active area for electrotherapy of 50-150 cm$^2$. The processing circuitry is operatively connected to the resuscitation assembly and is configured to receive and process signals from the first and second motion sensors to estimate at least one of a compression depth and rate during administration of chest compressions. The output device is for providing guidance to a user to administer chest compressions based on the estimated chest compression depth or rate.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

BRIEF DESCRIPTION OF THE DRAWINGS

FIGS. 25A and 25B illustrate placement of an example of a resuscitation assembly in accordance with the present disclosure on a cardiac arrest victim;

FIGS. 26A and 26B illustrate placement of an example of a resuscitation assembly in accordance with the present disclosure on a cardiac arrest victim.

DETAILED DESCRIPTION

The present disclosure relates to resuscitation assemblies and systems thereof that may be used for a wide variety of patients in need of resuscitation, such as for small (e.g., pediatric, infant) or large (e.g., adult) patients. In various embodiments, the resuscitation assemblies may include at least a pair of electrode assemblies, where each electrode assembly includes an electrode pad and a motion sensor. Though, for some embodiments, a resuscitation assembly may include a single electrode assembly, having an electrode pad and an associated motion sensor, or multiple electrode assemblies, having an electrode pad and an associated motion sensor.

Resuscitation assemblies and systems described herein may provide for improved resuscitation over prior devices and methods, for example, by providing improved accuracy, detection and/or correction in determining resuscitation related parameters, such as chest compression depth, release velocity, angle of chest compressions, the presence of an error-inducing surface (e.g., compressible surface under patient, such as a soft mattress, etc.), chest compression rate and/or timing, ventilation rate, etc. Systems and resuscitation assemblies in accordance with the present disclosure provide improved accuracy in determining chest compression depth than previously possible, for example, by detecting and/or correcting for errors in resuscitation parameters as a result of external sources, e.g. error-inducing surface, patient is in transport (e.g., traveling on a gurney/stretcher or within an ambulance), etc. Accordingly, such systems may advantageously provide improved feedback on whether chest compressions are appropriately applied and/or whether the rescuer needs to correct for error from an external source (e.g. change the surface on which the patient is placed, reduce other motion induced error, etc.).

Figure 1A:
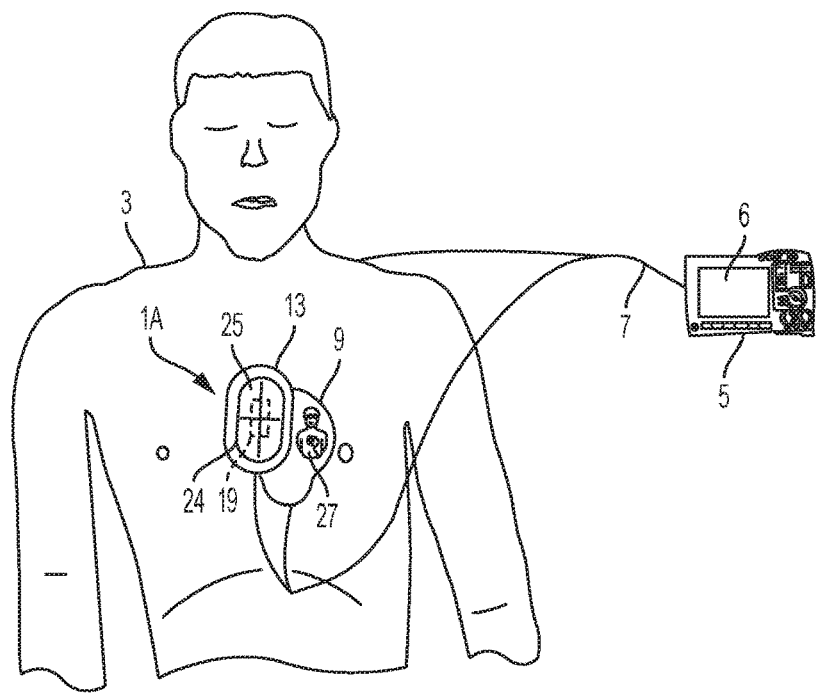
FIGS. 1A and 1B illustrate placement of an example of a resuscitation assembly in accordance with the present disclosure on a cardiac arrest victim.
Figure 1B:
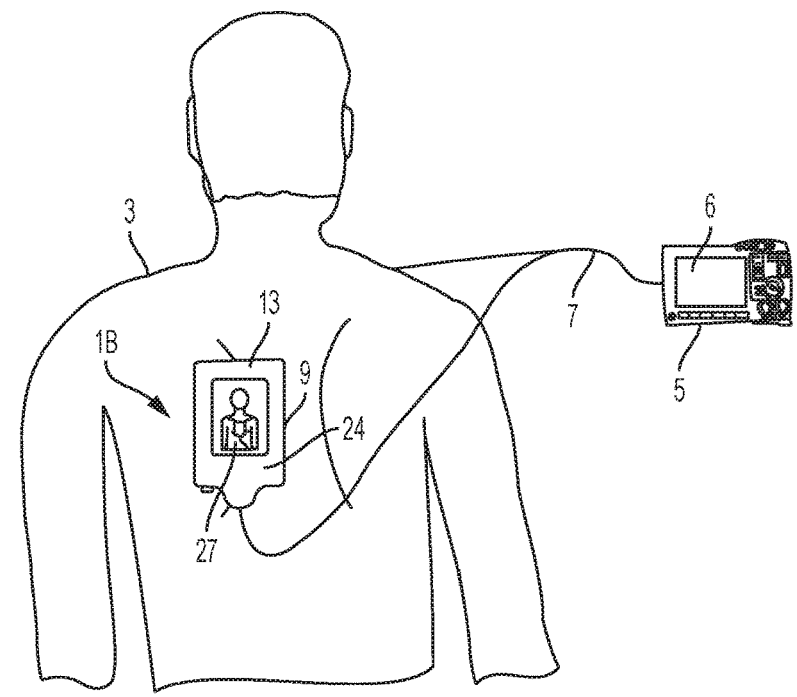
Figure 12:
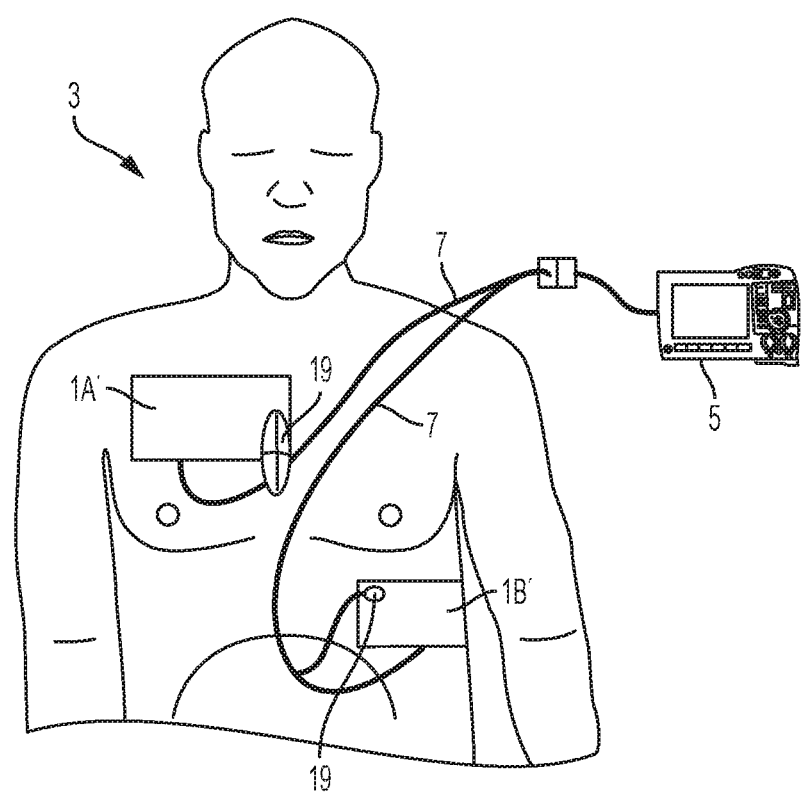
FIG. 12 illustrates an alternative placement of another example of a resuscitation assembly on a victim in accordance with some embodiments.
Figure 19:
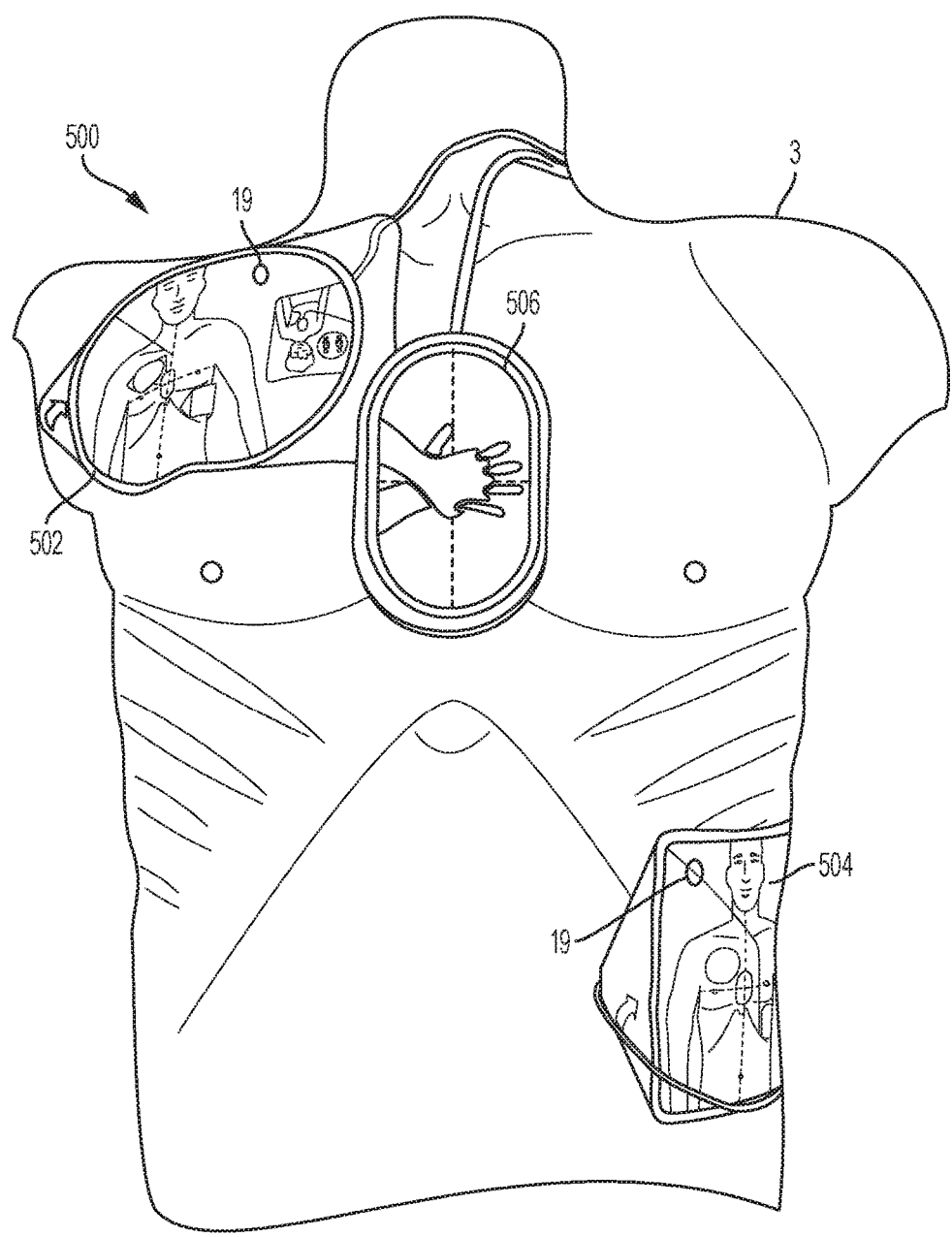
FIG. 19 illustrate placement of an example of a resuscitation assembly in accordance with the present disclosure on a cardiac arrest victim.

In certain examples, as illustrated in FIGS. 1A-1B, the resuscitation assemblies of this disclosure comprise two electrode assemblies, each comprising an electrode pad and one or more chest compression sensors. One electrode assembly may be placed at an anterior position (e.g., over the sternum) of the patient and a second electrode assembly may be placed on a posterior position (e.g., on the back, opposite the anterior placed electrode) of the patient, i.e., in an A-P position. Alternatively, as illustrated in FIGS. 12 and 19, a first electrode assembly may be placed on an anterior position of the patient and a second resuscitation electrode assembly may be placed on a side position of the patient, i.e., in an A-A position. In such a context, it may be advantageous to be able to track the movement of each of the electrode assemblies while coupled to the patient. According to various embodiments, resuscitation assemblies described herein may be intended for use only in the A-P position, only in the A-A position, in either A-A or A-P position, and/or in a different position, such as a lateral-lateral position (not shown in the figures) where the electrode assemblies are placed on each side of the patient.

As described herein, each electrode assembly placed on the patient may incorporate one or more chest compression sensors, for example motion sensors (e.g. accelerometers, velocity sensors, ultrasonic sensors, infrared sensors, other sensors for detecting displacement). In certain examples, the motion sensors may be single axis or multiple axis accelerometers. Single axis accelerometers may be used to determine chest compression parameters (e.g. depth, rate, velocity, timing, etc.) by measuring and/or providing signals that assist in determining acceleration, velocity and/or displacement. Multi-axis accelerometers, e.g. a three-axis accelerometers, may be able to provide signals that further determine relative orientation of their respective electrode assemblies by measuring parameters indicative of motion along each axis, in addition to determining chest compression parameters. The motion sensor may also include a gyroscope for determining orientation of the sensor (and, in some cases, the electrode assembly) by way of tilt or rotation. In additional examples, two or more accelerometers may be arranged orthogonally with respect to each other, to determine electrode and/or chest acceleration in multiple orthogonal axes. Generally speaking, while an accelerometer senses acceleration or gravity, motion or displacement of the accelerometer can be determined through a series of calculations (e.g., double integration, etc.) known to those of skill in the art.

By incorporating motion sensors in both electrode assemblies, resuscitation related parameters may be more accurately determined than would otherwise be the case if only one electrode assembly incorporated a motion sensor. For instance, the electrode assemblies may serve as reference points for one another, based on their respective displacement and orientation. Accordingly, the manner in which the electrode assemblies (e.g., electrode pads) are placed and/or how they move relative to one another may inform the type of instructions output to a rescuer. As an example, discussed further below, based on their orientation and/or distance relative to one another, it can be determined whether the electrode assemblies are placed in an A-A or A-P position, or not in any typical position at all, such as a lateral-lateral position where the electrode assemblies are placed on either side of the patient. In addition, based on the pattern of movement of both electrode assemblies, the type of surface on which the patient resides can be determined, the angle with respect to the vertical axis (when the patient is lying down) at which chest compressions are being administered can also be estimated, or the direction normal to the patient when the patient is lying down on a slanted surface.

As also provided herein, the electrode assemblies may be constructed to suitably conform to the patient's body. For example, an electrode assembly may comprise a sensor housing (e.g., containing one or more motion sensors, casing, protective and/or padding material) and a flexible electrode pad, where the sensor housing is more rigid than the flexible electrode pad. The sensor housing may be coupled with the flexible electrode pad in a manner that allows the electrode pad to maintain its flexibility, thus allowing it to conform to the patient's body. For example, the sensor housing may be attached to the electrode pad at a portion of the electrode pad, allowing another portion of the electrode pad (the portion of the assembly that is used to sense ECG and deliver the therapeutic shock) to retain its flexibility in order to conform to the patient's anatomy.

Figure 2A:
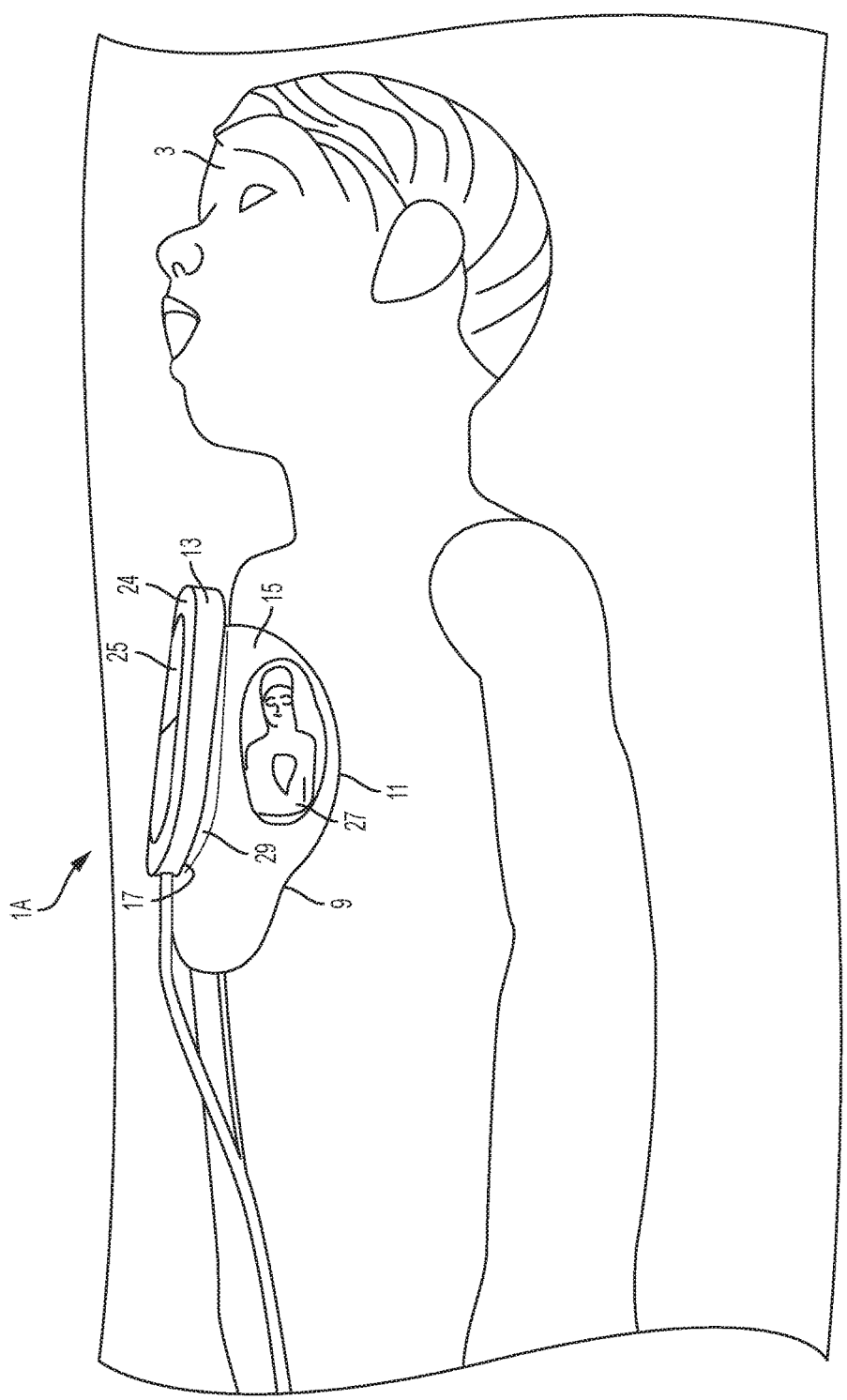
FIGS. 2A and 2B are side views that illustrate placement of a resuscitation assembly.
Figure 2B:
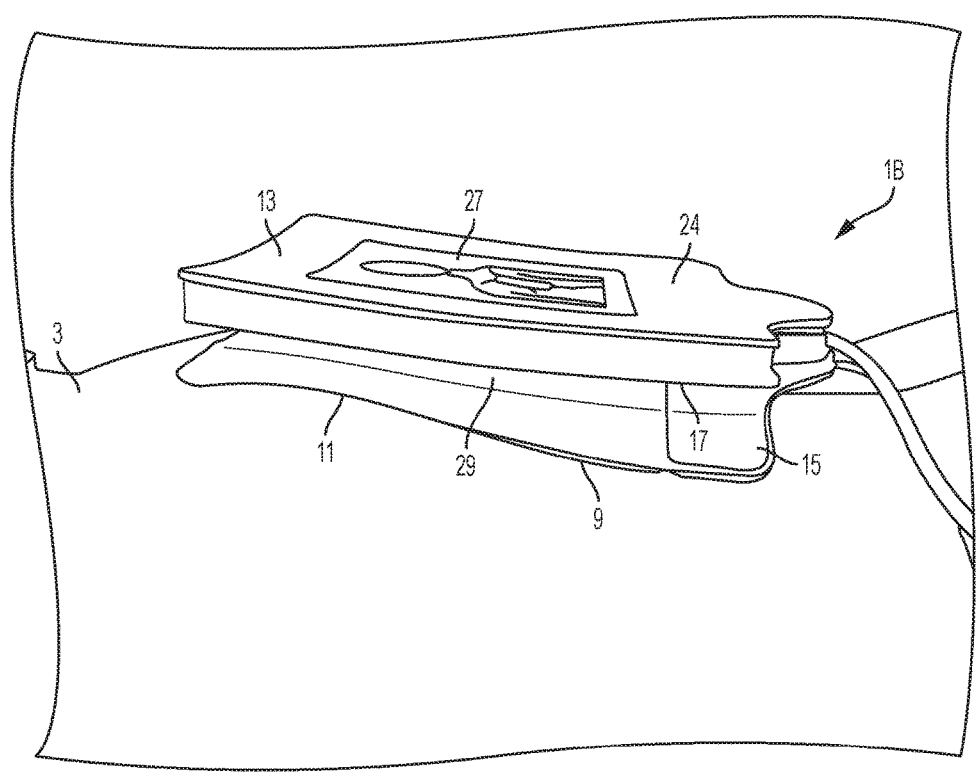
Figure 3:
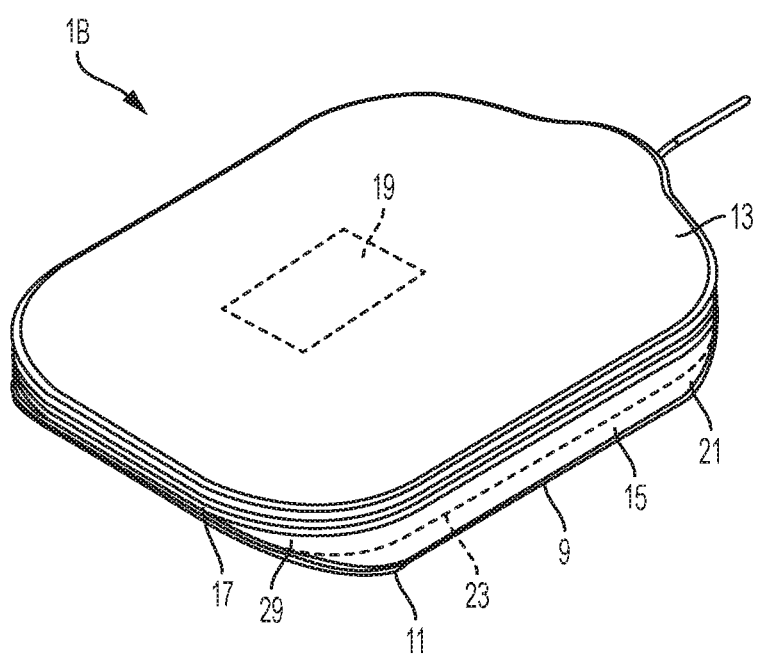
FIG. 3 is a perspective view of an electrode assembly of a resuscitation assembly in accordance with an embodiment.
Figure 4:
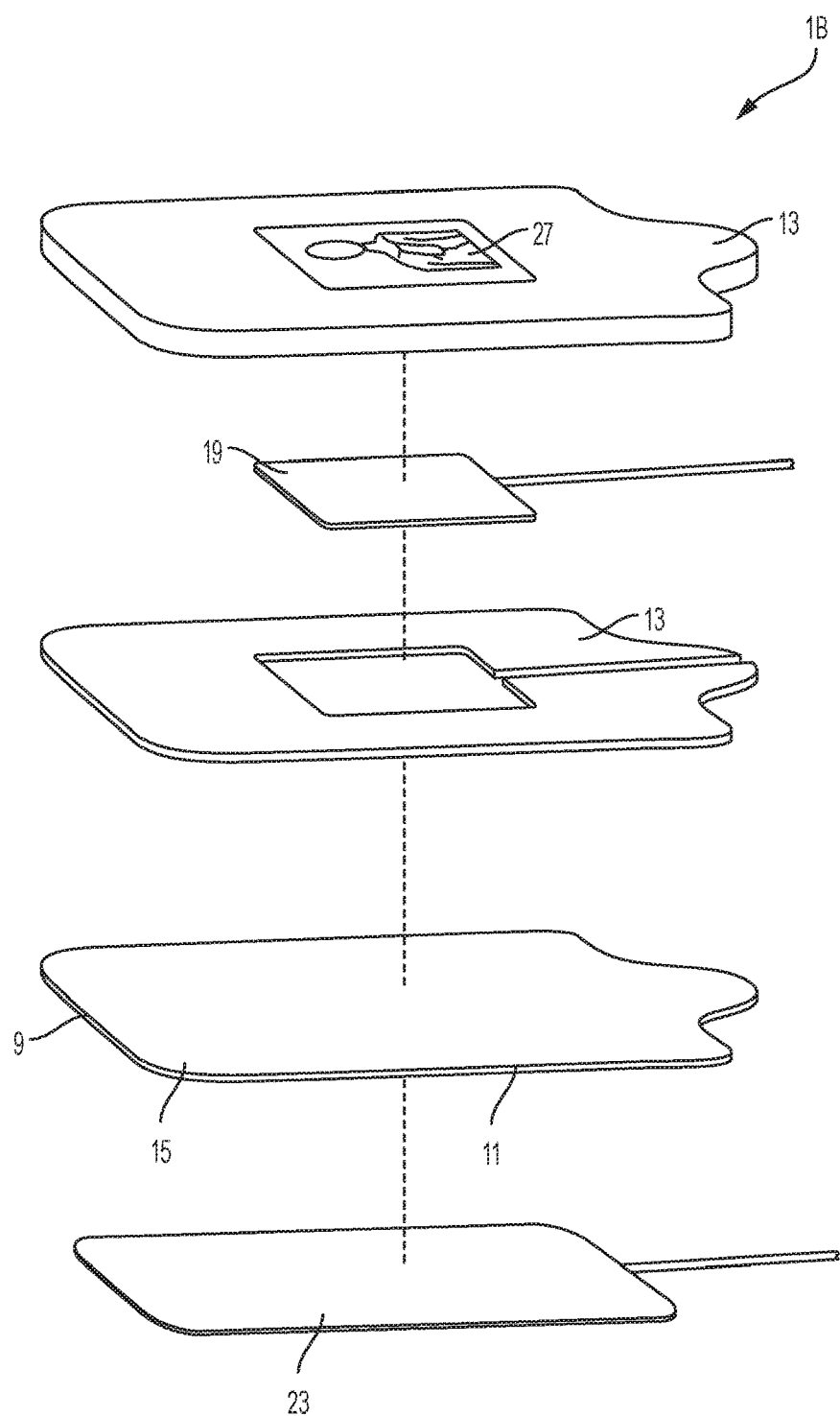
FIG. 4 is an exploded view of the electrode assembly of the resuscitation assembly of FIG. 1B.
Figure 7:
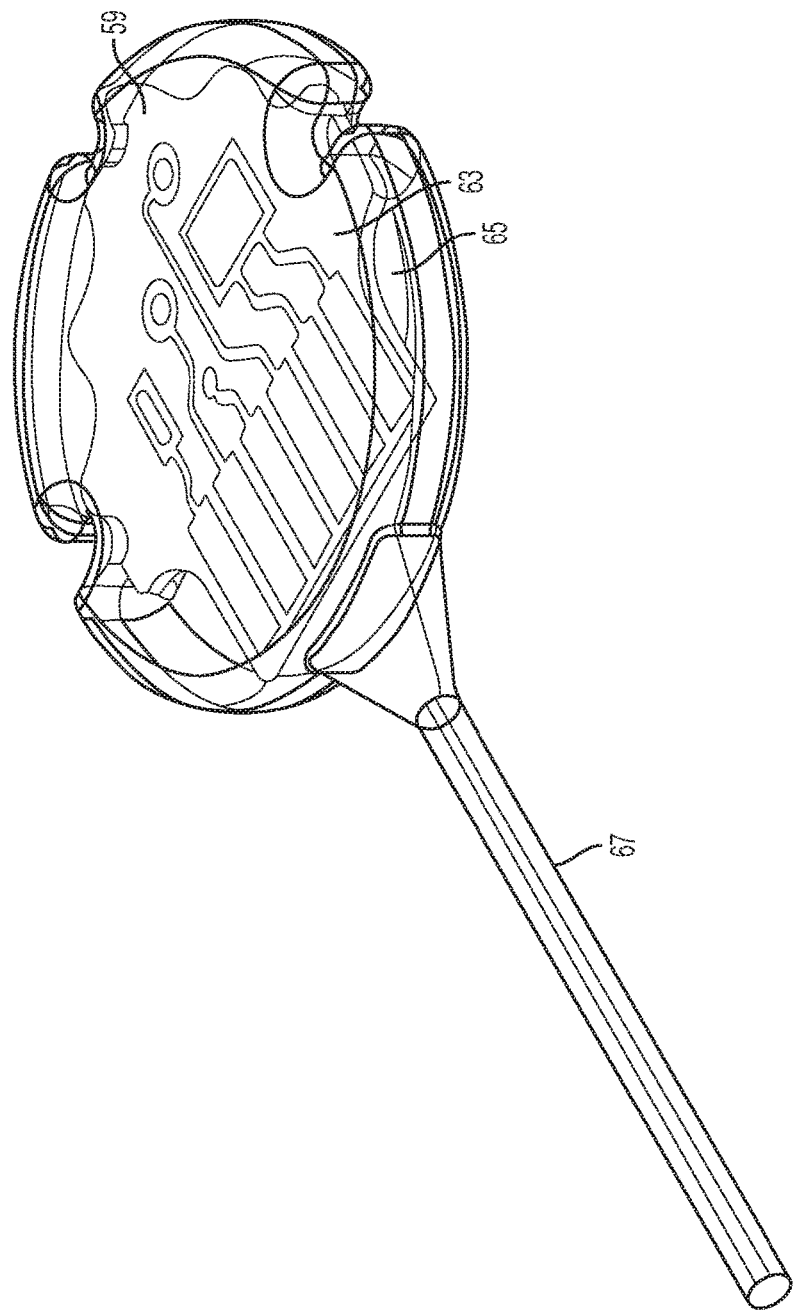
FIG. 7 is a perspective view of a sensor assembly for use with resuscitation assemblies in accordance with various embodiments.
Figure 10:
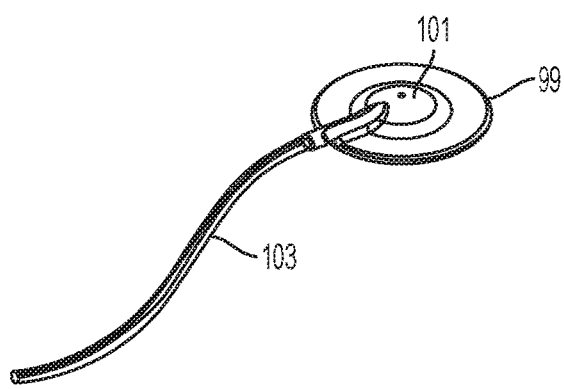
FIG. 10 is a perspective view of a sensor assembly for use with the electrode assembly of FIG. 9.

In some embodiments, the sensor housing includes padding material and/or protective covering that surrounds the motion sensor. For example, as shown in FIGS. 2B, 3, 4 and others, the motion sensor may be integrated into a portion of the padding (e.g., motion sensor may be contained within an upper padding portion which does not include the conductive therapeutic material of the electrode pad) of the electrode assembly. Though, for certain embodiments, the sensor housing does not include padding material. For example, as illustrated in FIGS. 7 and 10, the sensor housing may include a protective covering (e.g., plastic/polymeric encasement), separate from a larger padding material. That is, the motion sensor may be provided as part of an electrode assembly and coupled (e.g., wired, wirelessly) to an overall resuscitation system, associated with an appropriate electrode pad, yet is separate or is otherwise able to be positioned independently from the electrode pad. It can also be appreciated that a sensor housing may include both a protective covering (e.g., polymeric/plastic encasement/casing), within which a motion sensor is disposed, and a larger padding material, within which the protective covering is further disposed.

Figure 1C:
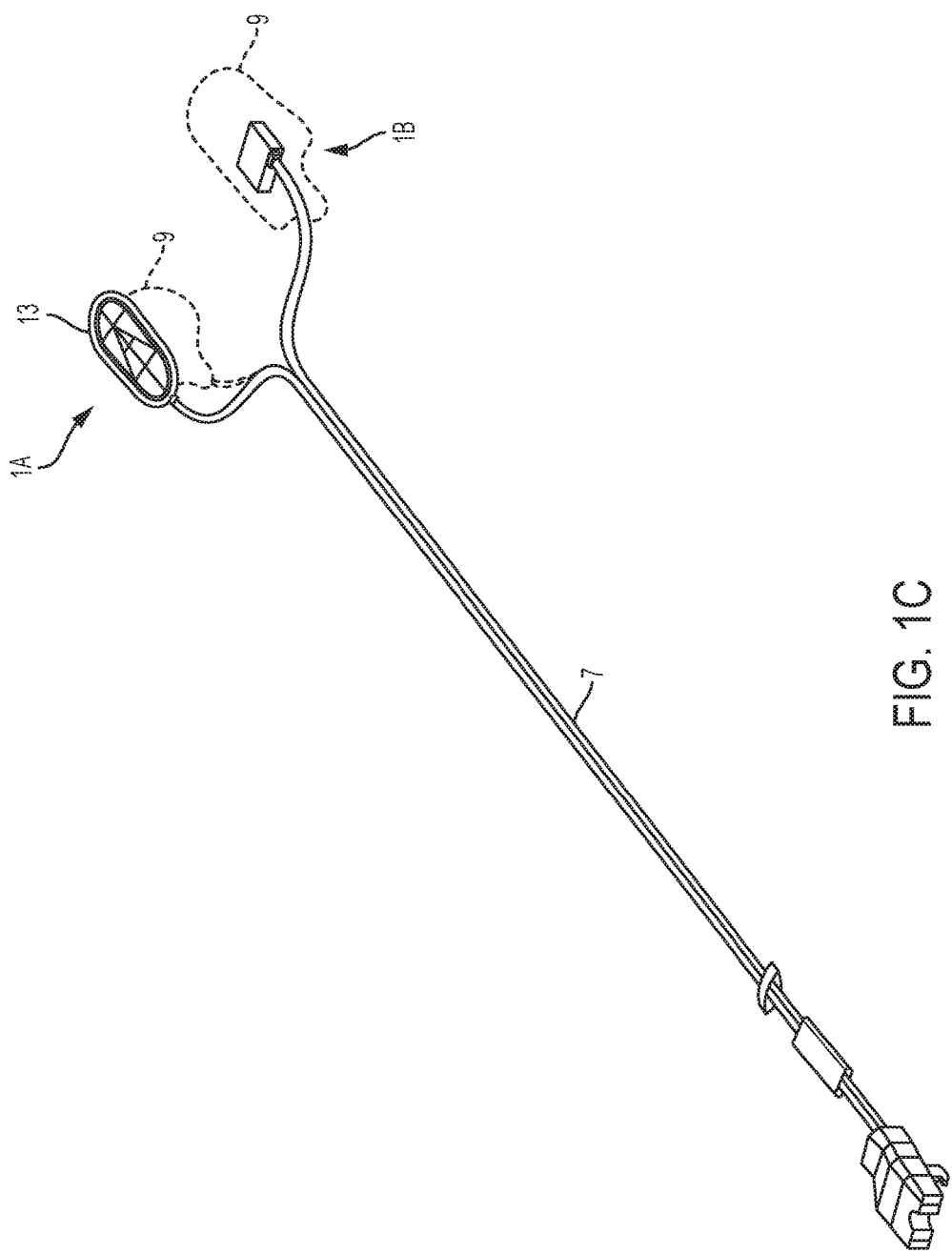
FIG. 1C is a perspective view of the resuscitation assembly of FIGS. 1A and 1B.

FIGS. 1A-1C describe a resuscitation assembly of the present disclosure, comprising a pair of electrode assemblies, denoted generally as reference numerals 1A and 1B, in accordance with the present disclosure that are placed on a patient 3. The patient 3 is shown with the two electrode assemblies 1A, 1B secured to the chest and back, respectively, of the patient 3 in an anterior-posterior (A-P) configuration. While the electrode assemblies shown in FIGS. 1A and 1B are shown as being attached to a patient in an A-P configuration, this is not to be construed as limiting the present disclosure as the electrode assemblies may also be attached to the patient according to other configurations, such as in an anterior-anterior (A-A) configuration as shown in FIG. 12 and discussed in greater detail hereinafter.

The resuscitation assembly of FIGS. 1A and 1B is operatively connected to a defibrillator 5, such as a ZOLL Medical R Series or X Series Monitor Defibrillator, which can operate as an AED, a semi-automatic defibrillator (SAD), and/or a manual defibrillator with a monitor, and can also be used for cardioverting and pacing (where electrical pulses are delivered through the patient's chest according to a vector at least partially determined by placement of the pads, so as to stimulate the heart to contract), through cables 7. However, this is not to be construed as limiting the present disclosure as the resuscitation assembly of the present disclosure may be used with any suitable defibrillator system. The defibrillator 5 is operable to generate a defibrillating shock and deliver that shock to the patient through the electrode assemblies 1A, 1B. In one example, the defibrillator 5 can include an ECG monitor and display for analyzing the ECG signals obtained through the electrode pad and displaying the ECG waveform to a user. The display can also provide the user with feedback regarding chest compressions as disclosed in U.S. patent Ser. No. 14/499,617, entitled "Defibrillator Display," assigned to the assignee of the present application, and which is hereby incorporated by reference in its entirety.

With reference to FIGS. 1A-4, the resuscitation assembly includes two (or more) electrode assemblies that each may include a flexible electrode pad 9 having a therapy side 11 configured to be coupled to the patient 3, a sensor housing 13 attached to a side 15 of the electrode pad 9 opposite the therapy side 11 at an attachment region 17, and a motion sensor 19 enclosed within the sensor housing 13. In various embodiments, it may be preferable for a motion sensor to be embedded within a sensor housing so that the sensor (and associated casing) is protected from being damaged and is securely held by the electrode assembly so as not to be subject to undesirable movement within the housing. While not expressly shown in the figures, the sensor housing 13 may include both a padding material and an optional protective casing for the motion sensor 19.

Figure 6:
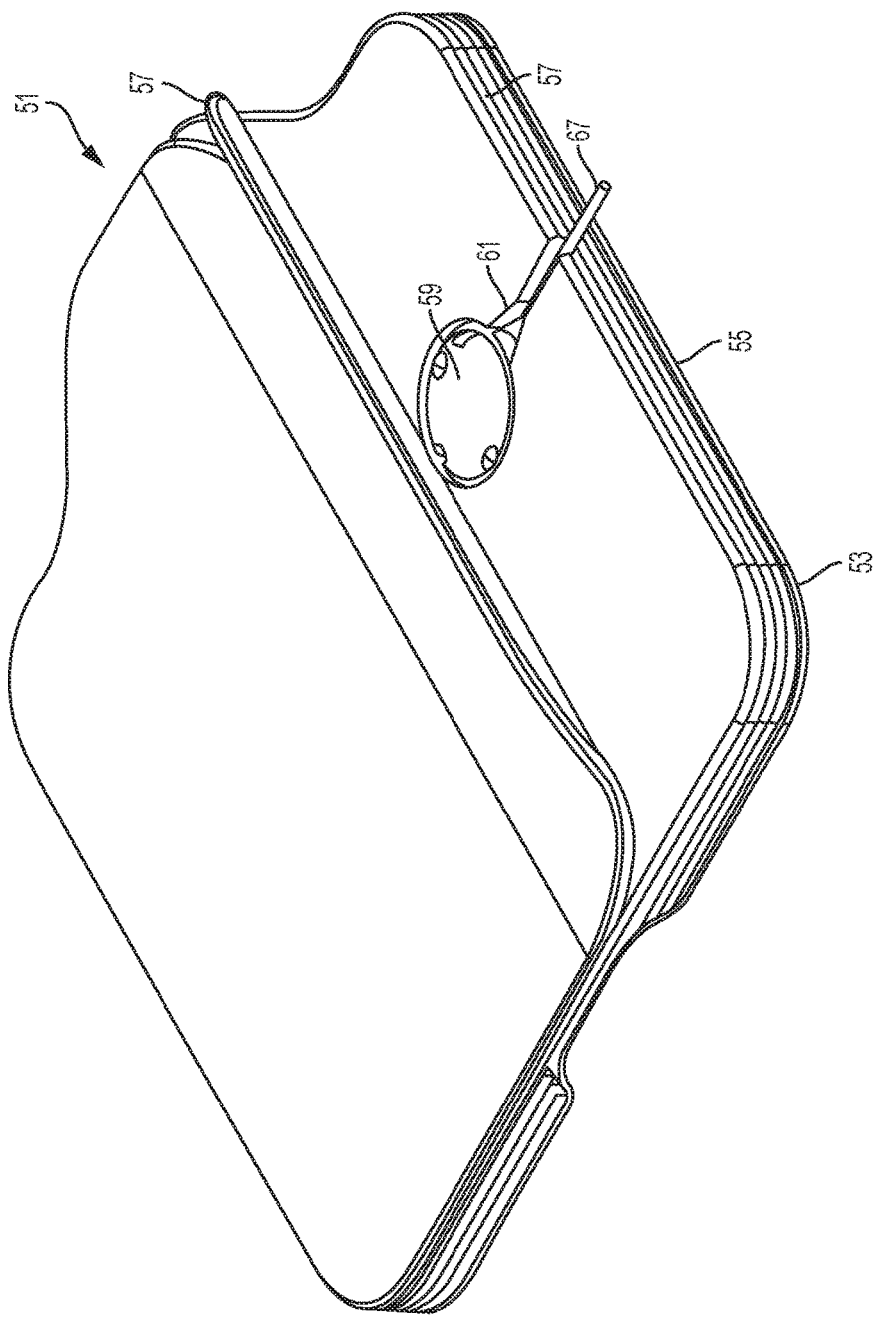
FIG. 6 is a perspective view of an electrode assembly of FIG. 3 with a layer partially removed.

While the motion sensor 19 is illustrated in FIGS. 3-4 as being completely enclosed within the padding material of sensor housing 13, this is not to be construed as limiting the present disclosure as the motion sensor 19 (and its respective encasement) may be only partially enclosed within the padding of the sensor housing 13. For example, motion sensor 19 and encasement may be at least partially exposed, such as in the embodiment shown in FIG. 6. In such examples, the motion sensor and encasement may be constructed to be removable, repositioned and/or replaced.

Figure 2C:
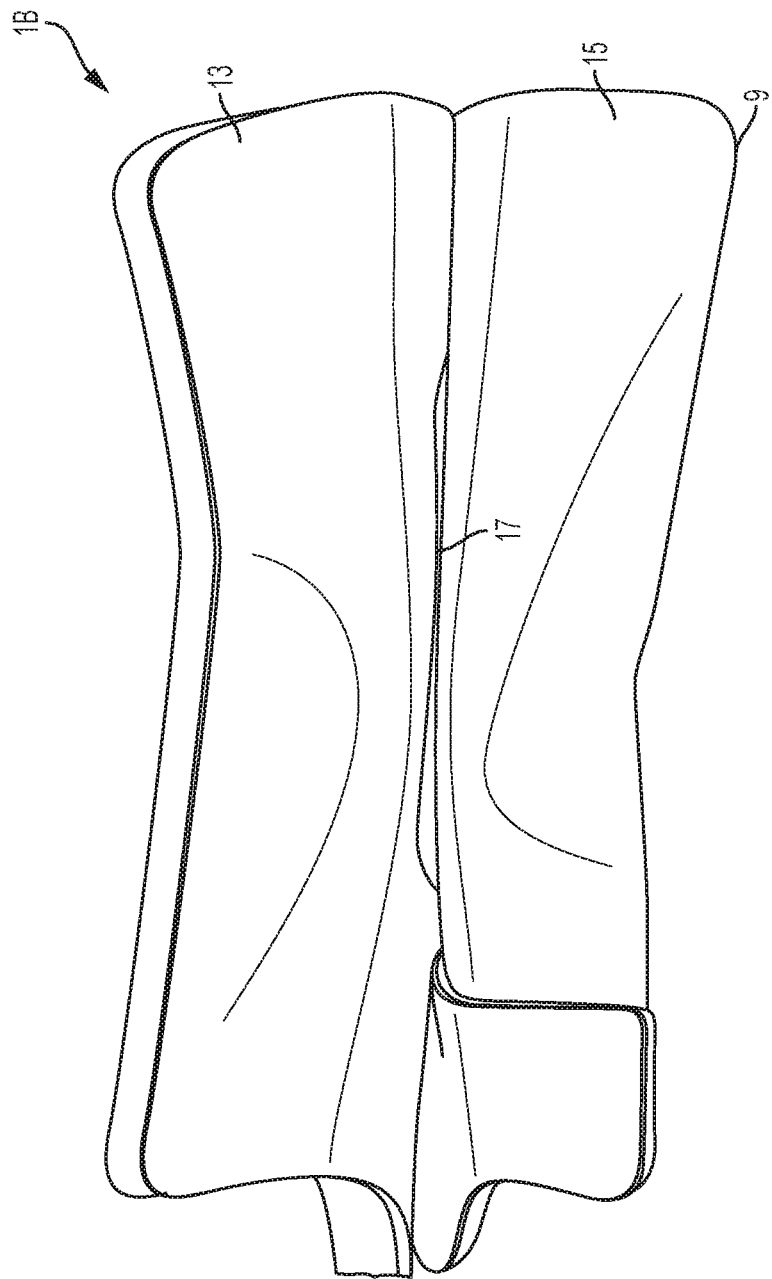
FIG. 2C is a side view of an electrode assembly of the resuscitation assembly of FIG. 1B.

As provided herein, and shown in FIG. 2C, the flexible electrode pad 9 may be attached to a comparatively more rigid sensor housing 13 at an attachment region 17 which spans only a fraction of the area of contact there between. That is, the area of attachment between the flexible electrode pad 9 and the sensor housing 13 may extend only partially across the surface of the electrode pad 9, allowing the portion of the electrode pad 9 that remains unattached to remain flexible and conform to the patient's body. Accordingly, by allowing the portion of the electrode pad 9 that remains unattached to the sensor housing 13 to deflect or otherwise flex back and forth, the sensor housing 13 does not undesirably force the electrode pad 9 to peel away from the patient's body.

The electrode pad 9 and sensor housing 13 may be attached by any suitable method, for example, at the point of attachment, the electrode pad and the housing may be formed of the same material (e.g., foam padding), mechanically coupled (e.g., interlocking), stapled, sutured, stitched, non-adhesively coupled, adhesively coupled, or otherwise adhered. For example, as shown in FIG. 2C, the sensor housing 13 and the electrode pad 9 are directly attached to one another. Accordingly, particularly for small (pediatric, undersized) patients or those suffering from conditions (e.g. kyphosis) that may warrant such a configuration, the flexible electrode pad 9 may be better suited to conform to the surface contours of the patient's body than may be the case if the electrode pad 9 and sensor housing 13 are attached along the entire surface of contact there between (e.g., having a completely flush attachment between the non-therapy side of the electrode pad and the padding material of the sensor housing). Otherwise, as discussed above, without such a construction, or similar arrangement thereof, there may be a greater tendency for the entire assembly to lift off from the patient's body. Though, as described further herein, it can be appreciated that for some embodiments, the electrode pad and motion sensor (along with sensor housing and/or sensor casing) are not required to be directly attached to one another.

The flexible electrode pad 9 may be any type of electrode suitable for use in defibrillation, and generally includes a conductor, such as tin, silver, AgCl or any other suitable conductive material, provided at the therapy side 11; a conductive electrolyte gel (e.g., solid, adhesive polymer), such as a hydrogel; and lead wires to connect the conductor to the cable 7. In various illustrative embodiments, for pediatric electrodes, the gel has an active (electrotherapy) area of at least approximately 15 $cm^2$ (e.g., approximately 15-30 $cm^2$, approximately 15-40 $cm^2$, approximately 15-50 $cm^2$, approximately 15-60 $cm^2$, approximately 15-70 $cm^2$, approximately 15-80 $cm^2$, approximately 15-90 $cm^2$, approximately 15-100 $cm^2$, approximately 20-40 $cm^2$, approximately 20-50 $cm^2$, approximately 20-60 $cm^2$, approximately 20-70 $cm^2$, 3 approximately 0-50 $cm^2$, approximately 30-60 $cm^2$, approximately 30-70 $cm^2$) for each electrode with a combined total area for both electrodes of at least approximately 45 $cm^2$ (e.g., approximately 45-60 $cm^2$, approximately 45-70 $cm^2$, approximately 45-80 $cm^2$, approximately 45-90 $cm^2$, approximately 45-100 $cm^2$, approximately 45-120 $cm^2$, approximately 45-150 $cm^2$). As an example, an anterior pediatric electrode may have a conductive gel therapy area of at least approximately 15 $cm^2$ (e.g., approximately 5.5" max length, approximately 4.5" max width), and a posterior pediatric electrode may have a conductive gel therapy area of at least approximately 15 $cm^2$ (e.g., approximately 5.75" max length, approximately 3.5" max width). As another example, an anterior pediatric electrode may have a conductive gel therapy area of approximately 40 $cm^2$ (e.g., approximately 32 cm length, approximately 27 cm width), and a posterior pediatric electrode may have a conductive gel therapy area of approximately 50 $cm^2$ (e.g., approximately 36 cm length, approximately 22 cm width). In other illustrative embodiments, for adult electrodes, the gel has an active (electrotherapy) area of at least approximately 50 $cm^2$ (e.g., approximately 50-80 $cm^2$, approximately 50-90 $cm^2$, approximately 50-100 $cm^2$, 50-110 $cm^2$, approximately 50-120 $cm^2$, approximately 50-130 $cm^2$, approximately 50-140 $cm^2$, approximately 50-150 $cm^2$) for each electrode with a combined total area of at least approximately 150 $cm^2$ (e.g., approximately 150-200 $cm^2$, approximately 150-250 $cm^2$, approximately 150-300 $cm^2$). As an example, an anterior adult electrode may have a conductive gel therapy area of approximately 80 $cm^2$, and a posterior adult electrode may have a conductive gel therapy area of approximately 115 $cm^2$. The above described dimensions and measurements qualified by the term approximately include the specified dimension and/or measurement taking into account limits of measurement and typical sources of error.

The flexible electrode pads 9 of electrode assemblies 1A, 1B may be similar in their layered construction, although as illustrated, the lateral shapes of the pads may vary depending on where the pads are to be placed on the patient. For instance, the electrode pad of resuscitation electrode assembly 1A is shown to have rounded edges, providing for relatively easy placement on the chest area of a patient's thorax, while the electrode pad of electrode assembly 1B is shown to be rectangular, providing for more intuitive alignment with the spine on the back area of the patient's thorax than would otherwise be the case for other shapes. In addition, in various embodiments, electrode assemblies described herein may be made from radiolucent and/or radiotransparent materials, and thus, translucent or transparent to X-rays. Accordingly, the electrode assemblies would not interfere with standard imaging techniques. For instance, at least one of the flexible electrode pad 9, the therapy side 11, and the sensor housing 13 may be manufactured from radiolucent and/or radiotransparent materials. In one example, the flexible electrode pad 9, the therapy side 11, and the sensor housing 13 are all manufactured from radiolucent and/or radiotransparent materials. In general, radiolucent electrode pads may include materials that include both radiotransparent and radiopaque materials, where the main body of the electrode pad is transparent to X-rays, but the materials of the sensor (e.g., electronics, cable connections, etc.) are not transparent to X-rays. As a result, when the patient is subject to X-rays or other techniques of imaging, the electrode assemblies, or portions thereof (excluding materials that are not radiotransparent), adhered or otherwise applied on to the patient's body would not appear in the image, and so the internals of the patient may be suitably viewed.

The flexible electrode pads 9 each may include an insulating base layer 21 (e.g., flexible foam base layer) and a flexible conductor 23 provided on the therapy side 11 thereof (see FIG. 3, for example). The insulating base layer 21 is composed of a layer of flexible, soft closed cell-type polymer foam such as, but not limited to, medical grade polyethylene or other suitable material(s). The material of base layer 21 may be of a high enough density sufficient to provide a barrier to liquid or aqueous gel, so that the conductive gel is held substantially in place on the therapy side of the electrode pad. The material of the base layer 21 may also be flexible and/or compressible in nature so as to conform comfortably to the surface contours of a patient's anatomy when the electrodes are affixed to the patient, without irritation or lifting off from the body.

The dimensions of the base layer 21 may be determined based on physiological considerations for both transcutaneous pacing and defibrillation. The area of the conductor 23 of the flexible electrode pads 9, which may be smaller than the corresponding base layers 21, may be constructed to extend laterally past the heart so that the entire heart is in effect "covered" by a defibrillation pulse. In addition, the base layer 21 dimensions may be chosen to provide some amount of area surrounding the conductor 23 for suitable adhesion to a patient's anatomy. For example, the area surrounding the conductor 23 can be coated with a hypoallergenic medical grade acrylic adhesive designed for use on human skin. This adhesive provides the mechanism for temporarily affixing the flexible electrode pads in position on a patient's anatomy. Using such an adhesive, no additional adhesive or additional manual force may be required to maintain the electrodes in position during delivery of electrical signals to a patient. Further details of the flexible electrode pads can be found in U.S. Pat. No. 5,330,526, entitled "Combined defibrillation and pacing electrode," which is assigned to the assignee of the present application and is hereby incorporated by reference in its entirety.

The sensor housing 13 may include one or more layers of compressible, padded material which, as discussed above, may be attached to the side 15 of the flexible electrode pad 9 opposite the therapy side 11 at an attachment region 17 such that the sensor housing 13 is not connected across the entire surface of the flexible electrode pad 9. As an example, shown in FIGS. 2B and 4, the sensor housing 13 may include a single layer of compressible, padded material which is thicker than the flexible electrode pad 9 such that the sensor housing 13 exhibits a greater degree of rigidity as compared to the electrode pad 9. In this case, the padding portion of the sensor housing 13 may be substantially thicker than that of the electrode pad 9 and, hence, the padding portion of the sensor housing 13 may be more rigid than the electrode pad 9.

In another example, and as shown in FIG. 3, the sensor housing 13 may include a plurality of layers of compressible, padded material. These layers may be laminated to each other to form the sensor housing 13 and adhered to the flexible electrode pad 9 at the attachment region 17. In some embodiments, the layers may be adhesively bonded, integrally formed or otherwise attached to each other, and further attached to the electrode pad 9 at the attachment region 17. In various embodiments, the compressible, padded material of the sensor housing 13 has a rigidity that is greater than that of the flexible electrode pad 9, yet may still be compressible as a padding material. Non-limiting examples of such material include medical grade polyethylene, foam, flexible polymeric material, gel, or other suitable materials.

Embodiments of the present disclosure allow for electrode assemblies where a motion sensor 19 is positioned directly over the flexible conductor 23 of the electrode pad 9. This may be particularly advantageous for pediatric or neo-natal resuscitation assemblies, which are relatively small compared to their adult counterparts due to the limited amount of surface space available. By way of context, conductive materials such as those incorporated in electrode pads 9 discussed herein may be prone to wear and/or damage when subject to repeated compressive loading applied directly thereto. Such wear or damage may include, for example, roughened surfaces, jagged edges, dislodged/displaced material, etc., which may result in the development of regions having uneven electrical resistance. When certain regions of the conductive material are more resistive than others, there may be a greater tendency for heat to be undesirably localized (e.g., "hot spots") during defibrillation discharge. Such thermal localization may result in pain, burns, or other issues to the patient. However, when the compressive forces applied during chest compressions are well distributed, for example, directed at a location substantially away from the conductive material or are otherwise reduced/minimized (e.g., via padded, cushioned structure), it is less likely for the conductive material to develop wear or damage, hence, reducing the occurrence of hot spots along the patient's body during discharge. The construction of electrode assemblies provided herein allow for such compressive forces to be distributed in such a manner that minimizes or otherwise reduces the likelihood that the conductive material be undesirably damaged.

With reference to FIGS. 1A and 2A, the sensor housing 13 of electrode assembly 1A may be configured to enable a rescuer to apply chest compressions thereto. In this case, the sensor of resuscitation electrode assembly 1A is offset from the center of the conductive material of the electrode pad 9 so that the conductive material is more likely to remain undamaged during chest compressions. Also, the sensor may be positioned a suitable distance away from the electrical connection to the electrode pad, so that there is a reduced chance for the connection itself from being damaged during compressions. In addition, an upper surface 24 of the sensor housing 13 of electrode assembly 1A can include graphics, such as a cross-hair indicia 25, that serves to guide a user to properly place the sensor housing 13 at a suitable anterior position over the sternum of the patient 3.

In additional examples, the electrode assembly 1B, illustrated in FIGS. 1B and 2B, may be configured such that the motion sensor 19 is located over a central portion of the conductive material. Accordingly, the sensor housing 13 of electrode assembly 1B is configured to distribute compressive forces indicative of CPR substantially evenly across the conductor 23 of the flexible electrode pad 9. That is, for the posterior positioned electrode assembly 1B, even though compressive forces are transferred between the conductive material of the electrode pad 9 and the (comparatively rigid) motion sensor 19, the potentially damaging effect(s) of such forces may be reduced, for example, due to enhanced cushioning provided by the sensor housing 13. For example, the thickness of the padded material of the sensor housing 13 may provide sufficient cushioning for the conductor 23 to remain undamaged during chest compressions.

With reference to FIG. 4, the motion sensor 19 may be enclosed within the compressible padded layer(s) of the sensor housing 13. The motion sensor 19 may be a three-axis accelerometer or any other suitable motion sensor. As shown in FIG. 4, the motion sensor 19 may be located over a central region of the conductor 23 of the flexible electrode pad 9.

The motion sensor 19 may have any suitable shape. For instance, as shown in FIG. 4, the motion sensor 19 may have a square or rectangular shape. This shape may be the shape of the motion sensor 19 itself or formed by a casing or other covering, such as an encapsulation or overmolding as discussed below. Alternatively, as shown in FIGS. 7 and 10, the motion sensor may have a circular shape. Other shapes and sizes may be possible, for example, the motion sensor may exhibit shapes that are polygonal, oval, similar to a credit card or coin, amongst others. As discussed above, the sensor housing 13 may be structured so as to distribute compressive forces substantially evenly across the conductor 23 during CPR chest compressions. In further embodiments, the motion sensor 19 may be located at a periphery of the conductor 23 of the flexible electrode pad 9 as shown for example in FIGS. 6 and 9 discussed in greater detail hereinafter.

In order to further protect the motion sensor 19 from the environment, such as moisture, humidity, defibrillation shocks, etc., it may be encapsulated or overmolded with a polymeric material, such as a moldable polyamide, to form a suitable sensor casing. The polymeric material may be suitable to provide long term protection from extreme temperature and moisture condition, as the overall assembly may be stored for years at a time. A non-limiting example of such a material is Macromelt OM652/Technomelt PA 752 provided by Henkel Corporation. The encapsulation material may be directly overmolded onto the motion sensor 19 or may form a protective casing in which the motion sensor 19 is positioned. The material may further be flexible, textured and/or slightly compressible, to provide enhanced comfort for the user, yet also sufficiently rigid or high enough in strength so as to provide protection for the sensor itself.

As discussed herein, the casing for the sensor may provide not only a protective covering for the sensor itself, but also may provide a source of traction for the provider of chest compressions, particularly where there may be a tendency for the rescuer's hands to slip on bare skin, for example, covered by blood, fluids, sweat, or other lubricating material. Any suitable material(s) and construction may be used. For example, the sensor casing may include multiple materials and/or layers, such as a rigid plastic for an inner portion that encapsulates the sensor itself to protect the electronics (e.g., accelerometer circuit), and a softer material (e.g., silicone, rubber, elastomer, polyurethane, neoprene, gel, polymeric material) provided as an over mold or thin coating for added comfort.

The material(s) of the casing may exhibit an appropriate level of hardness. In certain embodiments, as noted above, the casing may include a relatively rigid inner protective cover and a softer exterior covering. For example, relatively softer material(s) of the casing for providing added comfort for the user may have a shore A durometer of between approximately 40 and approximately 90, between approximately 40 and approximately 60, between approximately 50 and approximately 80, between approximately 60 and approximately 70, or a shore A durometer outside of the above noted ranges. Relatively hard material(s) of the casing for providing added protection for the sensor circuitry may have a shore D durometer of between approximately 20 and approximately 80, between approximately 30 and approximately 60, between approximately 30 and approximately 50, or a shore D durometer outside of these ranges. In some embodiments, as noted above, the sensor casing may include a relatively hard material that is coated with a thin softer material or laminate.

By providing a suitable motion sensor in both the anteriorly positioned electrode assembly 1A and the posteriorly positioned electrode assembly 1B, the signals obtained therefrom can be processed by control circuitry provided in the defibrillator 5 to provide information that enhances overall resuscitation care to the patient. For example, data from both motion sensors may be processed to determine more accurate compression depth, particularly when compressions are performed on a compressible surface and/or when, on an infant, a rescuer wraps his/her hands around the infant's chest and squeezes from both the front and back, as will be discussed in greater detail hereinafter.

As one mechanism to ensure proper placement of the electrode assemblies 1A, 1B of the resuscitation assembly onto the patient's anatomy, one or both of the electrode assemblies, or a substrate connected to the assemblies, may be provided with pictograms, diagrams, or printed instructions 27 describing the correct position for the electrode assemblies 1A, 1B. For example, pictograms, diagrams, or printed instructions may be provided on an upper surface 24 of the sensor housing 13 or the side 15 of the flexible electrode pad 9 opposite the therapy side 11. In addition, signals from the motion sensors 19 may be utilized by the control circuitry of the defibrillator 5 to prompt the user in the manner in which the resuscitation assemblies, including the electrode assemblies 1A, 1B, should be placed as discussed in U.S. patent application Ser. No. 15/083,044, entitled "ECG and Defibrillator Electrode Detection and Tracking System and Method," filed on Mar. 28, 2016, which is hereby incorporated by reference in its entirety.

As discussed herein, the sensor housing 13 may be constructed such that it is generally more rigid than the flexible electrode pad 9. Accordingly, as shown in FIGS. 2A, 2B and 2C, at least a portion 29 of the flexible electrode pad 9 is constructed and arranged to retain its flexibility throughout the portion not corresponding to the attachment region 17 such that the electrode pad 9 substantially conforms to the patient's anatomy when coupled to the patient 3. As shown in FIG. 2A, the attachment region 17 is provided along a portion of the upper left periphery of the flexible electrode pad 9 (when viewing the assembly from the top). With reference to FIG. 2B, the attachment region 17 can be located at a central region of the flexible electrode pad 9 such that the sensor housing 13 is free from attachment with a periphery of the flexible electrode pad 9. In some embodiments, the resuscitation assembly shown in FIGS. 2A-2C is intended for use in the A-P position, and may particularly beneficial for use with pediatric patients.

It can be appreciated that various alternative attachment regions 17 may be utilized such as, but not limited to attachment at a central upper region and/or a central lower region of the assembly. In each configuration, since the more rigid sensor housing 13 is only connected at the attachment region 17 and not across the entire surface of the flexible electrode pad 9, forces delaminating or otherwise pulling the flexible electrode pad 9 away from the patient's anatomy due to the connection between the sensor housing 13 and the flexible electrode pad 9 are reduced and at least a portion of the flexible electrode pad 9 is capable of flexing away from the sensor housing 13. This allows the flexible electrode pad 9 to better follow contours of the patient's anatomy so as to be suitably adherent thereto while remaining attached to the sensor housing 13 than would otherwise be the case if the flexible electrode pad were attached completely flush to the sensor housing. The flexible electrode pad is also able to provide relatively uniform electrical contact between the electrode and the patient, so as to maintain a sufficiently large active area of contact for a suitable amount of electrotherapeutic (e.g., defibrillation) energy to be delivered. Otherwise, if the electrode pad is not flexible enough to conform to the patient's anatomy, the reduced surface area may lead to issues, such as burning, skin damage, and/or improper electric field lines between electrodes, giving rise to improper delivery of electrotherapy.

It should be understood that embodiments of a resuscitation assembly may employ other arrangements. With reference to FIGS. 5-8, an alternative example of an electrode assembly 51 of a resuscitation assembly is illustrated. In this example the resuscitation assembly comprises one or more electrode assemblies. FIGS. 5-8 illustrate how one of the electrode assemblies may be constructed. For example, an electrode assembly 51 may be configured to be attached at a posterior position on a patient's back. The electrode assembly 51 includes a flexible electrode pad 53 having a therapy side 55 configured to be coupled to the patient 3, a sensor housing 57 attached to a side of the electrode pad 53 opposite the therapy side 55, and a motion sensor 59 (with associated casing) enclosed within the sensor housing 57.

The flexible electrode pad 53 may be any type of electrode suitable for use in defibrillation, and generally includes a conductor, such as tin, silver, AgCl or any other suitable conductive material, provided at the therapy side 55; an electrolyte, such as a hydrogel; and lead wires to connect the conductor to a cable as discussed herein.

For various embodiments, and as shown in this figure, the sensor housing 57 may include a plurality of layers of compressible, padded material attached to the side of the flexible electrode pad 53 opposite the therapy side 55 at an attachment region (not expressly shown) such that the sensor housing 57 and the flexible electrode pad 53 are not connected across the entire surface of contact. While not shown in FIGS. 6-8, the sensor housing 57 may be attached to the flexible electrode pad 53 similar to the manner in which the sensor housing 13 of electrode assembly 1B is attached to the flexible electrode 9 as shown in FIG. 2B. For instance, the attachment region may be located at a central region of the flexible electrode pad 53 such that the flexible electrode pad 53 deflects or otherwise flexes from the sensor housing 57 at a location away from the attachment region, peripheral to the central region, whereby the electrode pad 53 substantially conforms to the patient's anatomy when coupled to the patient 3.

Figure 5:
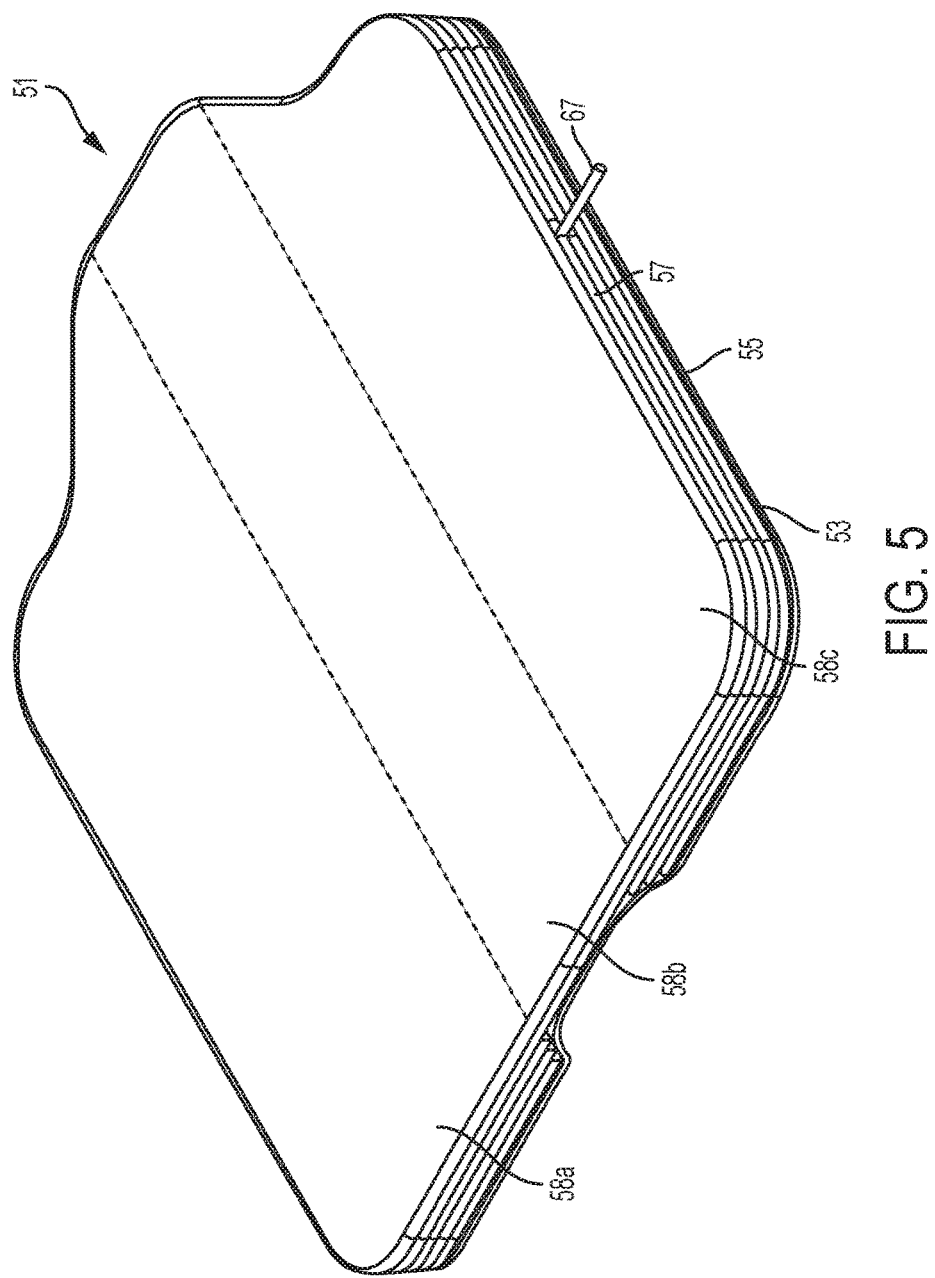
FIG. 5 is a perspective view of an alternative example of an electrode assembly in accordance with the present disclosure.
Figure 8:
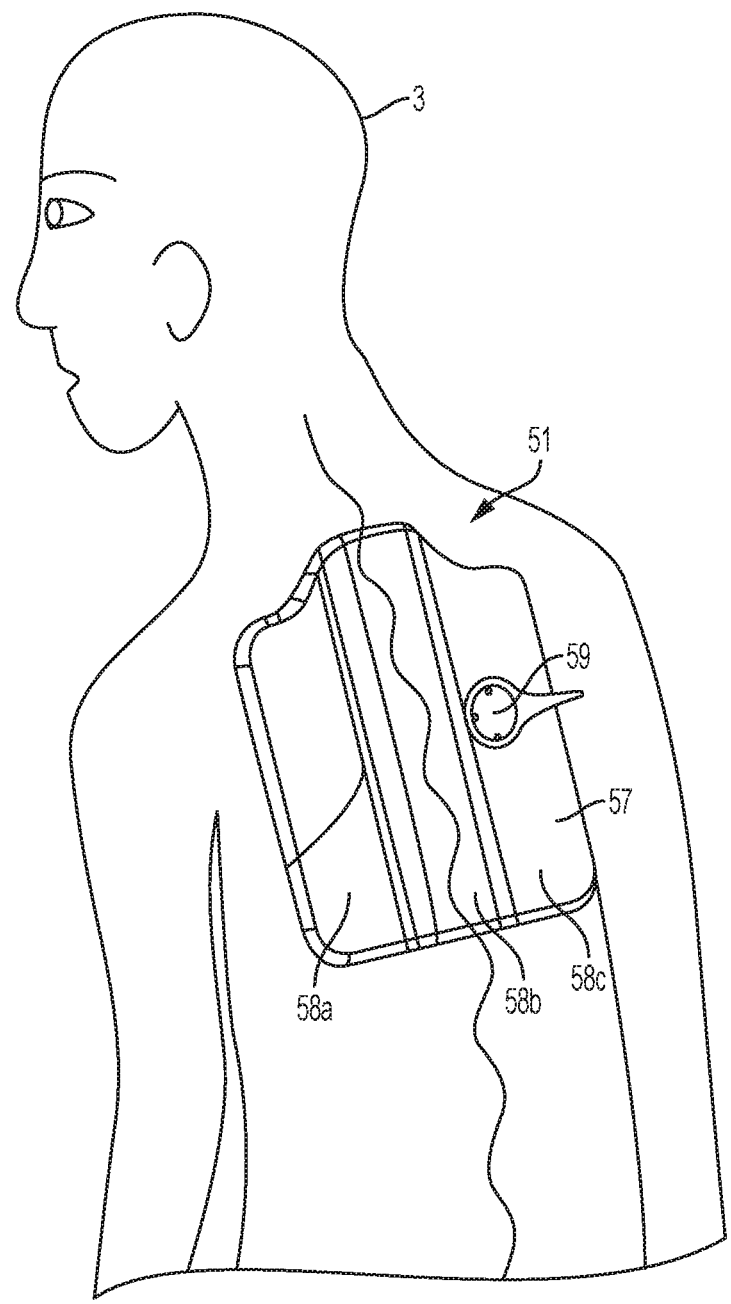
FIG. 8 illustrates placement of the electrode assembly of FIG. 5 on a victim.

The electrode assembly 51 may be structured according to any suitable configuration. For example, certain portions of the electrode assembly 51 may be shaped to accommodate and suitably conform to various parts of the anatomy upon placement thereon. For some embodiments, the sensor housing 57 and/or electrode pad 53 may be constructed such that the assembly comprises columns of differing thickness, resulting in better conformance of the assembly to the patient's anatomy. For example, as shown in FIGS. 5 and 8, the sensor housing 57 may be patterned in three columns 58a, 58b, and 58c. As illustrated, the first column 58a and the third column 58c may exhibit a similar thickness, whereas the second column 58b may have a smaller thickness so that the assembly 51 may be more geometrically appropriate to accommodate space occupied by the spine of the patient 3. Alternatively, for certain embodiments where it may be preferred for the sensor not to be placed over the spine, columns of varying thicknesses are not necessary. For example, an image of the spine may be provided on the posterior assembly (e.g., sensor housing or electrode pad) so that the assembly is placed in a manner that avoids placement of the sensor directly on or over the spine.

In some embodiments, the sensor housing 57 may include multiple layers laminated to each other to form the overall sensor housing. These layers may be further laminated or otherwise attached to the flexible electrode pad 53 at the attachment region. Alternatively, the layers may be adhesively bonded to each other and to the electrode pad 53 at the attachment region. The layers may be attached to one another by any other suitable method, such as by one or more fasteners (e.g., stitches, sutures, staples, etc.), or portions of the layers may be integrally formed. It can be appreciated that a layered configuration is not required, as covering materials may be shaped, molded, machined, pressed, modified or otherwise produced in any suitable manner.

The compressible, padded material of the sensor housing 57 may be more rigid than the flexible electrode pad 53, yet may still be compressible in nature. With specific reference to FIG. 6, at least one of the layers of the sensor housing 57 may have a cut-out region 61 or other recess having a substantially similar size and shape as the motion sensor 59 and configured to receive the motion sensor 59 therein. Accordingly, the motion sensor 59 may be embedded in only a small portion of the compressible, padded layers of the sensor housing 57, laterally offset from the conductor of the electrode pad 53. This allows forces from compressions to be distributed evenly across the sensor housing and may substantially prevent the motion sensor from damaging the electrode pad 53.

As noted herein, resuscitation assemblies described herein may be used with electrode assemblies thereof placed in the A-P position, the A-A position, or both, or in another position (e.g., lateral-lateral position). Resuscitation assemblies may be configured to perform a number of functions, including for example, defibrillation (e.g., hands free defibrillation energy according to energy levels set by a suitable defibrillator), ECG monitoring (e.g., for at least 24 hours), noninvasive temporary pacing (e.g., 1-8 hours of hands free noninvasive pacing energy, at approximately 75 mA/150 ppm or approximately 140 mA/180 ppm), transmitting chest compression data to a medical treatment apparatus (e.g., defibrillator, monitor, CPR system), code readiness self testing, expiration dating, having at least a 24 month shelf life. With respect to code readiness self testing, the electrodes of the resuscitation assembly may be pre-connected to a defibrillator (e.g., hospital defibrillator such as the R SERIES defibrillator provided by ZOLL Medical) so that the assembly is ready for use at any time. During the code readiness self testing, the defibrillator may automatically test for the presence of correct cables and electrodes, and verify the type, condition and/or expiration date of the electrode(s), without requiring the electrodes to be disconnected. For the electrode assemblies, according to IEC 60601-2-4 cls.201.108.1.1, the AC small signal impedance of the electrodes is 3 kOhms or less at 10 Hz, and 5 Ohms or less at 30 kHz, and the AC large signal impedance is 3 Ohms or less at a 200 J biphasic defibrillation. According to IEC 60601-2-4 cls.201.108.1.4, the defibrillation recovery offset is 750 mV or less following a 200 J biphasic defibrillation at 4 and 60 seconds, and according to IEC 60601-2-4 cls.201.108.1.6, the DC offset voltage is 100 mV or less following a 200 J biphasic defibrillation.

In certain embodiments, the resuscitation assemblies may be single use disposable and used on certain types of patients. Such patients with which the resuscitation assemblies are intended for use may include pediatric patients 0-8 years in age and less than 55 lbs (25 kg), adult patients greater than 8 years old and more than 55 lbs, or both types of patients. Motion sensors (anterior or posterior) associated with the resuscitation assemblies may be constructed to withstand at least 150 lbs of compression force or more applied directly thereto, and at least 200 compressions per minute. Such motion sensors may further be able to withstand the weight of a patient's body, in addition to the compression force discussed above.

The resuscitation assemblies may also include one or more components that allow for a medical system to identify whether the resuscitation assembly is configured for pediatric resuscitation or adult resuscitation, or whether the resuscitation assembly has one or more motion sensor inputs (e.g., a single sensor or multiple sensors). In some cases, the resuscitation assembly may include a memory chip for identifying the type of electrode assemblies, resistor (e.g., approximately 2.9 kOhm patient identification resistor for pediatric electrode assemblies, approximately 1.3 kOhm patient identification resistor for adult electrode assemblies), or other suitable identification component that is analyzed and from which an identification signal may be transmitted. This identification signal may provide information for the system to determine what type of resuscitation assembly is being used. As an example, a resuscitation assembly in accordance with the present disclosure may be connected to a defibrillator or monitor, and the system, using associated processing circuitry, may analyze and/or receive an identification signal based on the identification component of the resuscitation assembly. Where the identification component is a resistor, the system may run a current through the resistor, and based on the resulting voltage, the type of resuscitation assembly may be identified. Alternatively, where the identification component is a memory chip, the system may read whether the resuscitation assembly is pediatric or adult based on the contents of the memory.

Once the system and associated processing circuitry determines the type of resuscitation assembly that is connected, various resuscitation-related features of the system are adjusted accordingly to suit the therapy, such as electrotherapy, CPR parameters, user interface display, shock analysis, and/or other aspects of resuscitative therapy. For instance, if the system detects that a pediatric assembly is in use, the system may set the defibrillation energy level to be lower than if the system detected an adult assembly. Alternatively, depending on whether a pediatric or adult resuscitation assembly is detected, the user interface for providing CPR feedback may be altered. For example, when detecting that an adult assembly has been connected, the user interface may provide estimated chest compression depth and rate values for the rescuer, and also provide instructions for the rescuer to apply chest compressions within a certain range of depth (e.g., 2.0-2.4 inches) and rate (e.g., 100-120 cpm), according to current clinical guidelines. However, when detecting that a pediatric assembly has been connected, the user interface may provide only estimated chest compression depth and rate values, without instructing the rescuer on the proper application of chest compressions, for example allowing a trained rescuer to administer chest compressions to the patient without instructions. Further, the shock analysis algorithm applied may differ depending on whether the system detects a pediatric or adult resuscitation assembly. For instance, the pediatric shock analysis algorithm can be calibrated to analyze a child's ECG signal rather than an adult's EGC signal such that the defibrillator can make a more accurate determination of whether a shock should be delivered to the pediatric patient. In general, the defibrillator can measure the ECG baseline content, QRS rate, width and variability, amplitude, and temporal regularity and determine whether a shockable rhythm exists. For the pediatric patient, one or more of the measured values can be different for a shockable rhythm than for the adult patient.

With specific reference to FIG. 7, the motion sensor 59 which, in some cases, may be embodied as a three-axis accelerometer, is mounted on a printed circuit board 63 and encapsulated within an appropriate casing 65, provided as a protective covering or encasement. As noted above, such a casing may provide the motion sensor 59 with a suitable amount of protection, for example, from electrical discharge and/or environmental factors (e.g., moisture, humidity, temperature, heat). The casing 65 may include any suitable material, such as a polymeric/plastic material. The casing 65 is then positioned within cut-out region 61 such that a lead wire 67 extends out of the plurality of compressible, padded layers of the sensor casing 57. The lead wire 67 is configured to transmit the signal from the motion sensor 59 to the control circuitry of the defibrillator 5. The lead wire 67 may include a cable having any suitable cross-sectional shape, and in some cases, may be round or flat. In some examples, the lead wire 67 is substantially flat (e.g., flat ribbon cable) because the use of flat wires may provide a greater level of comfort for the rescuer and patient while compressions are performed over the wire than would otherwise be the case. For instance, during chest compressions, a round or comparably shaped lead wire may have a tendency to undesirably impinge on or otherwise protrude into the rescuer and/or the patient, whereas a relatively flat lead wire may be less likely to protrude into or even be noticeable to the rescuer and/or patient. As shown, a protective covering portion of the casing 65 may have a shape that is substantially similar to that of the motion sensor itself, for example, to limit the overall amount of bulk around the motion sensor as well as provide for an enhanced maneuverability thereof.

Figure 9:
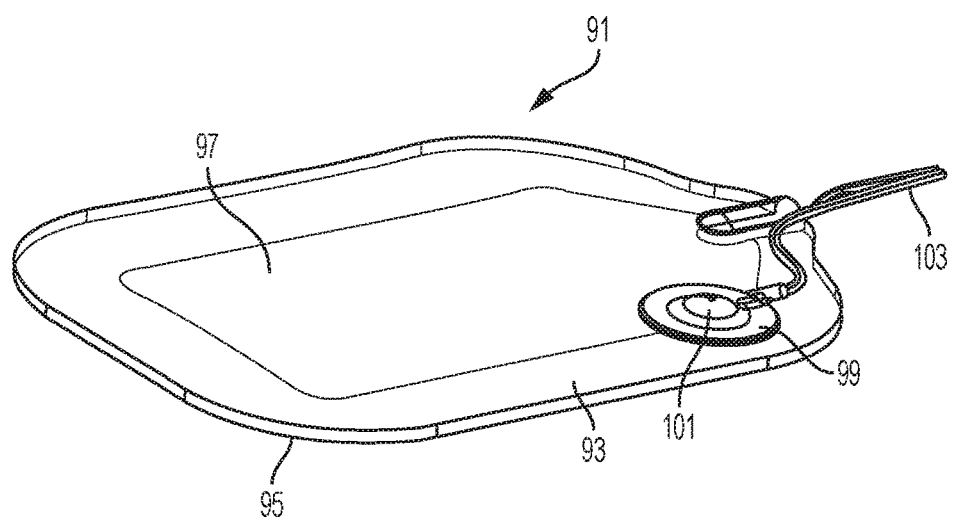
FIG. 9 is a perspective view of another example of an electrode assembly in accordance with an embodiment.
Figure 11:
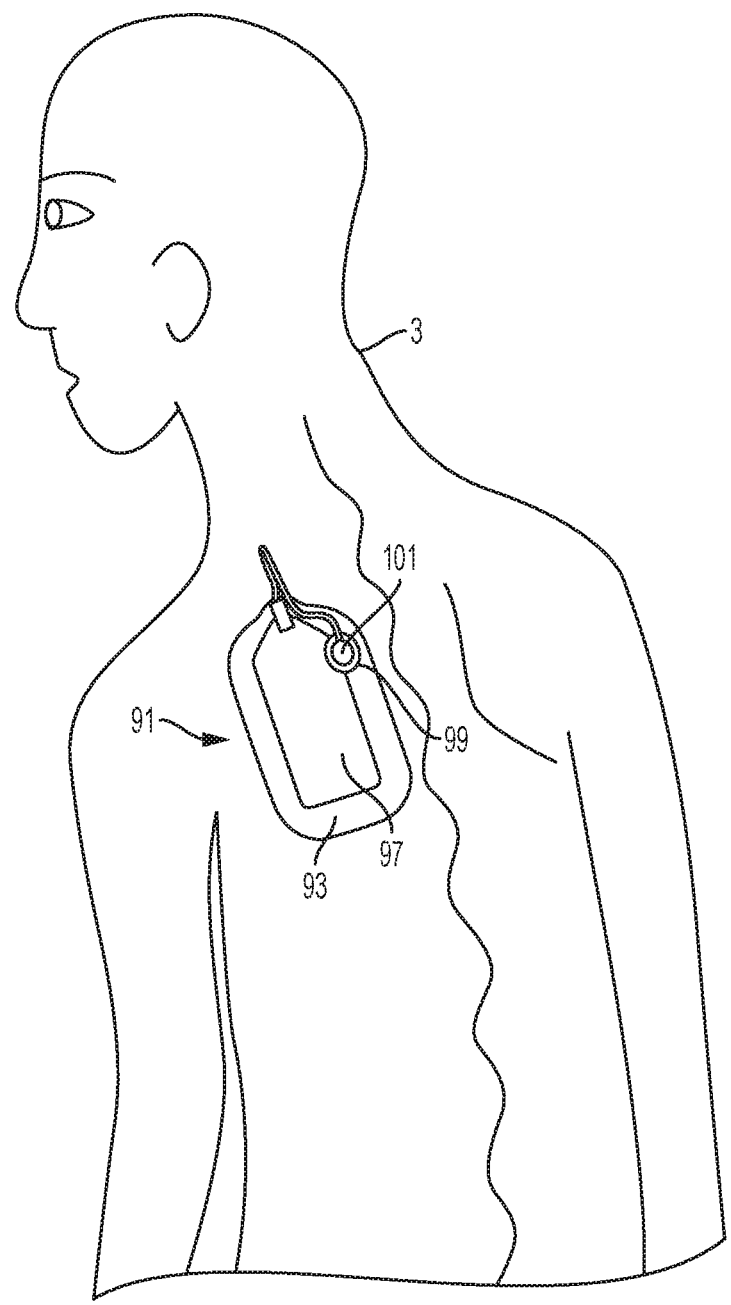
FIG. 11 illustrates placement of the electrode assembly of FIG. 9 on a victim.

FIGS. 9-11, illustrate another example of an electrode assembly for inclusion in the resuscitation assemblies of the present disclosure. This exemplary electrode assembly, generally denoted as reference numeral 91, is configured to be attached posteriorly to a patient's back (see FIG. 11). The electrode assembly 91 may include a flexible electrode pad 93 having a therapy side 95 configured to be coupled to the patient 3 and substantially conform to the patient's anatomy. The therapy side 95 includes conductive material 97, facing toward the body of the patient 3, adapted to provide therapeutic treatment to the patient.

In various embodiments, the sensor casing 99 may be coupled to the electrode pad 93 such that a projected contact area between the sensor casing 99 and the electrode pad 93 is relatively small, such as between approximately 1-100 $cm^2$. As a result, the more rigid sensor casing 99 is small enough so that the upward force from the casing 99 is insufficient to cause delamination of the electrode pad 93 from the patient's body. In one example, the projected contact area between the sensor casing 99 and the electrode pad 93 (or simply the projected area of the sensor casing itself) is less than about 100 $cm^2$, less than about 80 $cm^2$, less than about 50 $cm^2$, less than about 30 $cm^2$, less than about 20 $cm^2$, less than about 10 $cm^2$, or less than about 5 $cm^2$. In some embodiments, the sensor casing 99 is roughly the size of a nickel. In an embodiment, the sensor casing may be approximately or less than 1.0 inch×1.0 inch×0.25-0.30 inches in size. In further embodiments, the casing may have a projected area of approximately 0.1-4.0 $inch^2$ (e.g., 1.0-2.0 inch length, 1.0-2.0 inch width) and approximately 0.01-0.30 inches in height. Or, with the development of progressively smaller motion sensors (i.e., smaller chip sets), the sensor casing 99 may be as small as an encapsulating wire housing. Accordingly, the sensor casing 99 is embedded in only a small portion of the flexible electrode pad 93, thereby allowing the remaining portions of the flexible electrode pad 93 to have more flexibility in adhering to the patient 3. That is, by incorporating a relatively small sensor casing 99 encapsulating an appropriately sized motion sensor 101, the likelihood that the electrode pad 93 lifts off from the patient 3 is reduced. In some embodiments, the outer surface of the sensor casing may include an appropriate texture or suitable material (e.g., molded rigid, semi-rigid, polymeric material with texturing, ridges, etc.) to prevent slippage of the rescuer's hands during compressions as well as provide an enhanced level of comfort for the rescuer and the patient. That is, while the casing may provide protection for the motion sensor, it is not a requirement for the casing to be rigid. For example, the casing may provide a texture that is non-rigid and soft to the touch for the user/patient as an added degree of comfort.

As shown, the motion sensor 101 is at least partially enclosed within the sensor casing 99. The motion sensor 101 may be configured to be positioned over a periphery of the conductive material 97 such that it is offset from the patient's spine. In one example, the sensor casing 99 is formed by encapsulating the motion sensor 101 in an appropriate polymeric material. A lead wire 103, operatively connected to the motion sensor 101, extends from the sensor casing 99 and is configured to transmit the signal from the motion sensor 101 to the control circuitry of the defibrillator 5.

As discussed herein, the sensor casing 99 and motion sensor 101 may be provided within a pouch or receptacle of the respective electrode pad to which they are associated. In some embodiments, while the sensor casing and motion sensor may initially be contained within a portion of the electrode pad (e.g., a housing, recess or receptacle thereof), the sensor casing and motion sensor may be removable therefrom, so that the rescuer can place the sensor casing and motion sensor at any suitable location. For instance, it may be desirable for the sensor to be placed at a location away from the electrode pad (e.g., to avoid wounds, provide more accurate CPR measurements) and so the rescuer may have the ability to easily access the sensor for subsequent placement. Or, it may be desirable for only the sensor to be employed, without the electrode pad, hence, it would be beneficial for the rescuer to have the flexibility to take the sensor from the electrode pad and place the sensor where needed. In some cases, it may be desirable for the sensor to be removed from the electrode pad and placed on the surface (e.g., backboard, mattress, gurney) on which the patient resides.

Traditionally, for instances in which the sensor is part of an electrode assembly (e.g., attached or otherwise coupled with an electrode pad), the system may require for there to be an indication that the electrode pad is applied to the patient before signals from the sensor are measured. As an example, an impedance measurement falling within a suitable range or achieving a particular threshold may be an indication for confirming that the electrode pads are appropriately applied to the patient. However, in situations where the electrode pad is not used, the system may not require that impedance (or another indication of pad placement) be a prerequisite for collecting signals from the sensor. For instance, a patient having a surgical dressing on the chest may limit the space available for electrode pad placement, and so it may be preferable for a sensor to be applied to the patient's chest, separate from the pad. In such cases, where the electrode pad is not required, ECG may be monitored via other sources (e.g., 3 lead ECG on hospital monitor). Accordingly, the system may include a suitable mechanism for disabling the need for patient impedance to be measured in order for signals to be transmitted and processed from the sensor. For example, the medical treatment apparatus (e.g., defibrillator, monitor) with which the sensor is in communication may have an input (e.g., switch, button, software configuration) with which a user may indicate that signals from the sensor(s) are to be processed, without first requiring other parameters, such as a suitable measurement of patient impedance, to confirm that the pad and/or sensor(s) are correctly placed.

Alternatively, for some embodiments, such as for neonatal resuscitation, it may be preferable for the electrode assemblies of the resuscitation assembly to exhibit a relatively low profile. For example, when treating an infant, the rescuer may wrap his/her hands around the infant's chest and squeeze from both the front and back (i.e., using the two-thumb technique as discussed further below). Hence, the electrode assemblies of the resuscitation assembly may be thin enough for there to be enough space allowing the hands to wrap sufficiently around the infant's body. Less padding may also be required for neo-natal resuscitation because less force is generally applied to infants in comparison to pediatric/adult compressions. In some embodiments, the resuscitation assemblies may have a thickness of less than approximately 30 mm (e.g., approximately 1-30 mm, approximately 5-30 mm), less than approximately 25 mm, less than approximately 20 mm (e.g., approximately 1-20 mm, approximately 5-20 mm), less than approximately 15 mm, less than approximately 10 mm, less than approximately 5 mm, less than approximately 2 mm, less than approximately 1 mm, or any other suitable range of thickness.

As described further herein, it can be appreciated that for some embodiments, the motions sensor associated with a particular electrode assembly is not integrated into a padding. For instance and with reference to FIG. 13A, a resuscitation assembly 131 includes a first electrode assembly 133a and a second electrode assembly 133b each having an electrode pad 135a, 135b and motion sensor 137a, 137b that are separate from one another, yet may each be connected to the overall system (e.g., via a cable 139 or wireless connection). In some embodiments, a sensor casing containing the motion sensor, where the sensor casing is provided as a small protective covering (e.g., without foam padded material), may be coupled to a patient, separate or separable from the remainder of the electrode assembly. As an example, the sensor casing and/or motion sensor may include an adhesive or other material that allows the sensor to be attached to and detached from the body, apart from the electrode pad.

Figure 13A:
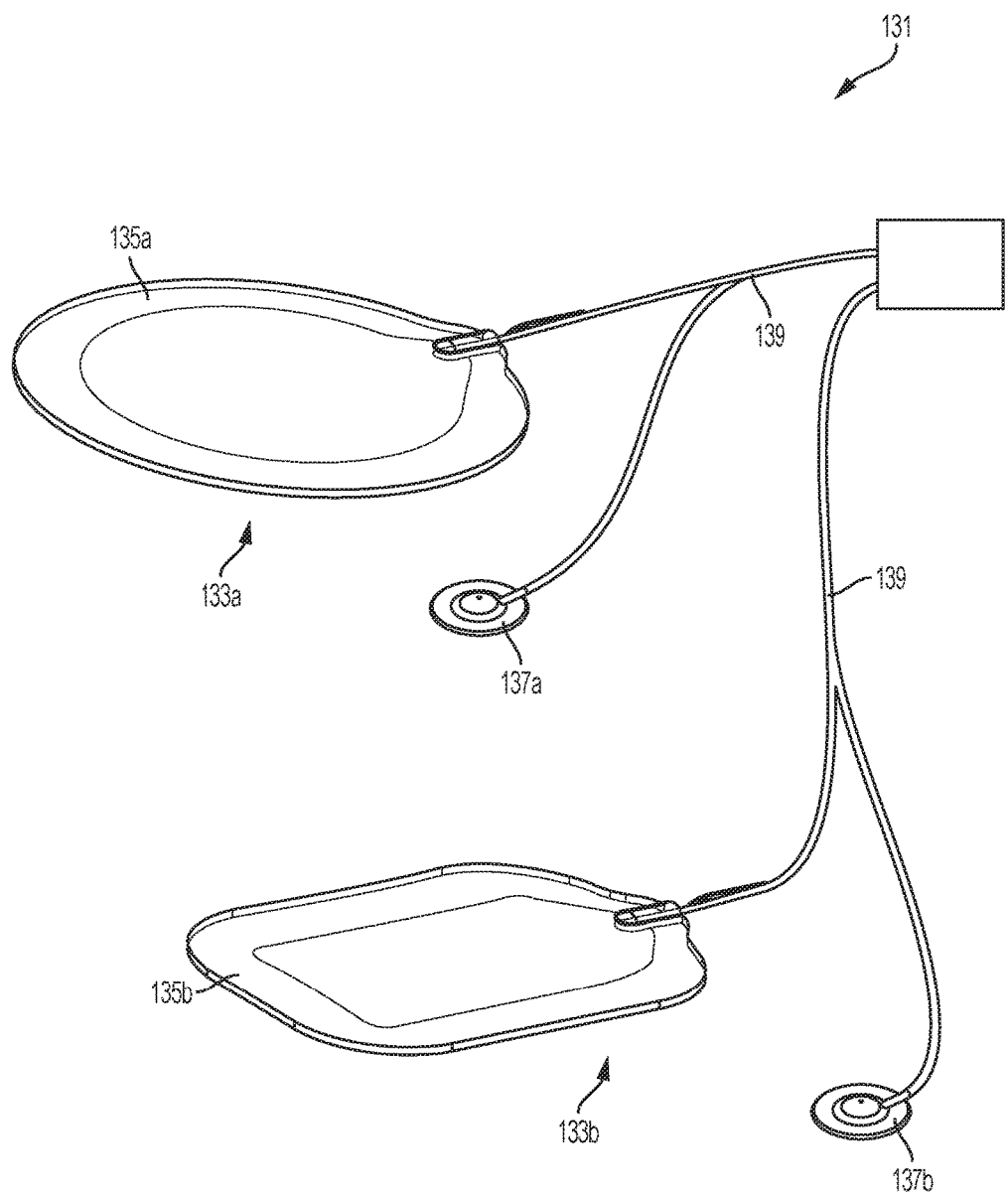
FIG. 13A is a perspective view of a resuscitation assembly in accordance with an embodiment.
Figure 13B:
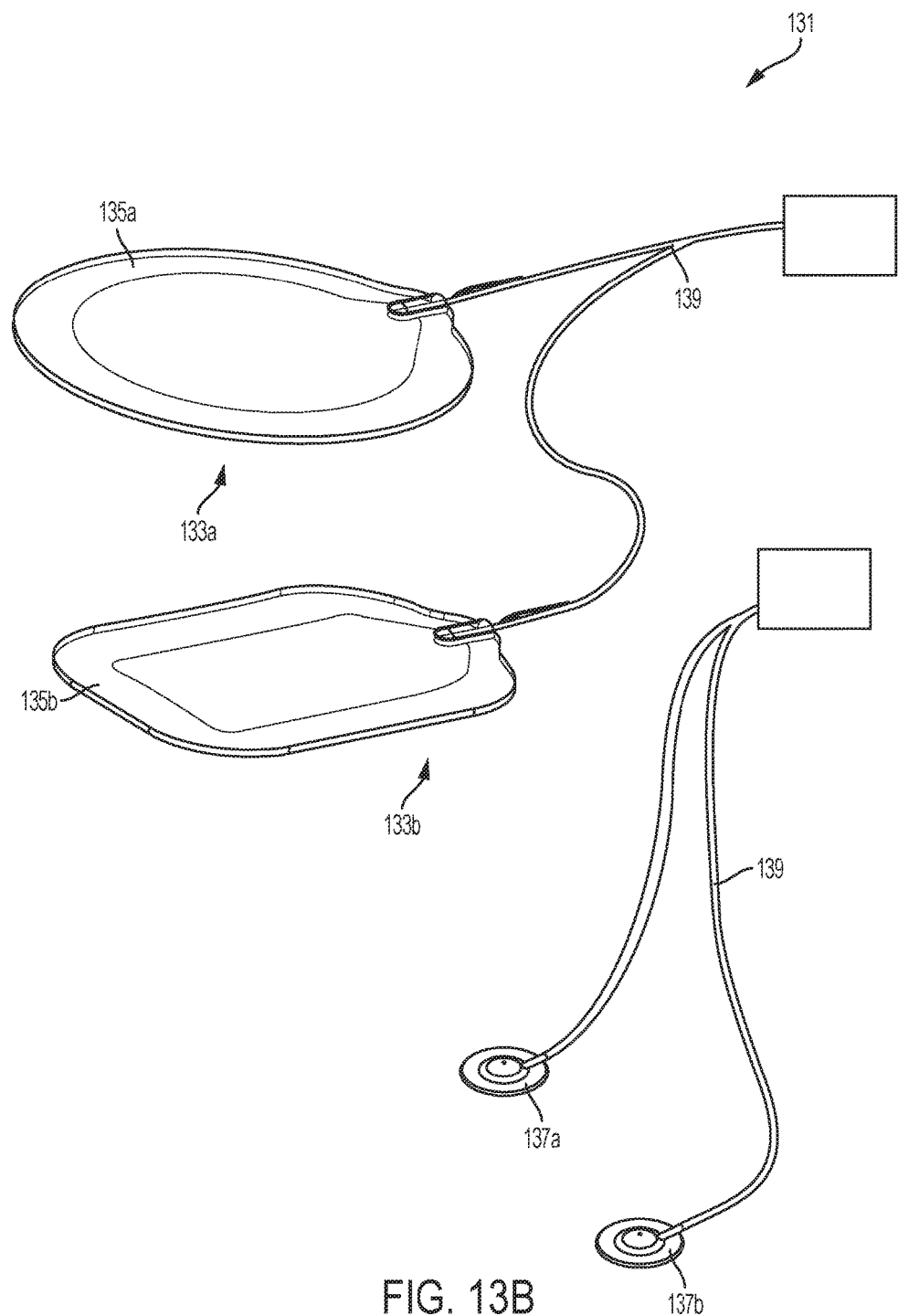
FIG. 13B is a perspective view of a resuscitation assembly in accordance with another embodiment.

Such a configuration, as shown in FIG. 13A, where motion sensors 137a, 137b can be freely attached to and detached from the body separate from the electrode pad 135a, 135b may be relevant if it is preferable for the location of compressions to vary, or if it is otherwise desirable for the motion sensor to be positioned at a location away from the electrode pad. For example, if a patient has had chest surgery, with wounds that do not allow for standard pad placement, it may be advantageous to have one or more separately attachable motion sensors 137a, 137b independent of the electrode pad(s) 135a, 135b to be attached at any suitable location. Or, in some cases, adjusting the location at which chest compressions is applied may give rise to increased levels of blood circulation. Alternatively, as shown in FIG. 13B, the motion sensors 137a, 137b may be completely separate from the electrode pads 135a, 135b. For example, as shown, the electrode pads 135a, 135b may be connected to a system for providing electrotherapy through the electrode pads, and the motion sensors 137a, 137b may be separately connected to a system for obtaining signals from the motion sensors, for determining one or more parameters related to chest compressions, such as chest compression depth, rate and/or velocity.

The processor(s) circuitry for processing of signals arising from the motion sensor(s) may be disposed at any suitable location. Such processing may include, for example, integrating acceleration signals to result in displacement information, or subtracting posterior acceleration or displacement information from anterior acceleration or displacement information. Other types of processing and analysis may be possible. In an example, the processor(s) may be disposed in defibrillator, monitor, computing device, or other medical treatment apparatus. Accordingly, signals from the motion sensor(s) may be transmitted (e.g., wirelessly or through a cable) to the processor(s) on the medical treatment apparatus for analysis and, e.g., feedback. Alternatively, for signals transmitted via a wired cable system, the processor(s) may be disposed within a reusable portion of the cable system. For instance, as discussed herein, the sensor casing, motion sensor and associated cable may form a disposable assembly. This disposable assembly may be plugged into a reusable cable which is, in turn, in electrical communication with a corresponding medical treatment apparatus (e.g., defibrillator, monitor, etc.). By incorporating the processor(s) for processing the signals arising from the motion sensor(s) within the reusable cable, processing of such signals may occur quickly and efficiently without unnecessary bandwidth usage from the more complex medical treatment apparatus. As a result, the processor(s) within the reusable cable may send one or more processed signals to the medical treatment apparatus (e.g., defibrillator, monitor, CPR system) and/or back to the motion sensor and sensor casing. The medical treatment apparatus may collect the processed signals for further data analysis, reporting, or other function(s). In some cases, the sensor casing itself may incorporate circuitry that receives the processed compression information and provides an appropriate level of feedback to the user (e.g., LED, display, audio signal for guiding or assisting the user in performing CPR). In other embodiments, the processor(s) may be provided with the disposable assembly, for example, located within the sensor casing or associated cable. As an example, the motion sensor and the processor(s) for processing signals from the motion sensor may be provided on the same circuit chip. Communication between the motion sensor(s) and associated processor(s) may be digital and/or analog in nature.

Figure 14:
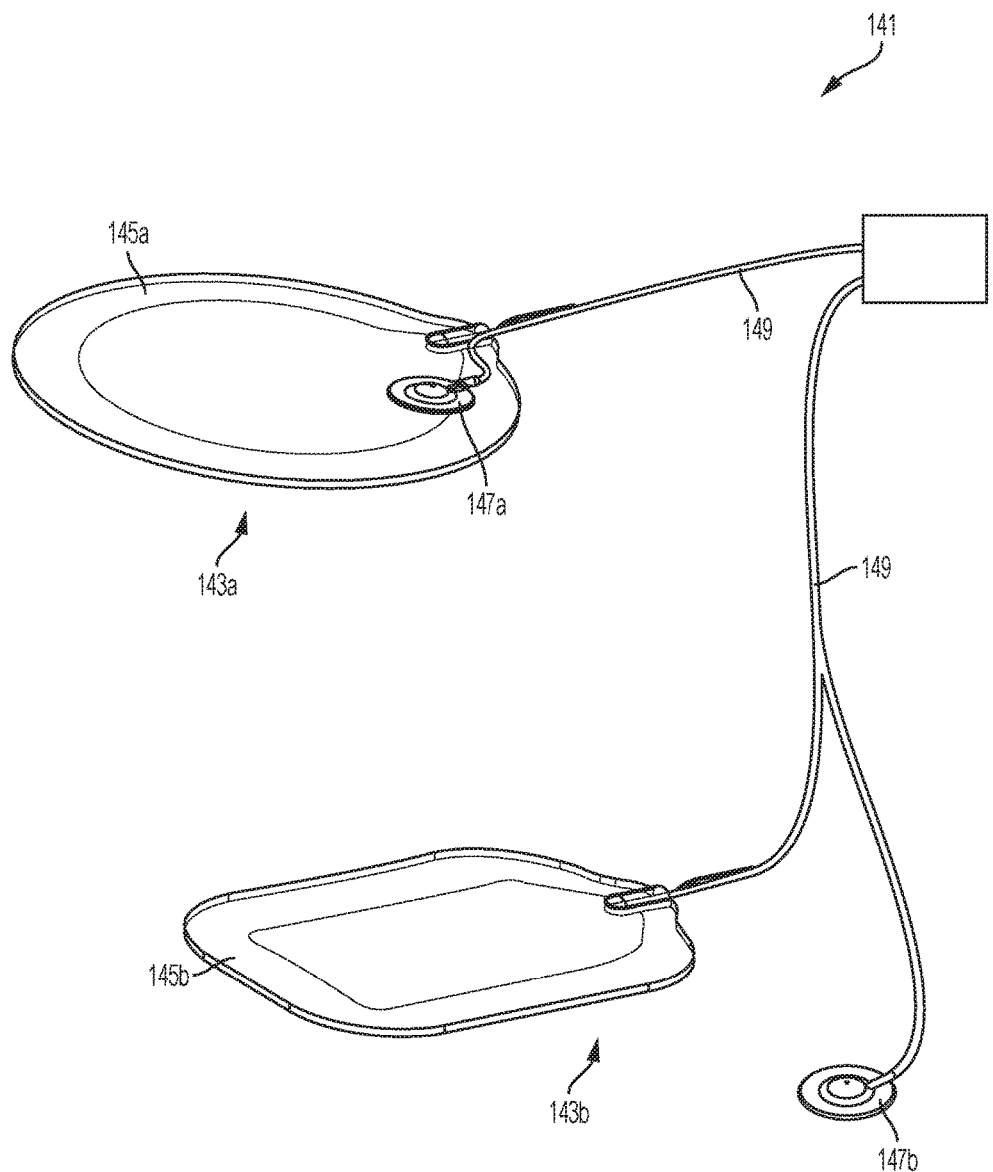
FIG. 14 is a perspective view of a resuscitation assembly in accordance with another embodiment.

In another alternative and with reference to FIG. 14, the electrode pads 145a, 145b of electrode assemblies 143a, 143b of a resuscitation assembly 141 may be placed in a certain configuration, such as an A-A position where one electrode pad 145a that includes a motion sensor 147a positioned on an upper surface thereof is placed on the sternum and another electrode pad 145b having a separate motion sensor 147b is placed on the side of the patient. In such a situation, the separate motion sensor 147b can be placed on the back or other suitable location of the patient, for example, to obtain more accurate or precise chest compression data even though the electrode pad 145b is placed on the patient's side. Cables 149 may be used to connect the electrode assemblies 143a, 143b and motion sensors 147a, 147b.

Chest compressions depth, velocity and rate measurements during CPR are typically made using a single sensor, for example an accelerometer contained in a housing placed on the chest of the patient at an anterior position, typically above the sternum. In such methods, the measured acceleration into the chest is twice integrated to determine chest displacement which is used to assess depth and rate of compressions, or integrated once to determine release velocity. An example of such a method is described in U.S. Pat. No. 9,125,793, entitled "System for determining depth of chest compressions during CPR," which is hereby incorporated by reference in its entirety. However, such measurements may contain error that cannot be accounted for, for example, error due to movement of a surface under the patient, patient motion and/or movement during transport, etc. As one example, if the patient is lying on a soft compressible surface, such as a mattress, the measured displacement will include not only the compression into the chest but also the depth of the deformation of the compressible surface. This can lead to an overestimation of compression depth. As another example, if the patient is in a moving ambulance the outside motion may further affect the compression measurements and contribute to error in estimating compression depth.

Resuscitation assemblies of the present disclosure may be utilized to provide feedback to a user regarding resuscitation activities (e.g., chest compressions, ventilations) being performed on the patient by the rescuer with improved accuracy. More specifically, in operation, a rescuer may place the electrode assemblies 1A and 1B of the resuscitation assembly in an A-P orientation, with the electrode assembly 1A being positioned on the patient's sternum and the electrode assembly 1B being positioned on the patient's back. Alternatively, as shown in FIG. 12, the electrode assemblies 1A' and 1B' of the resuscitation assembly are positioned on the patient in an A-A orientation. Specifically, in such a configuration, the electrode assembly 1A' is positioned on a right side of a chest of the patient 3 between the armpit and the sternum, with the portion of the electrode assembly comprising the motion sensor place substantially above the sternum. The resuscitation assembly 1B' is an apex electrode assembly and is positioned on a left side of the chest of the patient 3 over lower ribs of the patient 3. In either configuration, the motion sensors 19 of the electrode assemblies 1A, 1B, 1A', and 1B' may be provided as three-axis accelerometers as described hereinabove such that acceleration in the x, y, and z directions is measured simultaneously with each of two sensors incorporated within respective electrode assemblies.

As noted herein, it can be appreciated that other configurations of resuscitation assemblies may be employed. In some embodiments, an electrode assembly including an electrode pad and a motion sensor might not require the motion sensor to be directly attached to the electrode pad, or integrated within a padding material (part of a larger sensor housing) that is directly attached to the electrode pad. For example, the motion sensor may be coupled to the electrode pad via a cable or some other extension that allows for an electrical connection to the overall system as shown in FIGS. 13A, 13B, and 14. Or, the motion sensor may be completely free of mechanical attachment to the electrode pad. For instance, the motion sensor may be in wireless communication with the resuscitation system and be configured to be coupled to the body in any suitable manner (e.g., adhesively attached). In addition, the motion sensor(s) described herein may be provided with a memory that is able to store data from the time at which use of the motion sensor(s) commences. For example, the motion sensor(s) may be provided with a removable tab that, upon removal, activates the sensor to begin storing data in the memory. In addition, the motion sensor(s) may be provided with an audible/visual output system to provide a light or other visual display mechanism, or speaker or other audible output mechanism, to indicate that the system is active. The motion sensor(s) and/or associated casing may also include a chest compression metronome, audible speaker (e.g., for providing verbal coaching prompts), light (e.g., LED with colors red/green to indicate whether or not compressions are within acceptable ranges), or other component to guide the rescuer in providing chest compressions. Once the motion sensor is paired to a device (for example a defibrillator, a desktop top computer, a table computer, a mobile phone, a patient monitor, etc.), the data stored in the memory of the motion sensor is transmitted to the device and integrated in a case record for post-case review. In certain examples, the motion sensors may be wireless with an option for wired communication with a device for real-time feedback. Alternatively, communication between the motion sensors and the device may be exclusively wireless.

Accordingly, if the motion sensor is able to be moved from one location to another, the resuscitation system to which the motion sensor is communicatively coupled may provide instructions to a user as to whether the position of the motion sensor should be adjusted. For example, the motion sensor may be placed at a location unsuitable for gathering chest compression data. Hence, the system may provide instructions to a user to move the motion sensor to another location on the patient's anatomy. Or, when it is preferred for the location of compressions to periodically vary from position to position, for purposes of increasing overall blood circulation, the user may be prompted to detach the motion sensor from the patient's body and attach the motion sensor at a different location.

Once the electrode assemblies included with the resuscitation assemblies of the present disclosure are properly placed, they are operatively connected to a defibrillator 5 having control circuitry (not shown) and an output device, such as display 6 and/or a speaker (not shown), to provide output to a user. Such assemblies may be connected via cables 7, or alternatively one or more of the motion sensors may be operatively coupled to the defibrillator and/or other devices using wireless technology (e.g. Bluetooth, WiFi, radio frequency, near field communication, etc.). The control circuitry used in the defibrillator 5 may be any suitable computer control system, and may be disposed within the housing of the defibrillator. Alternatively, the control circuitry may be disposed within an associated defibrillator, within an associated mechanical chest compression device, or it may be a general purpose computer or a dedicated single purpose computer. The control circuitry may comprise at least one processor and at least one memory including program code stored on the memory, where the computer program code is configured such that, with the at least one processor, when run on the processor, it causes the processor to perform the functions assigned to the control circuitry throughout this disclosure. These functions include interpreting the signals from the motion sensors 19, and/or signals produced by other sensors, to determine compression depth, and produce signals indicative of the calculated compression depth, and operate outputs such as speakers or displays to provide feedback to a rescuer.

In one example, the output device of the defibrillator 5 provides information about patient status and CPR administration quality during the use of the defibrillator 5. The data is collected and displayed in an efficient and effective manner to a rescuer. For example, during the administration of chest compressions, the output device may display on display 6 information about the chest compressions.

The information about the chest compressions is automatically displayed in display 6 when compressions are detected. The information about the chest compressions displayed may include rate (e.g., number of compressions per minute) and depth (e.g., depth of compressions in inches or millimeters). The rate and depth of compressions, and/or release velocity, can be determined by analyzing readings from the motion sensors 19. Displaying the actual rate and depth data (in addition to or instead of an indication of whether the values are within or outside of an acceptable range) is believed to provide useful feedback to the rescuer. For example, if an acceptable range for chest compression depth is between 1.5-2 inches, providing the rescuer with an indication that his/her compressions are only 0.5 inches, can allow the rescuer to determine how to correctly modify his/her administration of the chest compressions.

More specifically, the control circuitry of the defibrillator 5 is operatively connected to and programmed to receive and process signals from the motion sensors 19 of the electrode assemblies 1A and 1B to determine whether at least one of a chest compression depth and rate and/or release velocity during administration of CPR falls within a desired range. The output device of the defibrillator 5 then provides feedback instructions to the user to maintain the chest compression depth and rate during CPR within the desired range.

With the electrode assemblies 1A and 1B positioned in an anterior-posterior position as shown in FIGS. 1A and 1B, in one example, the chest compression depth is calculated by subtracting a distance traveled by the motion sensor 19 of the electrode assembly 1B from a distance traveled by the motion sensor 19 of the electrode assembly 1A. More specifically, acceleration in the x, y, and z directions is measured simultaneously with the two motion sensors 19. The motion sensor 19 of the electrode assembly 1A (i.e., the primary sensor) is placed anteriorly on the chest while the motion sensor 19 of the electrode assembly 1B (i.e., the reference sensor) is placed as a reference posteriorly on the back as described hereinabove. The primary sensor is to be located in the center of the chest with compressions occurring in a substantially perpendicular direction relative to the sensor. The reference sensor may be positioned in alignment with the primary sensor and the net acceleration along the vertical y-axis (or other axis, such as z-axis, depending on how the patient is oriented with respect to the accelerometer and the direction of gravity) of the sensors may be used to determine overall compression depth.

In another example, the motion sensor 19 of the electrode assembly 1B positioned on the back of the patient provides a signal indicative acceleration caused by external accelerations, such as the patient being transported, and the motion sensor 19 of the electrode assembly 1A provides a signal indicative of acceleration caused by a rescuer or mechanical device performing chest compressions on a patient. A signal representing acceleration sensed by the motion sensor 19 of the electrode assembly 1A (i.e., the device acceleration) is provided to the control circuitry of the defibrillator 5. The device acceleration signal of the electrode assembly 1A records an overall acceleration indicative of the acceleration caused by compressions (the compression acceleration) and the acceleration caused by the external accelerations (the external acceleration). The motion sensor 19 of the electrode assembly 1B further provides a reference acceleration signal for the control circuitry of the defibrillator. The reference acceleration signal of the electrode assembly 1B records only the external accelerations of the patient caused from transporting or otherwise moving the patient.

Accordingly, the reference acceleration signal may be processed with the device acceleration signal to produce an estimated actual acceleration. Once obtained, the estimated actual acceleration may be double integrated to produce an estimated actual chest compression depth as discussed, for example, in U.S. Pat. No. 9,125,793. In addition, further details of the manner in which vehicle motion artifacts can be removed from ECG signals based on information provided by secondary motion sensors can be found in U.S. patent application Ser. No. 14/216,225, entitled "ECG Noise Reduction System for Removal of Vehicle Motion Artifact," which is hereby incorporated by reference in its entirety. For instance, the motion sensor incorporated within the resuscitation assembly 1B, 1B' placed on the back or side of the patient may record movement (e.g., based on detected accelerations) associated with transport, such as artifacts due to surface features on the road encountered by the ambulance and/or gurney carrying the patient, and/or vehicle acceleration and deceleration. Accordingly, artifacts resulting from patient transport, which may otherwise introduce errors into the overall estimation for chest compressions (or other CPR parameters) may be estimated and/or mitigated.

Based on the motion signals recorded from the motion sensors of the electrode assemblies of the resuscitation assembly of the present disclosure, processing circuitry in a system for providing resuscitation assistance may receive and process the recorded data to determine whether a patient is being transported or not. For instance, if the acceleration signals are associated with patient transport, the system may instruct a rescuer to take steps to ensure that the patient is properly secured. Once the patient is suitably secured, the system may instruct the user to administer chest compressions, or another resuscitation activity. Or, when rescuers are subject to a scoring system that evaluates their performance (e.g., report card) in carrying out resuscitation activities, if it is determined that the patient is being transported, the metrics for evaluating the rescuer may be adjusted. For instance, performing manual chest compressions while traveling in an ambulance may be more difficult than when not located in a traveling vehicle, and so the rescuer may be given a score which reflects such conditions. That is, to account for the rescuer being subject to conditions where it is more challenging to administer CPR or when CPR quality is likely to be compromised, such as during vehicular motion or transport, the manner in which a rescuer is evaluated may be relaxed and the overall performance evaluation may be higher. Or, for purposes of evaluating rescuer performance, CPR measurements during transport may be discounted from the overall score. Thus, the scoring rubric for assessing the rescuer may account for whether chest compressions are being administered during transport.

In addition, the system may further be configured to alert a user when there is concern for rescuer safety. For example, when a substantial amount of vehicle/transport motion is detected, to ensure that the rescuer does not become injured or become a potential liability (being a large object that can move suddenly within and throughout the vehicle cabin) for other passengers, it may be preferable for the rescuer to discontinue CPR and rather be placed under a safety restraint (e.g., seat-belt).

As noted previously, when electrode assemblies comprising one or more motion sensors in each are placed in the A-P position (front and back), oriented substantially parallel to one another (and the x-y planes of the 3-axis accelerometers being substantially parallel to the direction of gravity), and the patient is lying on a compressible surface such as a mattress or thick padding, the system to which the electrode assemblies are connected may accurately estimate the depth of chest compressions during CPR by subtracting out the distance traveled by the posterior placed assembly. When such electrode assemblies are placed in an A-A position (front and side), oriented substantially perpendicular to one another, rather than the subtraction technique described herein, the system to which the assemblies are connected may employ a different algorithm for estimating the depth of chest compressions. Similarly, the system may recognize the electrode assemblies to be placed in a lateral-lateral position (side and side), with 3-axis accelerometers oriented substantially parallel to one another and the x-y planes of the accelerometers being substantially perpendicular to the direction of gravity. For instance, when recognizing pads placed in an A-A position or a lateral-lateral, for purposes of estimating the depth of chest compressions, the system may elect to process data received from only the motion sensor positioned on the front of the patient without data from the motion sensor positioned on the side of the patient. Otherwise, inaccuracies may arise when the wrong correction algorithm is used, for example, using an algorithm corresponding to A-P pad placement when in fact the pads are placed in an A-A position. Alternatively, if the system, by obtaining and processing signals from the sensors indicating the orientation of the pads, determines that pads are placed in an A-A position, the rescuer may be alerted by an output mechanism of the defibrillator or other resuscitation apparatus (e.g., monitor, CPR feedback system) that the pads are in the A-A position, and hence, only one of the motion sensors (e.g., anterior placed motion sensor) will be utilized to determine the depth of the chest compressions. The output mechanism of the defibrillator or other resuscitation apparatus (e.g., monitor, CPR feedback system) may also provide a recommendation to the user to use an A-P pad placement if the increased accuracy achieved by the use of two motion sensors is desired.

Though, in some embodiments, even when the system recognizes that the electrode pads are placed in the A-A position, the system may still elect to process data received from both motion sensors. That is, signals from the motion sensor placed closest to the sternum and the motion sensor held by the other pad would both be processed for chest compression depth. As an example, for A-A placed pads, the electrode pad placed on the side of the patient may be constructed such that the motion sensor extends far enough toward the back of the patient that the signals therefrom may be useable as a reference for making corrections in chest compression depth.

The system may recognize electrode assemblies to be placed in an A-A position when the separate motion sensors are oriented relative to one another at an angle greater than a threshold angle. For example, electrode assemblies oriented substantially perpendicular to one another may be considered to be in an A-A position. Conversely, it may be recognized that electrode assemblies are placed in an A-P position when the separate motion sensors are oriented relative to one another at an angle greater less than the threshold angle. Hence, electrode assemblies oriented substantially parallel to one another may be considered to be in an A-P position. In various embodiments, the threshold angle is about 30 degrees, about 40 degrees, about 50 degrees, or about 60 degrees.

The overall orientation of the patient may also be determined no matter what the orientation is of the sensor(s). For instance, even if one of the sensors is misplaced or tilted in an otherwise undesirable manner, the vertical axis of the patient (direction perpendicular to the surface of the chest) may be determined by comparing the movement and/or position of the two sensors relative to one another.

Figure 15:
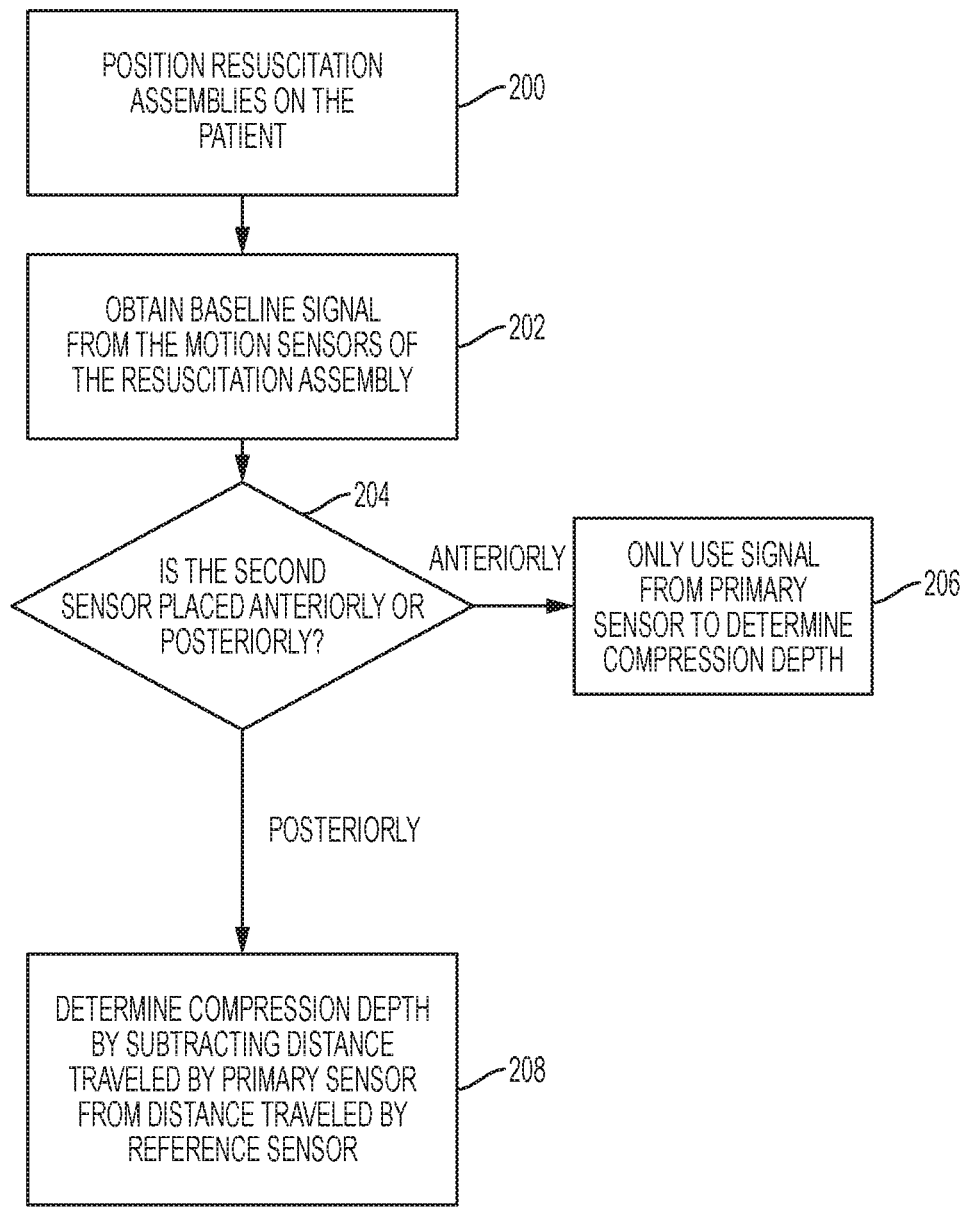
FIG. 15 is a flow chart of an exemplary process used for determining placement of the electrode assemblies of the resuscitation assembly and chest compression depths in accordance with some embodiments.

With reference to FIG. 15, an example of a process for determining chest compression depth using the resuscitation assembly of the present disclosure is discussed below. First, the rescuer positions the electrode assemblies 1A and 1B (placed in A-P position) or electrode assemblies 1A' and 1B' (placed in A-A position) on the patient (see block 200). Once the electrode assemblies are placed on the patient, a signal is obtained from each motion sensor 19 to provide a baseline acceleration of gravity (see block 202). By measuring the baseline acceleration of gravity, the system determines the initial orientation of each motion sensor of the electrode assemblies and rotates the reference sensor (i.e., motion sensor 19 of the electrode assembly positioned anteriorly or posteriorly) to the same plane as the primary sensor (i.e., motion sensor 19 positioned anteriorly on the patient's sternum). This process reduces errors caused by a non-parallel alignment of the primary and reference sensors. In addition, the baseline accelerations measured by the reference sensor can be used to determine whether the reference sensor was placed posteriorly or anteriorly (see block 204). If an anterior placement is used for the reference sensor (see the configuration of FIG. 12), the accelerations detected by the motion sensor 19 of resuscitation assembly 1B' (i.e., the reference sensor) are disregarded and compression depth is determined solely based on a signal from motion sensor 19 of electrode assembly 1A' (i.e., the primary sensor as discussed hereinabove (see block 206)). If a posterior placement is used for the reference sensor (see the configuration of FIGS. 1A and 1B), the chest compression depth is calculated by subtracting a distance traveled by the motion sensor 19 of the electrode assembly 1B (i.e., the secondary sensor) from a distance traveled by the motion sensor 19 of the electrode assembly 1A (i.e., the primary sensor) along the direction in which chest compressions are administered, as described hereinabove (see block 208).

Another use for resuscitation assemblies of the present disclosure in conjunction with defibrillator 5 is to accurately detect compression depth when performing CPR on smaller patients such as infants. For adults, CPR chest compressions are delivered while the patient is supine, typically supported by a sufficiently rigid surface (a floor, gurney, or hospital bed). For infants, on the other hand, CPR chest compressions may be provided with one of two methods, discussed below.

Figure 16:
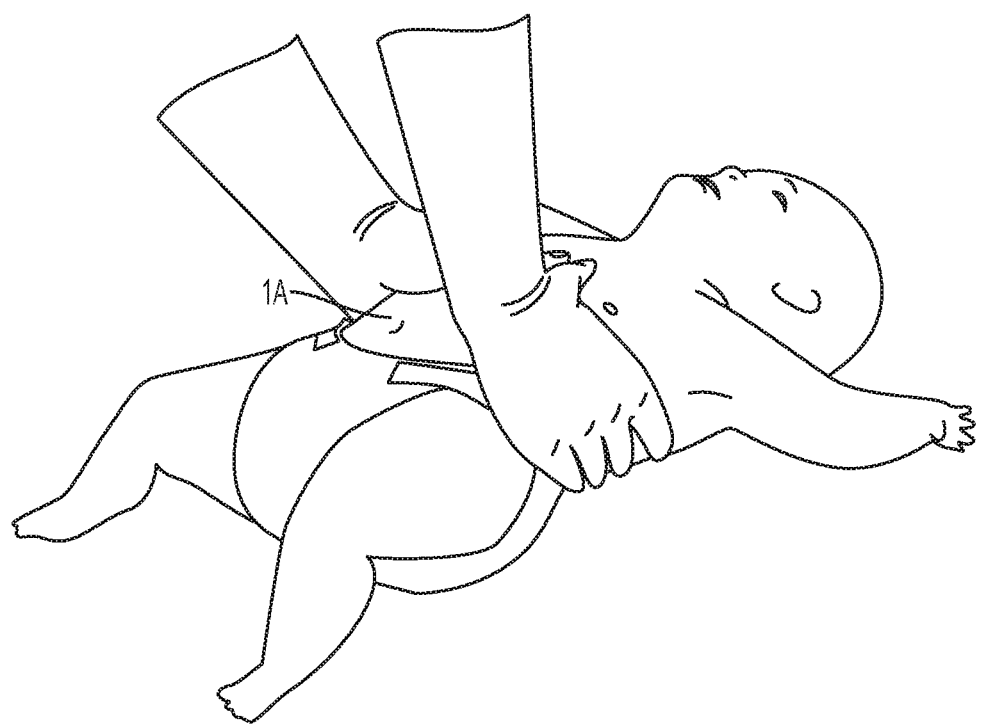
FIG. 16 illustrates the two-thumb technique for accomplishing CPR compressions on an infant utilizing a resuscitation assembly in accordance with some embodiments.

The first method for administering CPR chest compressions to an infant, which may be preferable in some instances, is the two-thumb method as shown in FIG. 16. This method entails grasping the infant's thorax with both hands, placing both thumbs over the sternum (with the fingers supporting the back of the infant) and using the thumbs to provide compressive force to the sternum. More specifically, the infant is supported on a surface in the supine position. A CPR provider places his/her hands around the infant's thorax, thereby placing his/her thumbs over the infant's sternum with his/her fingers wrapping over the axillary area under the infant's arms and around the infant's back. In this method, the CPR provider squeezes the infant's thorax, with the thumbs pressing on the sternum, to push the sternum toward the spine. These compressions should be accomplished at a rate of 100 compressions per minute and a depth of about one-third of the total thickness of the thorax (e.g., 1.5 inches (3.8 cm) for a thorax thickness of about 4.5 inches).

The second method for administering CPR chest compressions to an infant, which may be preferable for lone rescuers, is often referred to as the two finger method. This method entails compression of the infant's chest with two fingers placed over the inter-mammary line (superior to the xiphoid process). Compressions are generally recommended to be about one third of the thickness of the thorax (e.g., 1.5 inches (3.8 cm) for a thorax thickness of 4.5 inches (11.4 cm)), which is a rough estimate of infant chest thickness which is, of course, variable depending on the age/size of the infant patient). The chest should be released completely after each compression.

According to the American Heart Association, the two-thumb-encircling hands technique is preferred over the two-finger technique because the two-thumb technique has been suggested to give rise to higher coronary artery perfusion pressure, resulting more consistently in appropriate depth or force of compressions, and may generate higher systolic and diastolic pressures in the patient.

By positioning a motion sensor 19 on both the back and the chest of the infant through the use of electrode assemblies 1A and 1B, the compression depth of compressions performed on an infant using one of several techniques, such as the two-thumb, two finger and/or single palm (where a palm is placed underneath the patient as a backboard) technique can be accurately determined by placing the thumbs or fingers over the respective motion sensors and subtracting a distance traveled by the motion sensor 19 of the electrode assembly 1B from a distance traveled by the motion sensor 19 of the resuscitation assembly 1A. In some cases, the use of the two sensor configuration in the A-P position to estimate chest compression depth may be even more effective when using the two-thumb method because this method often involves squeezing of the patient between the thumbs and the fingers, resulting in movement both on the front and back. Though, it can be appreciated that the two sensor configuration may also be effective when using the two finger and/or single palm technique, particularly when the patient is lying on a compressible surface. In fact, the two sensor configuration may be effective as rescuers may switch between techniques (e.g., two-thumb, two finger, single palm, etc.).

By implementing a dual sensor approach in accordance with the present disclosure, the estimated chest compression depth may be compared with desired chest compression ranges (e.g., based on AHA/physician recommendations), and appropriate feedback and/or instructions can be provided to a rescuer as to the quality of chest compressions administered based on the comparison of estimated compression depth and desired compression ranges. Such feedback may include, for example, prompts that provide instruction(s) to the rescuer of whether to provide deeper or shallower compressions, or to maintain the current depth. Any appropriate prompts may be employed, such as audio prompts (e.g., voice/spoken cues, beeps of varying tone/pattern, etc.), visual (e.g., display screen with text, colors and/or graphics), tactile (e.g., vibrations), or prompts according to another suitable method. It should also be appreciated that while several of the embodiments described herein may apply to pediatric or small patients, such configurations may also apply, or may be more preferable, for adult or larger patients.

It can be appreciated that chest compression depth can be determined in a number of different ways utilizing the pair of motion sensors provided in the electrode assemblies of the resuscitation assembly described herein. For instance, raw acceleration signals may be subtracted and then processed (e.g., double integrated) to calculate net distance. Or, before subtraction, raw acceleration signals may be processed (e.g., double integrated) to yield distance values and then the respective distance values may be subtracted accordingly. In other examples, one or both of the motion sensors may be velocity or displacement sensors, and the signals obtained therefrom can be processed to determine chest compression depth or other chest compression parameters such as rate, release velocity, etc.

To further illustrate one of the above examples, one motion sensor, positioned on the back of the patient for example, provides a signal indicative of acceleration caused by external accelerations, such as the patient being transported, the patient being placed on a compressible surface, etc., and another motion sensor, positioned on the chest of the patient for example, provides a signal indicative of acceleration caused by a rescuer performing chest compressions on a patient. The signal indicative of the acceleration caused by compressions (the compression acceleration) is subtracted from the signal indicative of acceleration caused by the external accelerations (the external acceleration) to produce a corrected acceleration value (e.g., estimated actual acceleration). Once obtained, the corrected acceleration value may be double integrated to produce a corrected chest compression depth (e.g., estimated actual chest compression depth). Using such a method may be useful to save computational resources in that only one processing step is performed, i.e., the signal representing corrected acceleration is the only signal that is integrated, which may save processing steps. Further, the software and/or hardware component that performs the processing (e.g., integration) may only need to input a single acceleration value regardless of whether the acceleration signal(s) had previously been subtracted or processed in another manner.

Illustrating another example, the chest compression depth may be calculated by subtracting a distance traveled by the second motion sensor from a distance traveled by the first motion sensor. In such an instance, the signal indicative of acceleration caused by external accelerations is double integrated to determine the distance traveled by the second motion sensor and the signal indicative of acceleration caused by a rescuer performing chest compressions on a patient is double integrated to determine the distance traveled by the first motion sensor. The distance traveled by the second motion sensor is then subtracted from the distance traveled by the first motion sensor to provide the compression depth.

The resuscitation assemblies discussed herein may also be utilized to provide feedback to a user regarding the surface upon which a patient is placed. More specifically, the output device may provide instructions to a user for a surface upon which the patient is positioned to be changed based on information sensed from the motion sensor 19 of the electrode assembly 1A and the motion sensor 19 of the electrode assembly 1B. For example, and with reference to FIGS. 17 and 18, in operation, a user may place the electrode assemblies 1A and 1B in an A-P orientation with the electrode assembly 1A being positioned on the patient's sternum and the electrode assembly 1B being positioned on the patient's back as shown in FIGS. 1A and 1B (see block 400 of FIG. 18).

Once the electrode assemblies 1A, 1B of the resuscitation assembly are properly placed, they are operatively connected via cables 7 to a defibrillator 5 having control circuitry (not shown) and the output device, such as display 6 and/or a speaker (not shown), to provide output to a user. By way of example, and as discussed above, the output device provides information about patient status and CPR administration quality during the use of the defibrillator 5. The information about the chest compressions is automatically displayed in display 6 when compressions are detected. The information about the chest compressions displayed may include rate (e.g., number of compressions per minute) and depth (e.g., depth of compressions in inches or millimeters). The rate and depth of compressions can be determined by analyzing readings from the motion sensors 19.

It is common practice to place a patient on a sufficiently rigid surface (e.g., a floor, gurney, backboard, or hospital bed) prior to initiating chest compressions. However, if the patient is not provided on such a surface and is instead placed on a compressible surface (e.g., adults in hospitals are commonly treated on compressible surfaces, and mattresses for pediatric patients mattress can be especially compressible, even more so than adult mattresses), such as a soft mattress, the rescuer may need to perform more intense work to achieve the required compression depth. As a result, the rescuer may either have difficulty achieving sufficient compression depth and/or fatigue quickly. Or, without the feedback mechanism, the rescuer may have the impression of reaching a sufficient depth without actually achieving it.

Figure 17:
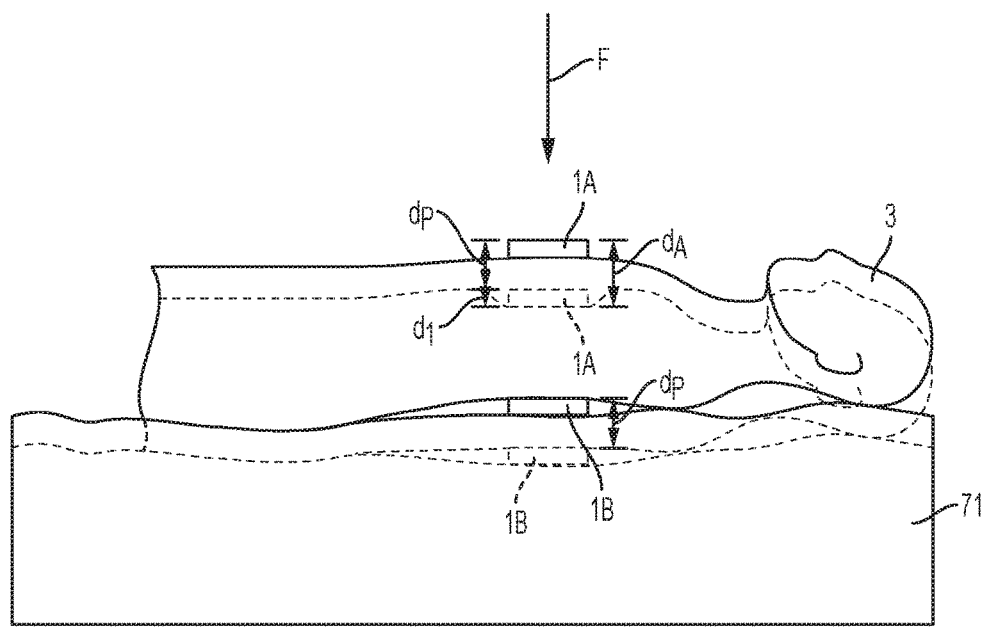
FIG. 17 is a side schematic view of compressions being applied to a patient utilizing a resuscitation assembly in accordance with some embodiments.

With reference to FIG. 17, a patient 3 is illustrated as being positioned on a compressible surface 71, such as a mattress, where an electrode assembly 1A having a motion sensor 19 is positioned anteriorly and an electrode assembly 1B having a motion sensor 19 is positioned posteriorly. In operation, chest compressions are performed on the patient 3 by a rescuer as denoted by arrow F. The measured displacement ($d_A$) obtained by motion sensor 19 of electrode assembly 1A includes not only the displacement of the compression into the chest ($d_1$) but also the displacement caused by deformation of the compressible surface ($d_P$). As discussed hereinabove, this can lead to an overestimation of compression depth. By providing a motion sensor in both the anteriorly positioned electrode assembly 1A and the posteriorly positioned electrode assembly 1B, this overestimation of the compression depth may be corrected to provide a more accurate determination of chest compression depth. The actual compression depth can be calculated by subtracting the displacement of the motion sensor 19 of the electrode assembly 1B (i.e., the secondary sensor) from the displacement of the motion sensor 19 of the electrode assembly 1A (i.e., the primary sensor). More specifically, the displacement of the motion sensor 19 of the electrode assembly 1A corresponds to displacement $d_A$ in FIG. 17 and includes both the displacement of the compression into the chest ($d_1$) and the displacement caused by deformation of the compressible surface ($d_P$). The displacement of the motion sensor 19 of the electrode assembly 1B only measures the displacement caused by deformation of the compressible surface ($d_P$). Accordingly, by subtracting the displacement caused by deformation of the compressible surface ($d_P$) from the displacement of the motion sensor 19 of the electrode assembly 1A ($d_A=d_1+d_P$), the actual compression depth, corresponding to displacement of the compression into the chest ($d_1$) can be obtained.

Figure 18:
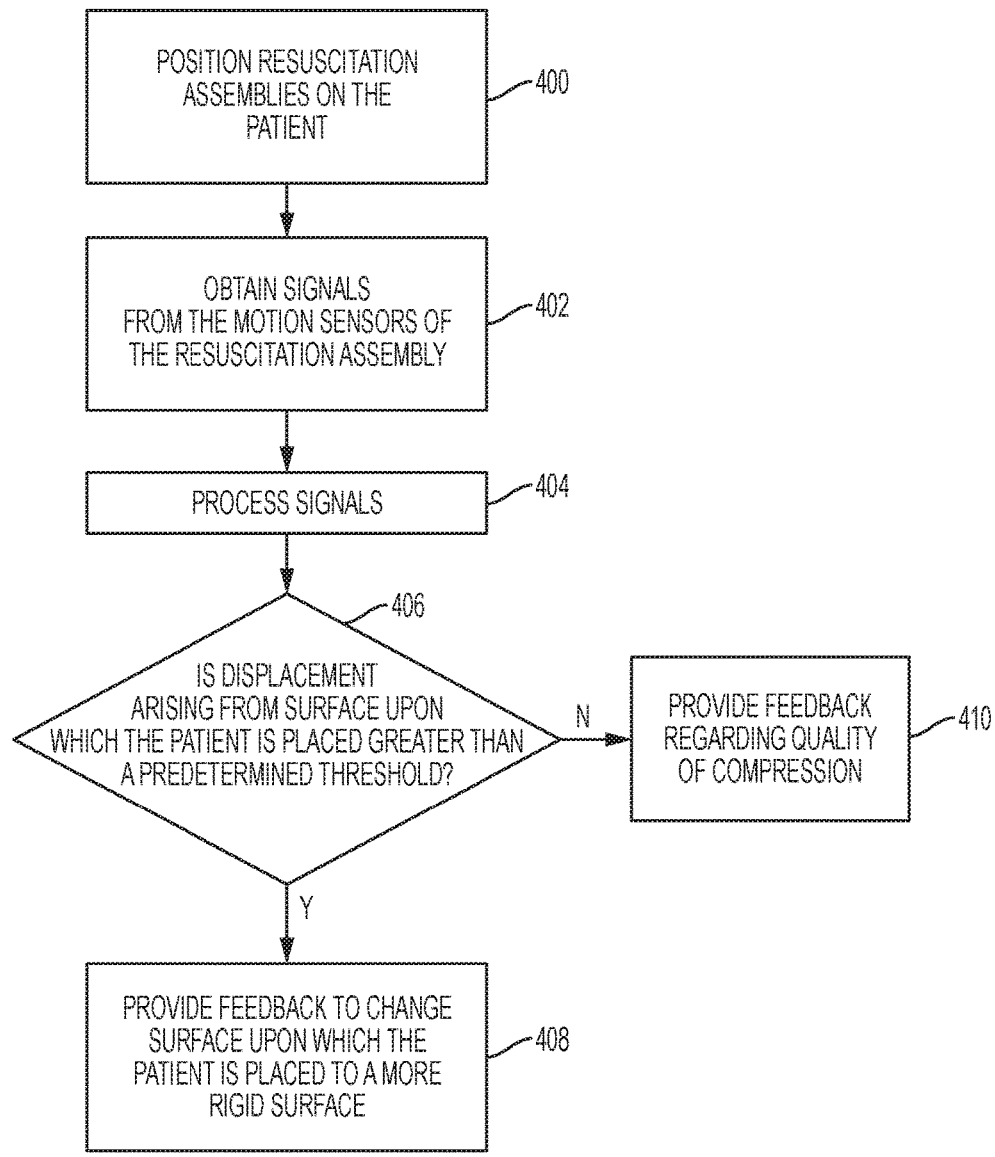
FIG. 18 is a flow chart of an exemplary process used for providing feedback to a rescuer regarding the surface upon which a patient is positioned in accordance with some embodiments.

In addition, with reference to FIG. 18, by incorporating a motion sensor 19 in both the anteriorly positioned electrode assembly 1A and the posteriorly positioned electrode assembly 1B, a motion sensor 19 is provided on both the chest and back of the patient 3. The control circuitry of the defibrillator 5 is operatively connected to and programmed to receive and process signals from the motion sensors 19 of the electrode assemblies 1A and 1B and may determine whether the patient 3 is positioned on a compressible surface. More specifically, the motion sensor 19 of the electrode assembly 1A may produce a first signal representative of acceleration caused by compressions and the motion sensor 19 of the electrode assembly 1A may produce a second signal representative of other types of accelerations, such as acceleration due to movement on a compressible surface (see block 402). These signals are then processed (see block 404) to determine whether the amount of displacement arising from the compressible surface meets a threshold great enough to recommend that the surface underneath the patient be changed (see block 406). Such a threshold may be correlated to the amount of work that a rescuer would have to exert to achieve chest compressions that fall within a desired range. For example, to alleviate the rescuer of excess effort, a threshold may be set such that if the displacement arising from the compressible surface is greater than 10% (e.g., between 10-100%), greater than 25% (e.g., between 25-100%), greater than 50% (e.g., between 50-100%), greater than 75%, or greater than 100% of the recommended compression depth or another metric (e.g., comparison to the total displacement of the anterior sensor), then the user may be provided with a suggestion or instruction that the underlying surface on which the patient resides be changed. Such an instruction may be for a backboard to be placed underneath the patient, or for the patient to be moved from the existing relatively soft surface to a harder surface. The output device of the defibrillator 5 may provide feedback instructions to a user for a surface upon which the patient 3 is positioned to be changed if it is determined that the patient 3 is provided on a compressible surface that meets the set threshold (see block 408 of FIG. 18). This feedback can be real-time feedback in the form of an audible, visual or tactile indication requesting that the rescuer position a backboard beneath the patient 3 or move the patient 3 to a more rigid surface. Alternatively, the feedback may be issued at the end of the rescue sequence advising the rescuer to use a backboard in future CPR situations. In situations where displacement arising from a surface upon which the patient 3 is placed is less than the predetermined threshold, the system assumes the patient 3 is positioned on a rigid surface and the defibrillator 5 provides feedback to the rescuer regarding the quality of compressions as discussed hereinabove.

One challenge in using two motion sensors such as motion sensors 19 of electrode assemblies 1A and 1B or 1A' and 1B', for example, is that the two sensors may not be in the same orientation. By measuring acceleration in three dimensions, when the motion sensors 19 are configured as three-axis accelerometers, it is possible to determine a baseline orientation of each motion sensor 19 and then rotate the reference sensor (i.e., the motion sensor 19 of the resuscitation assembly 1B) to be in the same plane as the primary sensor (i.e., the motion sensor 19 of the resuscitation assembly 1A). It can be appreciated that this reference rotation may be applied to signals derived from both motion sensors using techniques known to those of ordinary skill in the art.

For certain cases, the rotation of a baseline vector of each motion sensor 19 may be determined by averaging a quiet period with no movement. From these vectors the angles ($\alpha$, $\beta$, $\gamma$) between the primary and reference sensors are calculated. A rotation matrix is then calculated to first rotate the reference vector around the Z-axis by an angle $\gamma$ (see Equation 1 below) and then rotate the vector again around the X-axis by an angle $\alpha$ (see Equation 2 below). Each measurement on the reference sensor is multiplied by the rotation matrix $R_x R_z$.

$$R_z = \begin{bmatrix} \cos(\gamma) & -\sin(\gamma) & 0 \\ \sin(\gamma) & \cos(\gamma) & 0 \\ 0 & 0 & 1 \end{bmatrix} \quad \text{Equation 1}$$

$$R_x = \begin{bmatrix} 1 & 0 & 0 \\ 0 & \cos(\alpha) & -\sin(\alpha) \\ 0 & \sin(\alpha) & \cos(\alpha) \end{bmatrix} \quad \text{Equation 2}$$

After the rotation is performed, the compression depth is calculated using the acceleration component as measured in the direction perpendicular to the chest surface (e.g., y-axis acceleration) from the primary and reference sensor. The depth is calculated by subtracting the acceleration in the direction perpendicular to the chest surface as detected by the motion sensor 19 of the resuscitation assembly 1B placed posteriorly on the patient 3 from the acceleration in the direction perpendicular to the chest surface as detected by the motion sensor 19 of the electrode assembly 1A placed anteriorly on the patient 3.

Alternatively, a rotation calibration may be performed via a normalized cross product calculation, such as that described in the journal article by Emod Kovacs, entitled "Rotation about an arbitrary axis and reflection through an arbitrary plane," published in Annales Mathematicae et Informaticae (40), 2012, pp. 175-186. In this method, to perform the rotation calibration, the baseline vector of each sensor is determined by averaging a quiet period with no movement. To rotate one vector to another, the vectors are first transformed so the axis of rotation is coordinate with the Z-axis. A rotation around the Z-axis of the angle between the two vectors is then performed and the inverse of the transformation is applied to the vectors. The axis of rotation is the normalized cross product of the reference sensor vector and the primary sensor vector.

Upon suitable calibration, the two motion sensors 19 may also be used to detect the direction in which chest compressions are administered such that a determination of whether a rescuer is performing compressions at an angle relative to the motion sensor 19 of a resuscitation assembly placed on the thorax can be made by the control circuitry. It may be preferable for chest compressions to be administered in a vertical direction relative to the patient (when lying down), i.e., substantially perpendicular to the surface of the chest. However, rescuers administering chest compressions may have a tendency to push at an angle relative to the vertical direction, for example, due to poor CPR habits/education, fatigue, etc.

Accordingly, whether placed in an A-P configuration or an A-A configuration, a resuscitation system incorporating motion sensors in multiple electrode assemblies may be configured to sense the angle at which the rescuer is pushing relative to the patient, and advise as to whether the rescuer should alter the direction in which chest compressions are being administered. For example, if the rescuer is administering chest compressions at a 45 degree angle relative to the vertical direction (perpendicular to the chest), then a first motion sensor (placed on the patient's chest) may be expected to move along a direction angled at approximately 45 degrees with respect to the vertical, as referenced by the second motion sensor (placed on the patient's back or side). Or, the manner in which the rescuer administers chest compressions, if delivered at a non-vertical angle relative to the patient, may cause the first motion sensor to tilt or roll. For cases where the angle at which chest compressions is determined based on the tilt or roll of a motion sensor, gyroscopes may be appropriately incorporated and the correction algorithm may account for the detected tilt or roll of the motion sensor. Hence, the resuscitation system may detect or otherwise estimate the angle at which chest compressions are being delivered.

As a result, based on the acceleration information gathered from the two sensor arrangement, the system may provide instructions to the rescuer to alter the manner and/or direction in which chest compressions are being delivered so as to minimize or otherwise reduce the angle of compression. Such instructions may be provided in the form of audio, visual, tactile feedback, or a combination thereof. As an example, the system may present a display screen or interface to the rescuer of the existing angle of compressions, as estimated via the dual motion sensor configuration. The display screen or interface may then provide an indication to the user that the direction in which chest compressions is delivered should be changed and how that change in direction may be accomplished. For example, the system may present a graphical display of the angle of chest compressions in real-time so that the rescuer may know how the direction of chest compressions should be immediately altered. Or, the system may provide express instructions to the rescuer for how the angle at which chest compressions are delivered should be altered. Or, upon sensing the misalignment in the direction of chest compressions, if the rescuer does not change the direction of compression, the system may instruct the rescuer to push harder so that the chest compressions will be deep enough. Another type of feedback might be providing an alert or other notification informing the rescuer that more work is being performed than necessary.

In yet another example, the motion sensors 19 of resuscitation assemblies in accordance with the present disclosure may be used to sense a rate of ventilations for a patient. More specifically, ventilations (manual or automated) administered to the patient, in between and/or appropriately synchronized between chest compressions, may cause movement of the patient's body. Such movements arising due to the ventilations may be detectable by the motion sensors of the resuscitation assemblies (e.g., anterior sensor may detect ventilation-induced movements), giving rise to a waveform (e.g., displacement as a function of time) representative of back and forth movement of the motion sensors. The frequency of peaks and valleys may provide an indication of the rate of ventilations delivered to the patient. Accordingly, the system with which the resuscitation assemblies are in communication may provide suitable indication and/or feedback (e.g., audio, visual, tactile) as to whether the rate of ventilations should be faster or slower, or how the ventilations may be better synchronized with chest compressions.

In still another example, as discussed hereinabove, the motion sensors 19 of resuscitation assemblies in accordance with the present disclosure may be used to determine whether the electrode assemblies are placed in an A-A, A-P or lateral-lateral position based on the orientation of the motion sensors 19 and/or distance relative to one another. Once the position of the electrode assemblies is determined, the system may adjust one or more resuscitation parameters, e.g., feedback and/or information provided to the rescuer.

With reference to FIG. 19, a resuscitation assembly 500 comprises a first electrode assembly 502, a second electrode assembly 504, and a CPR pad 506 associated with the first electrode assembly 502. In various embodiments, each of the electrode assemblies 502, 504 may have a motion sensor 19 incorporated therewith (e.g., motion sensor may be embedded within a portion of the electrode assembly). Electrode assemblies 502, 504 may be placed in an A-A position with electrode assembly 502 positioned on an upper right side of a chest of the patient 3 between the shoulder and the sternum and the electrode assembly 504 positioned on a lower left side of the chest of the patient 3 over lower ribs of the patient 3.

Figure 20A:
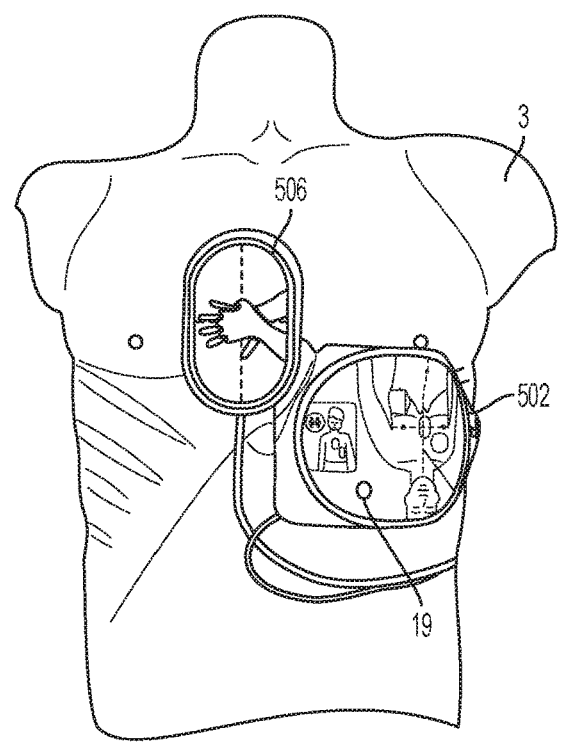
FIGS. 20A and 20B illustrate an alternative placement of the resuscitation assembly of FIG. 19 in accordance with the present disclosure on a cardiac arrest victim.
Figure 20B:
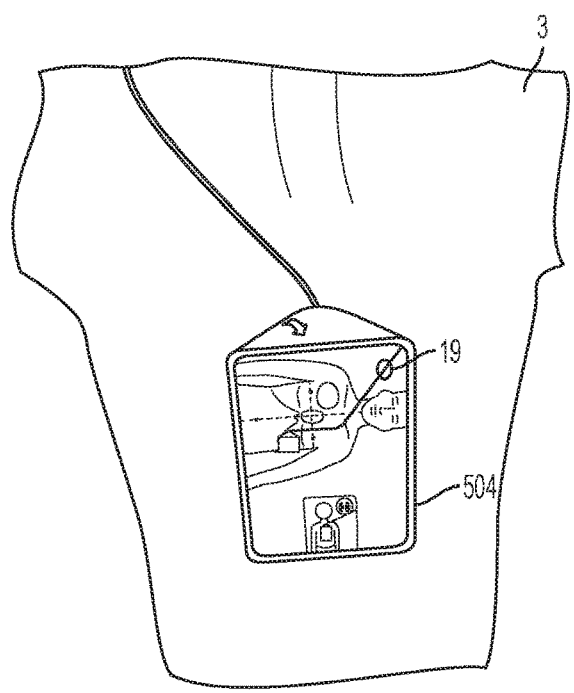

In certain forms of treatment, rather than placement in the A-A position shown in FIG. 19, a rescuer may place the first electrode assembly 502 and the second electrode assembly 504 in an A-P position. In some cases, placement of electrode assembly 502 on the patient's sternum area (as may happen during a rescue) and electrode assembly 504 on the patient's back may lead to an ECG signal that appears inverted and/or the pacing vector associated with the electrode placement may be oriented in an undesirable direction through the heart. In such instances, when electrode assemblies are placed in an A-P position as shown in FIGS. 20A and 20B, or other configuration that may lead to an inverted ECG signal and/or pacing vector oriented in an undesirable direction, the system may be configured to provide desirable corrections to the ECG signal and/or pacing vector to orient it in the preferred direction. Or, the system may prompt the rescuer to place the pads in an orientation that gives rise to a more intuitive ECG signal and/or pacing vector with preferred directionality.

By providing the electrode assemblies 502, 504 with motion sensors 19, the control circuitry used in the defibrillator 5 can be configured to determine the location of each of the electrode assemblies 502, 504 based on the orientation of the motion sensors 19 and/or distance relative to one another as described hereinabove. If the control circuitry determines that first electrode assembly 502 is positioned on the patient's sternum and the electrode assembly 504 on the patient's back as shown in FIGS. 20A and 20B based on the signals from the motion sensors 19, for some embodiments, the control circuit can invert or otherwise adjust the ECG signal such that it is displayed correctly on the display 6 of the defibrillator 5 and adjust the pacing vector (e.g., reverse the direction of the pacing vector) such that it is provided in the correct direction.

While various examples and configurations of the electrode assemblies incorporating motion sensors have been described hereinabove, this is not to be construed as limiting the present disclosure as various other examples and configurations have been envisioned in which each of the electrode assemblies includes at least one motion sensor. For instance, various other configurations have been envisioned for use with pediatric patients, infant patients, and adult patients.

Figure 21A:
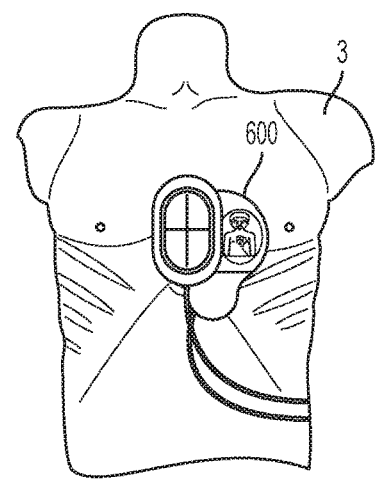
FIGS. 21A and 21B illustrate placement of an example of a resuscitation assembly in accordance with the present disclosure on a cardiac arrest victim.
Figure 21B:
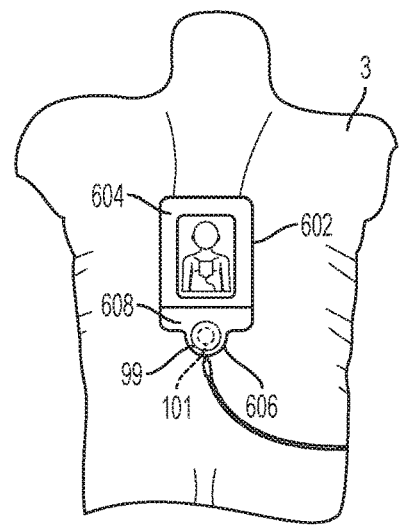

With reference to FIGS. 21A and 21B, a resuscitation assembly for use with a pediatric patient is illustrated. This resuscitation assembly includes a pair of electrode assemblies 600, 602. Electrode assembly 600 is configured to be attached anteriorly to the pediatric patient's chest and is similar in construction as electrode assembly 1A described hereinabove. Electrode assembly 602 is configured to be attached posteriorly to a patient's back (see FIG. 21B). The electrode assembly 602 may include a flexible electrode pad 604 having a therapy side (not shown) configured to be coupled to the patient 3 and substantially conform to the patient's anatomy. The therapy side includes conductive material (not shown), facing toward the body of the patient 3, adapted to provide therapeutic treatment to the patient.

The electrode assembly 602 may further include a motion sensor 101 positioned within a sensor casing 99. The motion sensor 101 and sensor casing 99 may be similar to the motion sensor 101 and sensor casing 99 shown in FIG. 10. The sensor casing 99 may be coupled to the electrode pad 604 by positioning the sensor casing 99 on an upper surface of the electrode pad 604 at a bottom extension portion 606. The extension portion 606 may form a pouch or other receptacle within which the sensor casing 99 may be disposed. In some embodiments, the sensor casing 99 is optionally removable from the pouch, and may be placed at any suitable location on or near the patient. A securing portion 608 may be positioned over the sensor casing 99 to secure the sensor casing 99 on the upper surface of the electrode pad 604 at the bottom extension portion 606. In such a configuration, the sensor casing 99 may be removably secured between the upper surface of the bottom extension portion 606 and the bottom surface of the securing portion 608, thereby allowing the sensor to be easily replaced and/or moved to another location.

It can be appreciated that the sensor casing and the electrode pad may be removably coupled by any suitable manner. As discussed above, the electrode pad may have a pouch or receptacle for holding the sensor casing in place, yet the sensor casing may be easily separated therefrom when desired. In one example, the backing of the electrode pad may have perforations, a slightly scored or nicked region, cut marks, etc. that allow for tearing of a weakened region so that the sensor may be removed. The electrode pad may further include a suitable adhesive so that the sensor may be reattached or coupled thereto. In another example, the sensor may be adhered to an upper surface of the electrode pad backing where the backing includes a liner material such that the sensor may be peeled off and adhered elsewhere. Alternatively, the sensor casing and the electrode pad may have complementary coupling components, for example, hook and loop fasteners, mutually attracting magnets, other fastening elements, etc. Or, the sensor casing may have an adhesive material that allows for repositioning from the electrode pad to a different surface (e.g., patient's skin). In further embodiments, the adhesive for attaching the sensor to the electrode pad and/or surface of the patient may be effective in moist environments, such as in neonatal situations where birthing fluid is present. For example, a moisture activated or water-based adhesive may be employed such that when the sensor casing is peeled off the pad and reattached, the adhesive is more effective in adhering to the point of contact.

Figure 22:
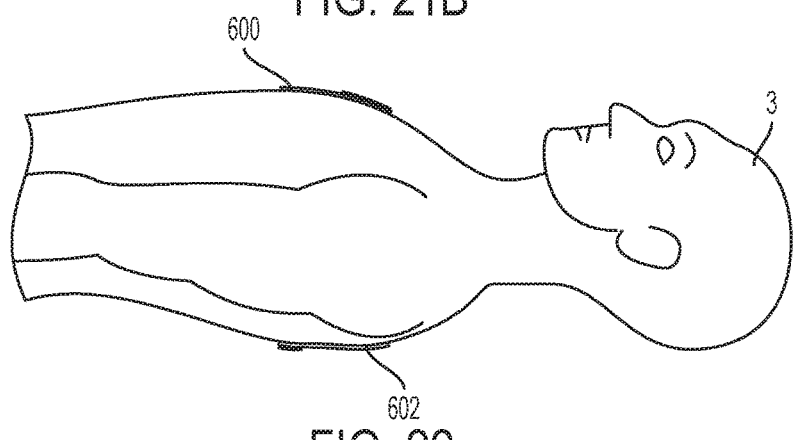
FIG. 22 is a side view of the electrode assembly of the resuscitation assembly of FIG. 21B.

In addition, by utilizing a motion sensor 101 and sensor casing 99 having a low profile such as the one shown in FIG. 10 and positioning the sensor casing at a bottom extension portion 606 of the electrode pad 604, the remaining portions of the flexible electrode pad 104 have more flexibility in adhering to the patient 3, thereby reducing the likelihood that the electrode pad 604 lifts off from the patient 3. With reference to FIG. 22, the flexible electrode pad 104 may also be configured to be significantly thinner than the electrode assembly 1A shown in FIG. 1. For instance, the thickness of the flexible electrode pad may be less than approximately 10 cm, less than approximately 5 cm (e.g., approximately 1 mm-5 cm), less than approximately 1 cm (e.g., approximately 1-10 mm), less than approximately 5 mm (e.g., approximately 0.1-5 mm), less than approximately 4 mm (e.g., approximately 0.1-4 mm), less than 3 mm (e.g., approximately 0.1-3 mm), less than approximately 2 mm (e.g., approximately 0.1-2 mm), less than approximately 1 mm (e.g., approximately 0.1-1 mm), or may fall within another appropriate range.

Figure 23A:
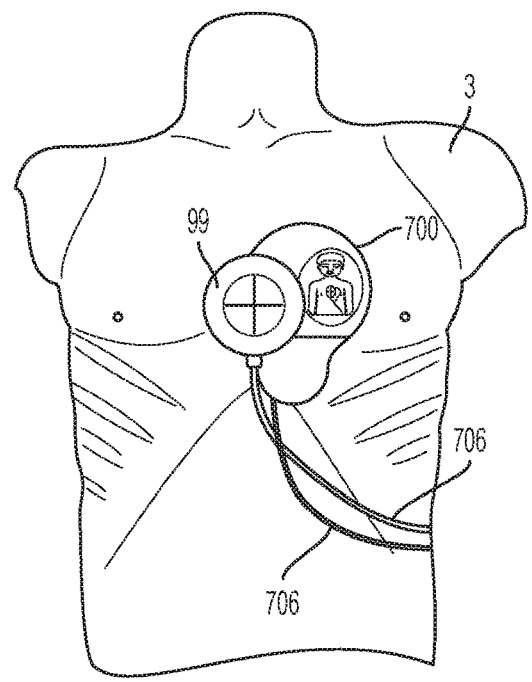
FIGS. 23A and 23B illustrate placement of an example of a resuscitation assembly in accordance with the present disclosure on a cardiac arrest victim.
Figure 23B:
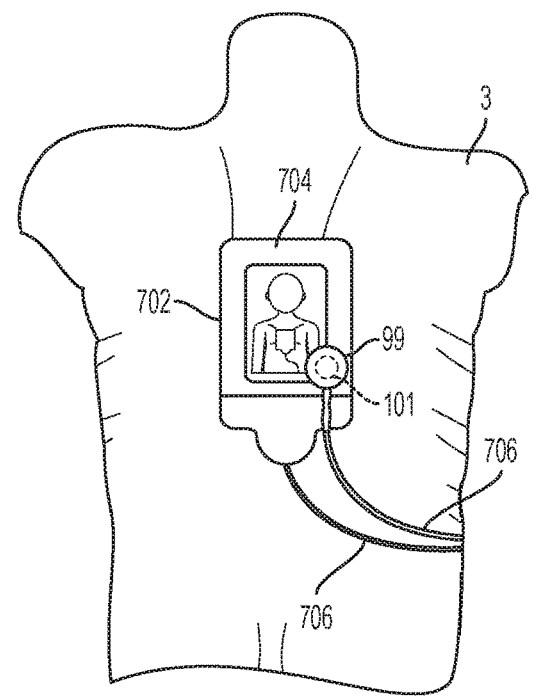

With reference to FIGS. 23A and 23B, another example of a resuscitation assembly for use with a pediatric patient is illustrated. In this example, the resuscitation assembly includes a pair of electrode assemblies 700, 702. Electrode assembly 700 is configured to be attached anteriorly to the pediatric patient's chest and is substantially the same as electrode assembly 1A described hereinabove except that the motion sensor incorporated therein is a smaller motion sensor such as the motion sensor 101 incorporated into sensor casing 99 as shown in FIG. 10. The use of such a motion sensor is beneficial for use in pediatric patients in that it is smaller and therefore takes up less space on the patient's anatomy. Electrode assembly 702 is configured to be attached posteriorly to a patient's back (see FIG. 23B). The electrode assembly 702 may include a flexible electrode pad 704 having a therapy side (not shown) configured to be coupled to the patient 3 and substantially conform to the patient's anatomy. The therapy side includes conductive material (not shown), facing toward the body of the patient 3, adapted to provide therapeutic treatment to the patient.

As shown in this example, the motion sensor 101 associated with the electrode assembly is not integrated into a padding. Instead, the electrode assembly 702 and motion sensor 101 are separate from one another, yet may each be connected to the overall system (e.g., via cables 706 or wireless connection). In some embodiments, the sensor casing 99 containing the motion sensor 101, where the sensor casing 99 is provided as a small protective covering (e.g., without foam padded material), may be coupled to a patient, separate from the remainder of the electrode assembly 702. As an example, the sensor casing 99 and/or motion sensor 101 may include an adhesive or other material that allows the sensor to be attached to and detached from the electrode pad and/or the body, apart from the electrode pad. In addition, in such an example, the sensor casing 99 may be attached to various locations on the electrode pad 704 as shown in FIG. 23B. As an example, the sensor casing 99 may be initially adhered to the electrode pad 704, and then may be removable for subsequent attachment to the body of the patient.

Such a configuration, as shown in FIG. 23B, where motion sensor 101 can be freely attached to and detached from the body separate from the electrode pad 604 may be relevant if it is preferable for the location of compressions to vary, or if it is otherwise desirable for the motion sensor to be positioned at a location away from the electrode pad.

Figure 24A:
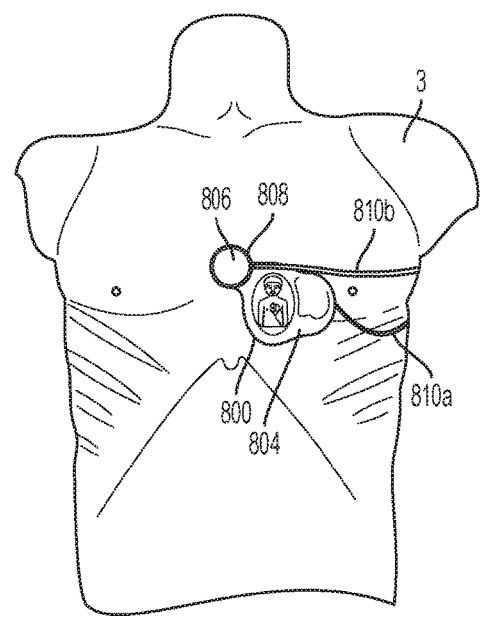
FIGS. 24A and 24B illustrate placement of an example of a resuscitation assembly in accordance with the present disclosure on a cardiac arrest victim.
Figure 24B:
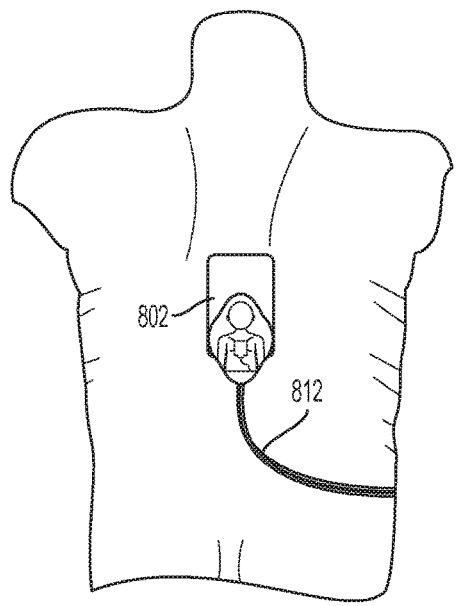

With reference to FIGS. 24A and 24B, another example of a resuscitation assembly for use with a pediatric patient is illustrated. This resuscitation assembly includes a pair of electrode assemblies 800, 802. Electrode assembly 800 is configured to be attached anteriorly to the pediatric patient's chest and comprises a flexible electrode pad 804 having a therapy side (not shown) configured to be coupled to the patient 3 and substantially conform to the patient's anatomy. The therapy side includes conductive material (not shown), facing toward the body of the patient 3, adapted to provide therapeutic treatment to the patient. The electrode assembly 800 may further include a motion sensor 806 positioned within a sensor casing 808. The motion sensor 806 and sensor casing 808 may be similar to the motion sensor 101 and sensor casing 99 shown in FIG. 10. The sensor casing 808 may be coupled to the electrode pad 804 by positioning the sensor casing 808 on an upper surface of the electrode pad 804. As discussed herein, the outer surface of the sensor casing 808 may include a texture or other material to prevent slippage of the rescuer's hands or otherwise enhance overall comfort during compressions. In addition, the lead wires 810*a*, 810*b* extending from the electrode pad 804 and the sensor casing 808, respectively, are configured to extend from the side of these elements rather than from the bottom as in other examples. Such a configuration may be desirable if a rescuer wants to direct the wires away from the abdomen of a patient. For example, if a patient has had abdominal surgery, with wounds in an area where wires, tubes or other instruments would be located, in close proximity with conventional electrodes, it may be advantageous to utilize an electrode assembly, such as electrode assembly 804, with the wires 810*a*, 810*b* extending to the side away from the wound location. In addition, the side extending wires may more easily lead toward a defibrillator, monitor or other computing system for processing signals from the sensor. Otherwise, sensor wires extending down toward the abdomen, as may typically be the case, may be comparatively more cumbersome to handle. The posterior electrode pad may also include side extending wires, which are generally useful to reduce the overall contact area with the patient, and for smaller patients where space on the patient's back is limited.

Figure 24C:
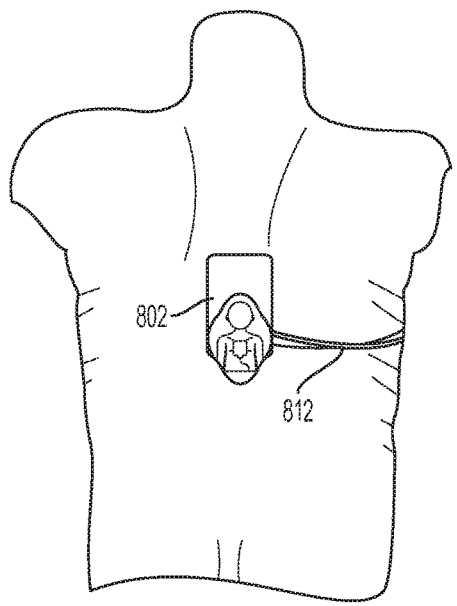
FIG. 24C illustrates placement of a posterior electrode assembly having an alternative example of a lead wire than the posterior electrode of FIG. 24B.

Electrode assembly 802 is configured to be attached posteriorly to a patient's back (see FIG. 24B). The electrode assembly 802 is substantially similar in construction as electrode assembly 602 shown in FIG. 21B except that the dimensions of the electrode assembly 802 are smaller and more streamlined. The lead wire 812 is configured to extend from the bottom of the electrode assembly 802 as shown in FIG. 24B. Alternatively, as shown in FIG. 24C, the lead wire 812 may extend from the side of the electrode assembly 802 for the reasons described hereinabove with reference to FIG. 24A.

With reference to FIGS. 25A and 25B, a resuscitation assembly for use with an adult patient is illustrated. This resuscitation assembly includes a pair of electrode assemblies 900, 902. Electrode assembly 900 is configured to be attached anteriorly to the pediatric patient's chest and is substantially similar in construction as electrode assembly 1A described hereinabove except that the shape of the electrode pad 904 is triangular rather than round. Electrode assembly 902 is configured to be attached posteriorly to a patient's back (see FIG. 25B). The electrode assembly 902 is substantially similar in construction as electrode assembly 1B described hereinabove except that the sensor housing 13 is positioned at an upper corner of the flexible electrode pad 906 rather than covering most of the surface of the flexible electrode pad.

With reference to FIGS. 26A and 26B, another example of a resuscitation assembly for use with an adult patient is illustrated. This resuscitation assembly includes a pair of electrode assemblies 1000, 1002. Electrode assembly 1000 is configured to be attached anteriorly to the adult patient's chest and is substantially the same as electrode assembly 700 described hereinabove except that the shape of the electrode assembly 1000 is triangular rather than round and the electrode assembly 1000 has larger dimensions. Electrode assembly 902 is configured to be attached posteriorly to a patient's back (see FIG. 25B). The electrode assembly 902 is substantially similar in construction as electrode assembly 600 described hereinabove except that it has larger dimensions. In some embodiments, such pads may include ECG electrodes, which allow for monitoring of ECG without requiring separate leads for pacing. In addition, the sensor casings 99 of each of these electrode assemblies 1000 and 1002 are removable and adjustable. For example, a rescuer may be able to remove the sensor casing 99 of the anterior electrode assembly 1000 from the primary position shown in FIG. 26A to some other location. If the patient has a surgical wound, it may be necessary to leave the sensor casing near the sternum but move the electrode pad of the electrode assembly 1000 to a different location.

Figure 27A:
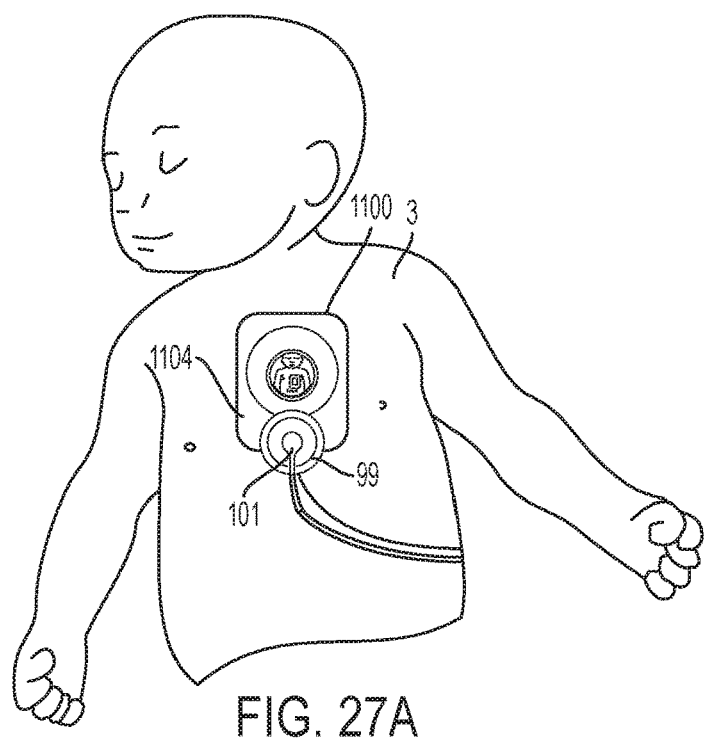
FIGS. 27A and 27B illustrate placement of an example of a resuscitation assembly in accordance with the present disclosure on a cardiac arrest victim.
Figure 27B:
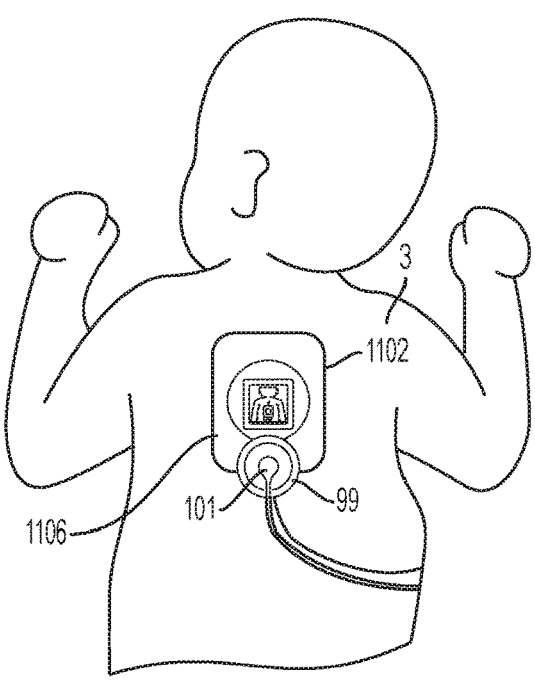

With reference to FIGS. 27A and 27B, an example of a resuscitation assembly for use with neonatal patients is illustrated. This resuscitation assembly is designed specifically for use on an infant during CPR procedures as was described with reference to FIG. 16. The resuscitation assembly comprises a pair of electrode assemblies 1100, 1102. Electrode assembly 1100 is configured to be attached anteriorly to the pediatric patient's chest. The electrode assembly 100 may include a flexible electrode pad 1104 having a therapy side (not shown) configured to be coupled to the infant patient 3 and substantially conform to the patient's anatomy. The therapy side includes conductive material (not shown), facing toward the body of the infant patient 3, adapted to provide therapeutic treatment to the patient. The electrode assembly 1100 may further include a motion sensor 101 positioned within a sensor casing 99. The motion sensor 101 and sensor casing 99 may be similar to the motion sensor 101 and sensor casing 99 shown in FIG. 10. The sensor casing 99 may be coupled to the electrode pad 1104 by positioning the sensor casing 99 on an upper surface of the electrode pad 1104 at a bottom portion thereof.

Electrode assembly 1102 is configured to be attached posteriorly to a patient's back (see FIG. 27B). The electrode assembly 1102 may include a flexible electrode pad 1106 having a therapy side (not shown) configured to be coupled to the infant patient 3 and substantially conform to the patient's anatomy. The therapy side includes conductive material (not shown), facing toward the body of the infant patient 3, adapted to provide therapeutic treatment to the patient. The electrode assembly 1102 may further include a motion sensor 101 positioned within a sensor casing 99. The motion sensor 101 and sensor casing 99 may be similar to the motion sensor 101 and sensor casing 99 shown in FIG. 10. The sensor casing 99 may be coupled to the electrode pad 1106 by positioning the sensor casing 99 on an upper surface of the electrode pad 1106 at a bottom extension thereof.

Although a dual motion sensor resuscitation assembly has been described in detail for the purpose of illustration based on what is currently considered to be the most practical examples, it is to be understood that such detail is solely for that purpose and that the invention is not limited to the disclosed examples, but, on the contrary, is intended to cover modifications and equivalent arrangements. For example, it is to be understood that this disclosure contemplates that, to the extent possible, one or more features of any example can be combined with one or more features of any other example.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless otherwise indicated, all numbers expressing dimensions, material parameters, or other values used in the specification and claims modified by the term "about" or "approximately" are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

As used herein, the term "about" or "approximately" when referring to a measurable value such as an amount, dimension, material parameter, and the like, is meant to encompass variations of +/−10%, more preferably +/−5%, even more preferably, +/−1%, and still more preferably +/−0.1% from the specified value, as such variations are appropriate to perform the disclosed methods.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing and tolerance measurements. Every numerical range given throughout this specification will include every narrower numerical range that falls within such broader numerical range, as if such narrower numerical ranges were all expressly written herein.

What is claimed is:

1. A system for facilitating resuscitation, comprising:
a resuscitation assembly comprising:
  a first electrode assembly comprising a therapy side configured to sense ECG signals and deliver a therapeutic shock and a first motion sensor,
  a second electrode assembly comprising a therapy side configured to sense ECG signals and deliver a therapeutic shock and a second motion sensor and an identification component associated with the resuscitation assembly;
processing circuitry operatively connected to the resuscitation assembly and configured to
  identify the resuscitation assembly as one of a pediatric or adult resuscitation assembly based on an identification signal produced by the identification component,
  receive and process signals from at least one of the first and second motion sensors to estimate at least one of a compression depth and rate during administration of chest compressions, and
  receive and process ECG signals from the first and second electrode assemblies and deliver electrotherapy through the first and second electrode assemblies; and
an output device for providing one or more chest compression parameters including at least one of the estimated compression depth and the estimated compression rate for a user,
wherein the output device is configured to adjust presentation of the one or more chest compression parameters based on whether the resuscitation assembly is identified as pediatric or adult, and
wherein the processing circuitry is configured to compare at least one of the estimated compression depth and the estimated compression rate to a desired range, and the output device is configured to display at least one of the estimated compression depth and the estimated compression rate and provide chest compression prompting for the user when the resuscitation assembly is identified as adult and the output device is configured to display at least one of the estimated depth and the estimated rate without providing chest compression prompting for the user when the resuscitation assembly is identified as pediatric.

2. The system of claim 1, wherein the processing circuitry is configured to determine a placement orientation of the first electrode assembly and the second electrode assembly on a patient based on a signal from at least one of the first motion sensor and the second motion sensor.

3. The system of claim 2, wherein the processing circuitry is configured to determine whether the first electrode assembly is positioned on a first portion of the patient's anatomy based on a signal from the first motion sensor and whether the second electrode assembly is positioned on a second portion of the patient's anatomy in an anterior-posterior orientation based on a signal from the second motion sensor.

4. The system of claim 2, wherein the processing circuitry is configured to determine whether the first electrode assembly is positioned on a first portion of the patient's anatomy based on a signal from the second motion sensor and whether the second electrode assembly is positioned on a second portion of the patient's anatomy in an anterior-anterior orientation based on a signal from the second motion sensor.

5. The system of claim 2, wherein the processing circuitry is configured to:
at least one of display on the output device the ECG signal and determine an orientation of a pacing vector; and
adjust at least one of the displayed ECG signal and the pacing vector based on the determined placement orientation of the first electrode assembly and the second electrode assembly.

6. The system of claim 1, wherein at least one of the first motion sensor and the second motion sensor is separable from the respective first or second electrode assembly.

7. The system of claim 1, wherein the estimated chest compression depth is calculated by subtracting a distance traveled by the second motion sensor from a distance traveled by the first motion sensor.

8. The system of claim 1, wherein the first motion sensor is configured to produce a first signal representative of acceleration caused by compressions and the second motion sensor is configured to produce a second signal representative of acceleration due to movement on a compressible surface.

9. The system of claim 1, wherein the processing circuitry and the output device are provided in an external defibrillator.

10. The system of claim 1, wherein the identification component comprises at least one of a memory and a resistor from which the identification signal is based and the processing circuitry is configured to adjust a shock algorithm based on the identification of the resuscitation assembly as pediatric or adult.

11. The system of claim 1, wherein at least one of the first electrode assembly and the second electrode assembly includes a flexible electrode layer including the therapy side, at least one of the first electrode assembly and the second electrode assembly includes a sensor housing configured to receive one of the first motion sensor or the second motion sensor and attached to the electrode layer at an attachment region, and wherein at least a portion of the electrode layer is constructed and arranged to deflect from the sensor housing at a location away from the attachment region such that the electrode layer substantially conforms to an anatomy of a patient.

12. The system of claim 1, wherein the resuscitation assembly includes a cable extending from at least one of the first electrode assembly and the second electrode assembly toward the processing circuitry, and the cable further includes additional processing circuitry.

13. The system of claim 12, wherein the additional processing circuitry of the cable is configured to process signals from the first and second motion sensors by subtracting acceleration signals from the first and second motion sensors.

14. The system of claim 1, wherein the processing circuitry is configured to receive and process signals from at least one of the first and second motion sensors to estimate release velocity, and the output device is configured to provide guidance to the user based on the estimated release velocity.

15. The system of claim 1, wherein the processing circuitry is configured to determine whether electrotherapy is required based on the processed ECG signals after receiving and processing the ECG signals from the first and second electrode assemblies and prior to delivering electrotherapy through the first and second electrode assemblies.

16. The system of claim 1, wherein the processing circuitry is configured to adjust electrotherapy based on the identification of the resuscitation assembly as pediatric or adult.

17. The system of claim 1, wherein the output device is configured to provide instructions to a user for a surface upon which a patient is positioned to be changed based on information sensed from the first and second motion sensors.

18. The system of claim 1, wherein the processing circuitry is configured to estimate an angle relative to a vertical axis of a patient at which a user is administering chest compressions during CPR based on the signals received from the first and second motion sensors.

19. The system of claim 1, wherein the processing circuitry is configured to estimate rate of ventilations applied to a patient based on a signal from at least one of the first motion sensor and the second motion sensor.

20. The system of claim 19, wherein the output device is configured to provide instructions to a user for administering ventilations to the patient based on the estimated rate of ventilations.

21. A system for facilitating resuscitation, comprising:
a resuscitation assembly comprising:
a first electrode assembly comprising a therapy side configured to sense ECG signals and deliver a therapeutic shock and a first motion sensor,
a second electrode assembly comprising a therapy side configured to sense ECG signals and deliver a therapeutic shock and a second motion sensor, and an identification component associated with the resuscitation assembly;
processing circuitry operatively connected to the resuscitation assembly and configured to
identify the resuscitation assembly as one of a pediatric or adult resuscitation assembly based on an identification signal produced by the identification component,
receive and process signals from at least one of the first and second motion sensors to estimate at least one of a compression depth and rate during administration of chest compressions, and
receive and process ECG signals from the first and second electrode assemblies and deliver electrotherapy through the first and second electrode assemblies; and
an output device for providing one or more chest compression parameters including at least one of the estimated compression depth and the estimated compression rate for a user,
wherein the output device is configured to adjust presentation of the one or more chest compression parameters based on whether the resuscitation assembly is identified as pediatric or adult,
wherein at least one of the first motion sensor and the second motion sensor comprises an accelerometer capable of measuring acceleration in multiple directions,
wherein the processing circuitry is configured to estimate a difference in orientation between the first electrode assembly and the second electrode assembly based on a signal from at least one of the first motion sensor and the second motion sensor, and
wherein the output device is configured to provide instructions to a user for administering chest compressions based on the estimation of orientation between the first and second electrode assemblies.

22. The system of claim 21, wherein the processing circuitry is configured to determine a placement orientation of the first electrode assembly and the second electrode assembly on a patient based on a signal from at least one of the first motion sensor and the second motion sensor.

23. The system of claim 22, wherein the processing circuitry is configured to determine whether the first electrode assembly is positioned on a first portion of the patient's anatomy based on a signal from the first motion sensor and whether the second electrode assembly is positioned on a second portion of the patient's anatomy in an anterior-posterior orientation based on a signal from the second motion sensor.

24. The system of claim 22, wherein the processing circuitry is configured to determine whether the first electrode assembly is positioned on a first portion of the patient's anatomy based on a signal from the second motion sensor and whether the second electrode assembly is positioned on a second portion of the patient's anatomy in an anterior-anterior orientation based on a signal from the second motion sensor.

25. The system of claim 21, wherein at least one of the first motion sensor and the second motion sensor is separable from the respective first or second electrode assembly.

26. The system of claim 21, wherein the estimated chest compression depth is calculated by subtracting a distance traveled by the second motion sensor from a distance traveled by the first motion sensor.

27. The system of claim 21, wherein the first motion sensor is configured to produce a first signal representative of acceleration caused by compressions and the second motion sensor is configured to produce a second signal representative of acceleration due to movement on a compressible surface.

28. The system of claim 21, wherein the identification component comprises at least one of a memory and a resistor from which the identification signal is based and the processing circuitry is configured to adjust a shock algorithm based on the identification of the resuscitation assembly as pediatric or adult.

29. The system of claim 21, wherein at least one of the first electrode assembly and the second electrode assembly includes a flexible electrode layer including the therapy side, at least one of the first electrode assembly and the second electrode assembly includes a sensor housing configured to receive one of the first motion sensor or the second motion sensor and attached to the electrode layer at an attachment region, and wherein at least a portion of the electrode layer is constructed and arranged to deflect from the sensor housing at a location away from the attachment region such that the electrode layer substantially conforms to an anatomy of a patient.

30. The system of claim 21, wherein the resuscitation assembly includes a cable extending from at least one of the first electrode assembly and the second electrode assembly toward the processing circuitry, and the cable further includes additional processing circuitry.

31. The system of claim 30, wherein the additional processing circuitry of the cable is configured to process signals from the first and second motion sensors by subtracting acceleration signals from the first and second motion sensors.

32. The system of claim 21, wherein the processing circuitry is configured to receive and process signals from at least one of the first and second motion sensors to estimate release velocity, and the output device is configured to provide guidance to the user based on the estimated release velocity.

33. The system of claim 21, wherein the processing circuitry is configured to determine whether electrotherapy is required based on the processed ECG signals after receiving and processing the ECG signals from the first and second electrode assemblies and prior to delivering electrotherapy through the first and second electrode assemblies.

34. The system of claim 21, wherein the processing circuitry is configured to adjust electrotherapy based on the identification of the resuscitation assembly as pediatric or adult.

35. The system of claim 21, wherein the output device is configured to provide instructions to a user for a surface upon which a patient is positioned to be changed based on information sensed from the first and second motion sensors.

36. The system of claim 21, wherein the processing circuitry is configured to estimate rate of ventilations applied to a patient based on a signal from at least one of the first motion sensor and the second motion sensor.

37. The system of claim 36, wherein the output device is configured to provide instructions to a user for administering ventilations to the patient based on the estimated rate of ventilations.

* * * * *

UNITED STATES PATENT AND TRADEMARK OFFICE
CERTIFICATE OF CORRECTION

PATENT NO. : 10,406,345 B2
APPLICATION NO. : 15/282530
DATED : September 10, 2019
INVENTOR(S) : Annemarie Silver et al.

Page 1 of 1

It is certified that error appears in the above-identified patent and that said Letters Patent is hereby corrected as shown below:

In the Claims

Column 43, Line 41, Claim 1, delete "sensor" and insert -- sensor, --

Signed and Sealed this
Twelfth Day of November, 2019

Andrei Iancu
*Director of the United States Patent and Trademark Office*